(12) United States Patent
Müller et al.

(10) Patent No.: US 6,762,152 B1
(45) Date of Patent: Jul. 13, 2004

(54) SUBSTITUTED BENZOYL KETONES, METHODS FOR PRODUCING THEM AND THEIR USE AS HERBICIDES

(75) Inventors: Klaus-Helmut Müller, Düsseldorf (DE); Stefan Lehr, Langenfeld (DE); Otto Schallner, Monheim (DE); Hans-Georg Schwarz, Langenfeld (DE); Heinz-Jürgen Wroblowsky, Langenfeld (DE); Mark Wilhelm Drewes, Langenfeld (DE); Dieter Feucht, Monheim (DE); Rolf Pontzen, Leichlingen (DE); Ingo Wetcholowsky, Estancia Marambaia (BR)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/009,981

(22) PCT Filed: Apr. 26, 2000

(86) PCT No.: PCT/EP00/03712

§ 371 (c)(1),
(2), (4) Date: Nov. 5, 2001

(87) PCT Pub. No.: WO00/68204

PCT Pub. Date: Nov. 16, 2000

(30) Foreign Application Priority Data

May 8, 1999 (DE) .......................................... 199 21 424

(51) Int. Cl.$^7$ .................... C07D 249/12; C07D 285/12; C07D 247/00; C07D 227/02; A01N 43/00
(52) U.S. Cl. .................... 504/273; 514/384; 548/263.2; 548/263.4
(58) Field of Search .......................... 548/263.2, 263.4; 514/384; 504/273

(56) References Cited

U.S. PATENT DOCUMENTS

| | | | |
|---|---|---|---|
| 3,742,014 A | 6/1973 | Grivsky | 260/465 B |
| 3,978,127 A | 8/1976 | Engelhardt et al. | 260/570.5 R |
| 4,542,127 A | 9/1985 | Hitzel et al. | 514/161 |
| 4,837,333 A | 6/1989 | Manley et al. | 548/341 |
| 5,171,748 A | 12/1992 | Roberts et al. | 514/381 |
| 5,185,351 A | 2/1993 | Finkelstein et al. | 514/381 |
| 5,189,033 A | 2/1993 | Tucker | 514/211 |
| 5,378,681 A | 1/1995 | Schallner et al. | 504/273 |
| 5,418,250 A | 5/1995 | Finkelstein et al. | 514/397 |
| 5,464,810 A | 11/1995 | Haas et al. | 504/273 |

(List continued on next page.)

FOREIGN PATENT DOCUMENTS

| | | |
|---|---|---|
| CA | 2102750 | 5/1994 |
| CA | 2183641 | 8/1995 |
| EP | 0 093 488 | 11/1983 |
| EP | 0 617 026 | 7/1997 |
| JP | 58-225070 | 12/1983 |
| JP | 2-15069 | 1/1990 |
| WO | 95/04716 | 2/1995 |
| WO | 97/27187 | 7/1997 |
| WO | 97/28122 | 8/1997 |
| WO | 97/28136 | 8/1997 |
| WO | 98/51153 | 11/1998 |
| WO | 99/03856 | 1/1999 |

OTHER PUBLICATIONS

Hampel (Journal fuer praktische Chemie (Leipzig) (1969), 311(1), 78–81). Abstract.*

(List continued on next page.)

*Primary Examiner*—Bruck Kifle
(74) *Attorney, Agent, or Firm*—Richard E. L. Henderson; Joseph C. Gil

(57) ABSTRACT

The invention relates to novel substituted benzoyl ketones of the formula (I)

$$R^1 \!-\! \underset{\underset{R^2}{|}}{C(O)} \!-\! CH \!-\! C(O) \!-\! \text{Ar}(R^3)(R^4)_n \!-\! A \!-\! Z \quad (I)$$

in which n represents 0, 1, 2 or 3,

A represents a single bond or represents alkanediyl (alkylene), $R^1$ represents hydrogen or represents in each case optionally substituted alkyl or cycloalkyl, $R^2$ represents hydrogen, cyano, carbamoyl, halogen, or represents in each case optionally substituted alkyl, alkoxy, alkoxycarbonyl, alkylthio, alkylsulphinyl or alkylsulphonyl, $R^3$ represents hydrogen, nitro, cyano, carboxyl, carbamoyl, thiocarbamoyl, halogen, or represents in each case optionally substituted alkyl, alkoxy, alkylthio, alkylsulphinyl, alkylsulphonyl, alkylamino, dialkylamino or dialkylaminosulphonyl, $R^4$ represents nitro, cyano, carboxyl, carbamoyl, thiocarbamoyl, halogen, or represents in each case optionally substituted alkyl, alkoxy, alkylthio, alkylsulphinyl, alkylsulphonyl, alkylamino, dialkyiamino or dialkylaminosulphonyl, and Z represents an optionally substituted 4- to 12-membered, saturated or unsaturated, monocyclic or bicyclic, heterocyclic grouping which, contains 1 to 4 hetero atoms (up to 4 nitrogen atoms and optionally—alternatively or additionally—one oxygen atom or one sulphur atom, or one SO grouping or one $SO_2$ grouping) and which additionally contains one to three oxo g of the heterocycle roups (C=O) and/or thioxo groups (C=S) as components, of the heterocycle, and to processes for their preparation and to their use as herbicides.

17 Claims, No Drawings

U.S. PATENT DOCUMENTS

| | | | |
|---|---|---|---|
| 5,476,946 A | 12/1995 | Linker et al. | 504/273 |
| 5,554,580 A | 9/1996 | Fischer et al. | 504/281 |
| 5,663,362 A | 9/1997 | Haas et al. | 548/263.2 |
| 5,804,532 A | 9/1998 | Cain et al. | 504/309 |
| 5,846,906 A | 12/1998 | von Deyn et al. | 504/221 |
| 5,880,147 A | 3/1999 | Yoshida et al. | 514/452 |
| 6,040,339 A | 3/2000 | Yoshida et al. | 514/485 |
| 6,063,789 A | 5/2000 | Hamley et al. | 514/301 |

OTHER PUBLICATIONS

Harris et al. (Journal of the American Chemical Society (1975), 97(11), 3270–1). Abstract.*
Doub et al. (DE 2502119). Abstract.*
Schaeffer et al. (FR 2654527). Abstract.*
Djuric et al. (WO 92/21644). Abstract.*
Von Deyn et al. (WO 96/26193). Abstract.*
Von Deyn et al. (WO 96/26192). Abstract.*
Go et al. (WO 97/27187). Abstract.*

* cited by examiner

SUBSTITUTED BENZOYL KETONES, METHODS FOR PRODUCING THEM AND THEIR USE AS HERBICIDES

FIELD OF THE INVENTION

The invention relates to novel substituted benzoyl ketones, to processes for their preparation and to their use as herbicides.

BACKGROUND OF THE INVENTION

It is already known that certain substituted benzoyl ketones have herbicidal properties. (cf. EP-A-625505, EP-A-625508, U.S. Pat. No. 5,804,532, U.S. Pat. No. 5,846,906, WO-A-96/26193). However, the activity of these compounds is not entirely satisfactory.

This invention, accordingly, provides the novel substituted benzoyl ketones of the formula (I),

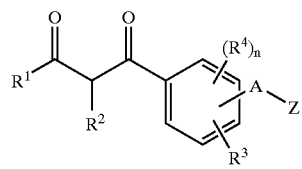

in which
- n represents 0, 1, 2 or 3,
- A represents a single bond or represents alkanediyl (alkylene),
- $R^1$ represents hydrogen or represents in each case optionally substituted alkyl or cycloalkyl,
- $R^2$ represents hydrogen, cyano, carbamoyl, halogen, or represents in each case optionally substituted alkyl, alkoxy, alkoxycarbonyl, alkylthio, alkylsulphinyl or alkylsulphonyl,
- $R^3$ represents hydrogen, nitro, cyano, carboxyl, carbamoyl, thiocarbamoyl, halogen, or represents in each case optionally substituted alkyl, alkoxy, alkylthio, alkylsulphinyl, alkylsulphonyl, alkylamino, dialkylamino or dialkylaminosulphonyl,
- $R^4$ represents nitro, cyano, carboxyl, carbamoyl, thiocarbamoyl, halogen, or represents in each case optionally substituted alkyl, alkoxy, alkylthio, alkylsulphinyl, alkylsulphonyl, alkylamino, dialkylamino or dialkylaminosulphonyl, and

DETAILED DESCRIPTION

Z represents an optionally substituted 4- to 12-membered, saturated or unsaturated, monocyclic or bicyclic, heterocyclic grouping which contains 1 to 4 hetero atoms (up to 4 nitrogen atoms and optionally—alternatively or additionally—one oxygen atom or one sulphur atom, or one SO grouping or one $SO_2$ grouping) and which additionally contains one to three oxo groups (C=O) and/or thioxo groups (C=S) as components of the heterocycle, including all possible tautomeric forms of the compounds of the general formula (I) and the possible salts of the compounds of the general formula (I).

In the definitions, the hydrocarbon chains, such as alkyl or alkanediyl, are in each case straight-chain or branched—including in combination with heteroatoms, such as in alkoxy.

n preferably represents 0, 1 or 2.

A preferably represents a single bond or represents alkanediyl (alkylene) having 1 to 4 carbon atoms.

$R^1$ preferably represents hydrogen, represents optionally cyano, carboxyl, carbamoyl, halogen, $C_1$-$C_4$-alkoxy-, $C_1$-$C_4$-alkylthio-, $C_1$-$C_4$-alkylsulphinyl- or $C_1$-$C_4$-alkylsulphonyl-substituted alkyl having 1 to 6 carbon atoms, or represents optionally cyano-, carboxyl-, carbamoyl-, halogen-, $C_1$-$C_4$-alkyl- or $C_1$-$C_4$-alkoxycarbonyl-substituted cycloalkyl having 3 to 6 carbon atoms.

$R^2$ preferably represents hydrogen, cyano, carbamoyl, halogen, represents in each case optionally cyano-, carbamoyl-, halogen- or $C_1$-$C_4$-alkoxy-substituted alkyl, alkoxy or alkoxycarbonyl having in each case up to 6 carbon atoms, or represents in each case optionally halogen-substituted alkylthio, alkylsulphinyl or alkylsulphonyl having in each case 1 to 6 carbon atoms.

$R^3$ preferably represents hydrogen, nitro, cyano, carboxyl, carbamoyl, thiocarbamoyl, halogen, represents in each case optionally halogen-, $C_1$-$C_4$-alkoxy-, $C_1$-$C_4$-alkylthio-, $C_1$-$C_4$-alkylsulphinyl- or $C_1$-$C_4$-alkylsulphonyl-substituted alkyl, alkoxy, alkylthio, alkylsulphinyl or alkylsulphonyl having in each case up to 4 carbon atoms in the alkyl groups, or represents alkylamino, dialkylamino or dialkylaminosulphonyl having in each case up to 4 carbon atoms in the alkyl groups.

$R^4$ preferably represents nitro, cyano, carboxyl, carbamoyl, thiocarbamoyl, halogen, represents in each case optionally halogen-, $C_1$-$C_4$-alkoxy-, $C_1$-$C_4$-alkylthio-, $C_1$-$C_4$-alkylsulphinyl- or $C_1$-$C_4$-alkylsulphonyl-substituted alkyl, alkoxy, alkylthio, alkylsulphinyl or alkylsulphonyl having in each case up to 4 carbon atoms in the alkyl groups, or represents alkylamino, dialkylamino or dialkylaminosulphonyl having in each case up to 4 carbon atoms in the alkyl groups.

Z preferably represents one of the heterocyclic groupings below

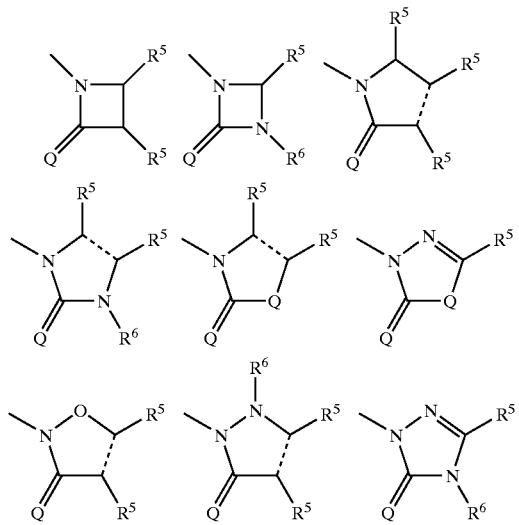

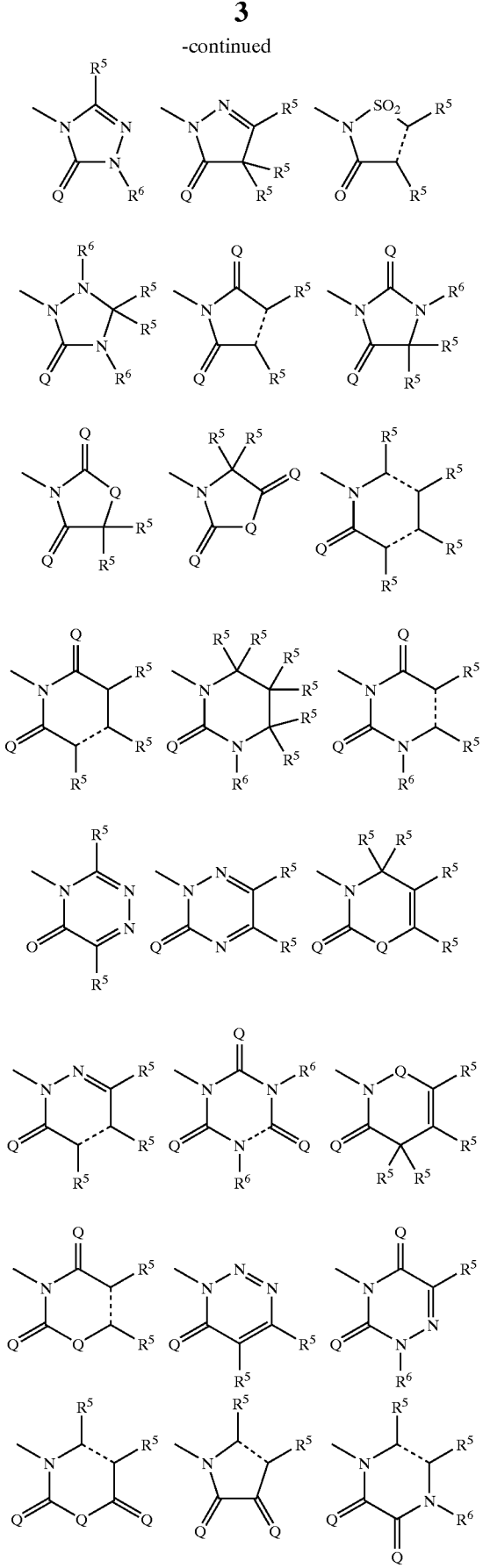
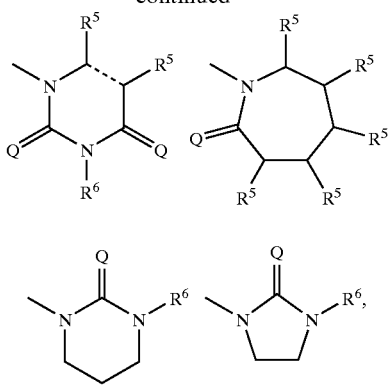

where the dotted line is in each case a single bond or a double bond, and each heterocyclic grouping preferably only carries two substituents of the definition $R^5$ and/or $R^6$, Q represents oxygen or sulphur, $R^5$ represents hydrogen, hydroxyl, mercapto, cyano, halogen, represents in each case optionally cyano-, halogen-, $C_1$–$C_4$-alkoxy-, $C_1$–$C_4$-alkylthio-, $C_1$–$C_4$-alkylsulphinyl- or $C_1$–$C_4$-alkylsulphonyl-substituted alkyl, alkylcarbonyl, alkoxy, alkoxycarbonyl, alkylthio, alkylsulphinyl or alkylsulphonyl having in each case up to 6 carbon atoms in the alkyl groups, represents in each case optionally halogen-substituted alkylamino or dialkylamino having in each case up to 6 carbon atoms in the alkyl groups, represents in each case optionally halogen-substituted alkenyl, alkinyl, alkenyloxy, alkenylthio or alkenylamino having in each case up to 6 carbon atoms in the alkenyl- or alkinyl groups, represents in each case optionally halogen-substituted cycloalkyl, cycloalkyloxy, cycloalkylthio, cycloalkylamino, cycloalkylalkyl, cycloalkylalkoxy, cycloalkylalkylthio or cycloalkylalkylamino having in each case 3 to 6 carbon atoms in the cycloalkyl groups and optionally up to 4 carbon atoms in the alkyl moiety, or represents in each case optionally halogen-, $C_1$–$C_4$-alkyl- or $C_1$–$C_4$-alkoxy-substituted phenyl, phenyloxy, phenylthio, phenylamino, benzyl, benzyloxy, benzylthio or benzylamino, or—if two adjacent radicals $R^5$ and $R^5$ are located at a double bond—together with the adjacent radical $R^5$ also represents a benzo grouping, and $R^6$ represents hydrogen, hydroxyl, amino, alkylideneamino having up to 4 carbon atoms, represents in each case optionally halogen- or $C_1$–$C_4$-alkoxy-substituted alkyl, alkoxy, alkylamino, dialkylamino or alkanoylamino having in each case up to 6 carbon atoms in the alkyl groups, represents in each case optionally halogen-substituted alkenyl, alkinyl or alkenyloxy having in each case up to 6 carbon atoms in the alkenyl- or alkinyl groups, represents in each case optionally halogen-substituted cycloalkyl, cycloalkylalkyl or cycloalkylamino having in each case 3 to 6 carbon atoms in the cycloalkyl groups and optionally up to 3 carbon atoms in the alkyl moiety, or represents in each case optionally halogen-, $C_1$–$C_4$-alkyl- or $C_1$–$C_4$-alkoxy-substituted phenyl or benzyl, or together with an adjacent radical $R^5$ or $R^6$ represents optionally halogen- or $C_1$–$C_4$-alkyl-substituted alkanediyl having 3 to 5 carbon atoms, where the individual radicals $R^5$ and $R^6$—if a plurality of them are attached to the same heterocyclic grouping—can have identical or different meanings within the scope of the above definition.

Q preferably represents oxygen.

$R^5$ preferably represents hydrogen, hydroxyl, mercapto, cyano, fluorine, chlorine, bromine, iodine, represents in each case optionally fluorine-, chlorine-, methoxy-, ethoxy-, n- or i-propoxy-, n-, i-, s- or t-butoxy-, methylthio-, ethylthio-, n- or i-propylthio-, n-, i-, s- or t-butylthio-, methylsulphinyl-, ethylsulphinyl-, n- or i-propylsulphinyl-, methylsulphonyl-, ethylsulphonyl-, n- or i-propylsulphonyl-substituted methyl, ethyl, n- or i-propyl, n-, i-, s- or t-butyl, methoxy, ethoxy, n- or i-propoxy, n-, i-, s- or t-butoxy, methylthio, ethylthio, n- or i-propylthio, n-, i-, s- or t-butylthio, methylsulphinyl, ethylsulphinyl, n- or i-propylsulphinyl, methylsulphonyl, ethylsulphonyl, n- or i-propylsulphonyl, represents methylamino, ethylamino, n- or i-propylamino, n-, i-, s- or t-butylamino, dimethylamino, diethylamino, di-n-propylamino or di-i-propylamino, represents in each case optionally fluorine- and/or chlorine-substituted ethenyl, propenyl, butenyl, ethinyl, propinyl, butinyl, propenyloxy, butenyloxy, propenylthio, butenylthio, propenylamino or butenylamino, represents in each case optionally fluorine- and/or chlorine-substituted cyclopropyl, cyclobutyl, cyclopentyl, cyclohexyl, cyclopropyloxy, cyclobutyloxy, cyclopentyloxy, cyclohexyloxy, cyclopropylthio, cyclobutylthio, cyclopentylthio, cyclohexylthio, cyclopropylamino, cyclobutylamino, cyclopentylamino, cyclohexylamino, cyclopropylmethyl, cyclobutylmethyl, cyclopentylmethyl, cyclohexylmethyl, cyclopropylmethoxy, cyclobutylmethoxy, cyclopentylmethoxy, cyclohexylmethoxy, cyclopropylmethylthio, cyclobutylmethylthio, cyclopentylmethylthio, cyclohexylmethylthio, cyclopropylmethylamino, cyclobutylmethylamino, cyclopentylmethylamino or cyclohexylmethylamino, or represents in each case optionally fluorine-, chlorine-, methyl-, ethyl-, n- or i-propyl-, n-, i-, s- or t-butyl-, methoxy-, ethoxy-, n- or i-propoxy-substituted phenyl, phenyloxy, phenylthio, phenylamino, benzyl, benzyloxy, benzylthio or benzylamino, or—if two adjacent radicals $R^5$ and $R^5$ are located at a double bond—together with the adjacent radical $R^5$ also represents a benzo grouping.

$R^6$ preferably represents hydrogen, hydroxyl, amino, represents in each case optionally fluorine- and/or chlorine-, methoxy- or ethoxy-substituted methyl, ethyl, n- or i-propyl, n-, i- or s-butyl, methoxy, ethoxy, n- or i-propoxy, methylamino, ethylamino or dimethylamino, represents in each case optionally fluorine- and/or chlorine-substituted ethenyl, propenyl, ethinyl, propinyl or propenyloxy, represents in each case optionally fluorine- and/or chlorine-substituted cyclopropyl, cyclobutyl, cyclopentyl, cyclohexyl, cyclopropylmethyl, cyclobutylmethyl, cyclopentylmethyl or cyclohexylmethyl, or represents in each case optionally fluorine-, chlorine-, methyl-, ethyl-, n- or i-propyl-, n-, i-, s- or t-butyl-, methoxy-, ethoxy-, n- or i-propoxy-substituted phenyl or benzyl, or together with an adjacent radical $R^5$ or $R^6$ represents in each case optionally methyl- and/or ethyl-substituted propane-1,3-diyl (trimethylene), butane-1,4-diyl (tetramethylene) or pentane-1,5-diyl (pentamethylene).

n particularly preferably represents 0 or 1.

A particularly preferably represents a single bond, methylene, ethylidene (ethane-1,1-diyl) or dimethylene (ethane-1,2-diyl).

$R^1$ particularly preferably represents hydrogen, represents in each case optionally cyano-, carboxyl-, carbamoyl-, fluorine-, chlorine-, methoxy-, ethoxy-, n- or i-propoxy-, methylthio-, ethylthio-, n- or i-propylthio-, methylsulphinyl-, ethylsulphinyl-, n- or i-propylsulphinyl-, methylsulphonyl-, ethylsulphonyl-, n- or i-propylsulphonyl-substituted methyl, ethyl, n- or i-propyl, n-, i-, s- or t-butyl, or represents in each case optionally cyano-, carboxyl-, carbamoyl-, fluorine-, chlorine-, methyl-, ethyl-, methoxycarbonyl- or ethoxycarbonyl-substituted cyclopropyl, cyclobutyl, cyclopentyl or cyclohexyl.

$R^2$ particularly preferably represents hydrogen, cyano, carbamoyl, fluorine, chlorine, bromine, represents in each case optionally cyano-, carbamoyl-, fluorine-, chlorine-, methoxy- or ethoxy-substituted methyl, ethyl, n- or i-propyl, methoxy, ethoxy, n- or i-propoxy, methoxycarbonyl, ethoxycarbonyl, n- or i-propoxycarbonyl, or represents in each case optionally fluorine- and/or chlorine-substituted methylthio, ethylthio, n- or i-propylthio, methylsulphinyl, ethylsulphinyl, n- or i-propylsulphinyl, methylsulphonyl, ethylsulphonyl, n- or i-propylsulphonyl.

$R^3$ particularly preferably represents hydrogen, nitro, cyano, carboxyl, carbamoyl, thiocarbamoyl, fluorine, chlorine, bromine, iodine, represents in each case optionally fluorine- and/or chlorine-, methoxy-, ethoxy-, n- or i-propoxy-, methylthio-, ethylthio-, n- or i-propylthio-, methylsulphinyl-, ethylsulphinyl-, methylsulphonyl- or ethylsulphonyl-substituted methyl, ethyl, n- or i-propyl, n-, i-, s- or t-butyl, represents in each case optionally fluorine- and/or chlorine-, methoxy-, ethoxy-, n- or i-propoxy-substituted methoxy, ethoxy, n- or i-propoxy, represents in each case optionally fluorine- and/or chlorine-substituted methylthio, ethylthio, n- or i-propylthio, methylsulphinyl, ethylsulphinyl, n- or i-propylsulphinyl, methylsulphonyl, ethylsulphonyl, n- or i-propylsulphonyl, or represents methylamino, ethylamino, n- or i-propylamino, dimethylamino, diethylamino, dimethylaminosulphonyl or diethylaminosulphonyl.

$R^4$ particularly preferably represents nitro, cyano, carboxyl, carbamoyl, thiocarbamoyl, fluorine, chlorine, bromine, represents in each case optionally fluorine- and/or chlorine-, methoxy-, ethoxy-, n- or i-propoxy-, methylthio-, ethylthio-, n- or i-propylthio-, methylsulphinyl-, ethylsulphinyl-, methylsulphonyl- or ethylsulphonyl-substituted methyl, ethyl, n- or i-propyl, n-, i-, s- or t-butyl, represents in each case optionally fluorine- and/or chlorine-, methoxy-, ethoxy-, n- or i-propoxy-substituted methoxy, ethoxy, n- or i-propoxy, represents in each case optionally fluorine- and/or chlorine-substituted methylthio, ethylthio, n- or i-propylthio, methylsulphinyl, ethylsulphinyl, n- or i-propylsulphinyl, methylsulphonyl, ethylsulphonyl, n- or i-propylsulphonyl, or represents methylamino, ethylamino, n- or i-propylamino, dimethylamino, diethylamino, dimethylaminosulphonyl or diethylaminosulphonyl.

$R^5$ particularly preferably represents hydrogen, hydroxyl, chlorine, bromine, methyl, ethyl, n- or i-propyl, n-, i-, s- or t-butyl, difluoromethyl, dichloromethyl, trifluoromethyl, trichloromethyl, chlorodifluoromethyl, fluorodichloromethyl, fluoroethyl, chloroethyl, difluoroethyl, dichloroethyl, fluoro-n-propyl, fluoro-i-propyl, chloro-n-propyl, chloro-i-propyl, methoxymethyl, ethoxymethyl, methoxyethyl, ethoxyethyl, methoxy, ethoxy, n- or i-propoxy, n-, i-, s- or t-butoxy, fluoroethoxy, chloroethoxy, difluoroethoxy, dichloroethoxy, trifluoroethoxy, trichloroethoxy, chlorofluoroethoxy, chlorodifluoroethoxy, fluorodichloroethoxy, methylthio, ethylthio, n- or i-propylthio, fluoroethylthio, chloroethylthio, difluoroethylthio, dichloroethylthio, chlorofluoroethylthio, chlorodifluoroethylthio, fluorodichloroethylthio, methylsulphinyl, ethylsulphinyl, n- or i-propylsulphinyl, methylsulphonyl, ethylsulphonyl, n- or i-propylsulphonyl, methylamino, dimethylamino, propenylthio, butenylthio, propinylthio, butinylthio, cyclopropyl, cyclopropylmethyl, cyclopropylmethoxy, phenyl or phenoxy.

$R^6$ particularly preferably represents amino, methyl, ethyl, n- or i-propyl, n-, i-, s- or t-butyl, methoxy, ethoxy, methylamino, dimethylamino, cyclopropyl or cyclopropylmethyl, or together with $R^5$ represents propane-1,3-diyl (trimethylene), butane-1,4-diyl (tetramethylene) or pentane-1,5-diyl (pentamethylene).

Z particularly preferably represents the groupings below

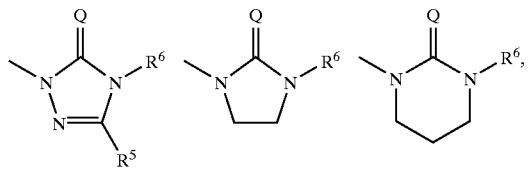

where Q, $R^5$ and $R^6$ are each as defined above.

A very particularly preferably represents a single bond or represents methylene.

$R^1$ very particularly preferably represents in each case optionally cyano-, fluorine-, chlorine-, methoxy-, ethoxy-, n- or i-propoxy-, methylthio-, ethylthio-, n- or o-propylthio-, methylsulphinyl-, ethylsulphinyl-, n- or i-propylsulphinyl-, methylsulphonyl-, ethylsulphonyl-, n- or i-propylsulphonyl-substituted methyl, ethyl, n- or i-propyl, or represents in each case optionally cyano-, fluorine-, chlorine-, methyl- or ethyl-substituted cyclopropyl, cyclobutyl, cyclopentyl or cyclohexyl.

$R^2$ very particularly preferably represents hydrogen, cyano, carbamoyl, fluorine, chlorine, bromine, represents in each case optionally cyano-, carbamoyl-, fluorine-, chlorine-, methoxy- or ethoxy-substituted methyl, ethyl, n- or i-propyl, or represents in each case optionally fluorine- and/or chlorine-substituted methylthio, ethylthio, n- or i-propylthio, methylsulphinyl, ethylsulphinyl, n- or i-propylsulphinyl, methylsulphonyl, ethylsulphonyl, n- or i-propylsulphonyl.

$R^3$ very particularly preferably represents hydrogen, nitro, cyano, carboxyl, carbamoyl, thiocarbamoyl, fluorine, chlorine, bromine, represents in each case optionally fluorine- and/or chlorine-, methoxy-, ethoxy-, n- or i-propoxy-, methylthio-, ethylthio-, n- or i-propylthio-, methylsulphinyl-, ethylsulphinyl-, methylsulphonyl- or ethylsulphonyl-substituted methyl, ethyl, n- or i-propyl, n-, i-, s- or t-butyl, represents in each case optionally fluorine- and/or chlorine-, methoxy-, ethoxy-, n- or i-propoxy-substituted methoxy, ethoxy, n- or i-propoxy, represents in each case optionally fluorine- and/or chlorine-substituted methylthio, ethylthio, n- or i-propylthio, methylsulphinyl, ethylsulphinyl, n- or i-propylsulphinyl, methylsulphonyl, ethylsulphonyl, n- or i-propylsulphonyl, or represents methylamino, ethylamino, n- or i-propylamnino, dimethylamino, diethylamino, dimethylaminosulphonyl or diethylaminosulphonyl.

$R^4$ very particularly preferably represents methylsulphonyl, chlorine, methoxy, nitro, trifluoromethyl or methyl.

$R^5$ very particularly preferably represents hydrogen, bromine, chlorine, methyl, ethyl, trifluoromethyl, cyclopropyl, difluoroethyl, methylthio, ethylthio, methoxy, ethoxy, n- or i-propoxy, trifluoroethoxy, methylamino or dimethylamino.

$R^6$ very particularly preferably represents hydrogen, amino, methyl, ethyl, cyclopropyl, dimethylamino methoxy or ethoxy.

$R^1$ most preferably represents cyclopropyl.

$R^2$ most preferably represents hydrogen or cyano.

$R^3$ most preferably represents hydrogen, nitro, cyano, fluorine, chlorine, bromine, methyl, trifluoromethyl or methoxy.

$R^5$ most preferably represents bromine, methyl, ethyl, methoxy, methylthio, ethoxy, methylsulfonyl or dimethylamino.

$R^6$ most preferably represents amino, methyl, ethyl, cyclopropyl, dimethylamino, methoxy or ethoxy.

Preference according to the invention is given to the compounds of the formula (I) which contain a combination of the meanings given above as being preferred.

Particular preference according to the invention is given to the compounds of the formula (I) which contain a combination of the meanings given above as being particularly preferred.

Very particular preference according to the invention is given to the compounds of the formula (I) which contain a combination of the meanings given above as being very particularly preferred.

Most preference according to the invention is given to the compounds of the formula (I) which contain a combination of the meanings given above as being most preferred.

Part of the subject-matter of the present invention are in particular the compounds of the formulae (IA), (IB) and (IC):

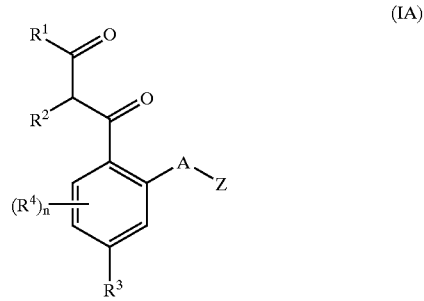

(IA)

-continued

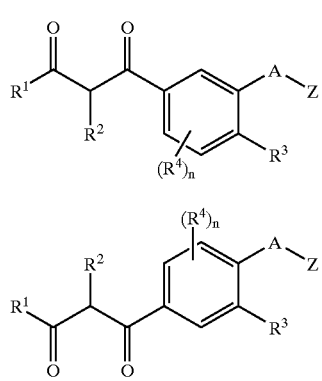
(IB)

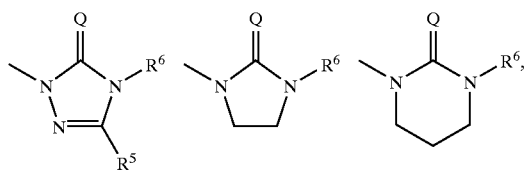
(IC)

in which
Z represents the groupings below

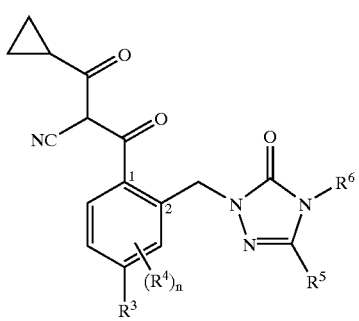

and n, A, Q, $R^1$, $R^2$, $R^3$, $R^4$, $R^5$ and $R^6$ are each as defined above.

The abovementioned general or preferred radical definitions apply both to the end products of the formula (I) and, correspondingly, to the starting materials or intermediates required in each case for the preparation. These radical definitions can be combined with one another as desired, i.e. including combinations between the given preferred ranges.

Examples of the compounds of the general formula (I) according to the invention are listed in the groups below.

Group 1

(IA-1)

$R^3$, $(R^4)_n$, $R^5$ and $R^6$ have example, the meaning given in the table below:

| $R^3$ | (position-)$(R^4)_n$ | $R^5$ | $R^6$ |
|---|---|---|---|
| H | — | $CF_3$ | $CH_3$ |
| F | — | $CF_3$ | $CH_3$ |
| Cl | — | $CF_3$ | $CH_3$ |
| Br | — | $CF_3$ | $CH_3$ |
| I | — | $CF_3$ | $CH_3$ |
| $NO_2$ | — | $CF_3$ | $CH_3$ |
| CN | — | $CF_3$ | $CH_3$ |
| $CH_3$ | — | $CF_3$ | $CH_3$ |
| $OCH_3$ | — | $CF_3$ | $CH_3$ |
| $CF_3$ | — | $CF_3$ | $CH_3$ |
| $OCHF_2$ | — | $CF_3$ | $CH_3$ |
| $OCF_3$ | — | $CF_3$ | $CH_3$ |
| $SO_2CH_3$ | — | $CF_3$ | $CH_3$ |
| H | — | $OCH_3$ | $CH_3$ |
| F | — | $OCH_3$ | $CH_3$ |
| Cl | — | $OCH_3$ | $CH_3$ |
| Br | — | $OCH_3$ | $CH_3$ |
| I | — | $OCH_3$ | $CH_3$ |
| $NO_2$ | — | $OCH_3$ | $CH_3$ |
| CN | — | $OCH_3$ | $CH_3$ |
| $CH_3$ | — | $OCH_3$ | $CH_3$ |
| $OCH_3$ | — | $OCH_3$ | $CH_3$ |
| $CF_3$ | — | $OCH_3$ | $CH_3$ |
| $OCHF_2$ | — | $OCH_3$ | $CH_3$ |
| $OCF_3$ | — | $OCH_3$ | $CH_3$ |
| $SO_2CH_3$ | — | $OCH_3$ | $CH_3$ |
| H | — | $SCH_3$ | $CH_3$ |
| F | — | $SCH_3$ | $CH_3$ |
| Cl | — | $SCH_3$ | $CH_3$ |
| Br | — | $SCH_3$ | $CH_3$ |
| CN | — | $N(CH_3)_2$ | $CH_3$ |
| $CH_3$ | — | $N(CH_3)_2$ | $CH_3$ |
| $OCH_3$ | — | $N(CH_3)_2$ | $CH_3$ |
| $CF_3$ | — | $N(CH_3)_2$ | $CH_3$ |
| $OCHF_2$ | — | $N(CH_3)_2$ | $CH_3$ |
| $OCF_3$ | — | $N(CH_3)_2$ | $CH_3$ |
| $SO_2CH_3$ | — | $N(CH_3)_2$ | $CH_3$ |
| H | — | $OCH_3$ | ▲ |
| F | — | $OCH_3$ | ▲ |
| Cl | — | $OCH_3$ | ▲ |
| Br | — | $OCH_3$ | ▲ |
| I | — | $OCH_3$ | ▲ |
| $NO_2$ | — | $OCH_3$ | ▲ |
| CN | — | $OCH_3$ | ▲ |
| $CH_3$ | — | $OCH_3$ | ▲ |
| $OCH_3$ | — | $OCH_3$ | ▲ |
| $CF_3$ | — | $OCH_3$ | ▲ |

-continued

| R³ | (position-)(R⁴)ₙ | R⁵ | R⁶ |
|---|---|---|---|
| I | — | SCH₃ | CH₃ |
| NO₂ | — | SCH₃ | CH₃ |
| CN | — | SCH₃ | CH₃ |
| CH₃ | — | SCH₃ | CH₃ |
| OCH₃ | — | SCH₃ | CH₃ |
| CF₃ | — | SCH₃ | CH₃ |
| OCHF₂ | — | SCH₃ | CH₃ |
| OCF₃ | — | SCH₃ | CH₃ |
| SO₂CH₃ | — | SCH₃ | CH₃ |
| H | — | OC₂H₅ | CH₃ |
| F | — | OC₂H₅ | CH₃ |
| Cl | — | OC₂H₅ | CH₃ |
| Br | — | OC₂H₅ | CH₃ |
| I | — | OC₂H₅ | CH₃ |
| NO₂ | — | OC₂H₅ | CH₃ |
| CN | — | OC₂H₅ | CH₃ |
| CH₃ | — | OC₂H₅ | CH₃ |
| OCH₃ | — | OC₂H₅ | CH₃ |
| CF₃ | — | OC₂H₅ | CH₃ |
| OCHF₂ | — | OC₂H₅ | CH₃ |
| OCF₃ | — | OC₂H₅ | CH₃ |
| SO₂CH₃ | — | OC₂H₅ | CH₃ |
| H | — | N(CH₃)₂ | CH₃ |
| F | — | N(CH₃)₂ | CH₃ |
| Cl | — | N(CH₃)₂ | CH₃ |
| Br | — | N(CH₃)₂ | CH₃ |
| I | — | N(CH₃)₂ | CH₃ |
| NO₂ | — | N(CH₃)₂ | CH₃ |
| OCHF₂ | — | OCH₃ |  |
| OCF₃ | — | OCH₃ |  |
| SO₂CH₃ | — | OCH₃ |  |
| H | (3-) Cl | CF₃ | CH₃ |
| F | (3-) Cl | CH₃ | CH₃ |
| Cl | (3-) Cl | OCH₃ | CH₃ |
| Br | (3-) Cl | Br |  |
| Cl | (3-) Cl | CF₃ | CH₃ |
| NO₂ | (3-) Cl | CH₃ | CH₃ |
| Cl | (3-) Cl | SCH₃ | CH₃ |
| CH₃ | (3-) Cl | Cl | CH₃ |
| OCH₃ | (3-) Cl | OCH₃ | CH₃ |
| CF₃ | (3-) Cl | CF₃ | CH₃ |
| OCHF₂ | (3-) Cl | CH₃ | CH₃ |
| OCF₃ | (3-) Cl | CH₃ | CH₃ |
| SO₂CH₃ | (3-) Cl | OCH₃ | CH₃ |

| R³ | (position-)(R⁴)ₙ | R⁵ | R⁶ |
|---|---|---|---|
| Cl | (2-) Cl | CF₃ | CH₃ |
| Cl | (2-) Cl | SCH₃ | CH₃ |
| Cl | (2-) Cl | SC₂H₅ | CH₃ |
| Cl | (2-) Cl | SC₃H₇ | CH₃ |
| Cl | (2-) Cl | SC₃H₇-i | CH₃ |
| Cl | (2-) Cl | SCH₂CH=CH₂ | CH₃ |
| Cl | (2-) Cl | SCH₂C≡CH | CH₃ |
| Cl | (2-) Cl | SCH=CHCH₃ | CH₃ |
| Cl | (2-) Cl | SC≡CCH₃ | CH₃ |
| Cl | (2-) Cl | S-cyclopropylmethyl | CH₃ |
| Cl | (2-) Cl | SCH=C=CH₂ | CH₃ |
| Cl | (2-) Cl | SCH₂CN | CH₃ |
| Cl | (2-) Cl | SCH₂CH₂CN | CH₃ |
| Cl | (2-) Cl | OCH₃ | CH₃ |
| Cl | (2-) Cl | OC₂H₅ | CH₃ |
| Cl | (2-) Cl | OC₃H₇ | CH₃ |
| Cl | (2-) Cl | OC₃H₇-i | CH₃ |
| Cl | (2-) Cl | OC₄H₉ | CH₃ |
| Cl | (2-) Cl | OCH₂CF₃ | CH₃ |
| Cl | (2-) Cl | O-cyclopropylmethyl | CH₃ |
| Cl | (2-) Cl | OC₆H₅ | CH₃ |
| Cl | (2-) Cl | H | CH₃ |
| Cl | (2-) Cl | CH₃ | CH₃ |
| Cl | (2-) Cl | C₂H₅ | CH₃ |
| Cl | (2-) Cl | C₃H₇ | CH₃ |
| Cl | (2-) Cl | C₃H₇-i | CH₃ |
| Cl | (2-) Cl | C₄H₉ | CH₃ |
| Cl | (2-) Cl | C₄H₉-i | CH₃ |
| Cl | (2-) Cl | C₄H₉-s | CH₃ |
| Cl | (2-) Cl | C₄H₉-t | CH₃ |
| Cl | (2-) Cl | cyclopropyl | CH₃ |
| Cl | (2-) Cl | cyclopropylmethyl | CH₃ |
| Cl | (2-) Cl | CH=CHCH₃ | CH₃ |

Group 2

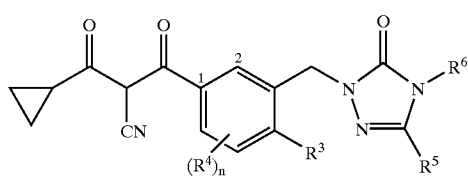

(IB-1)

R³, (R⁴)ₙ, R⁵ and R⁶ have, for example, the meanings given in the table below:

-continued

| $R^3$ | (position-)$(R^4)_n$ | $R^5$ | $R^6$ |
|---|---|---|---|
| Cl | (2-) Cl | phenyl-CH₂– (benzyl) | CH₃ |
| Cl | (2-) Cl | 4-Cl-phenyl-CH₂– | CH₃ |
| Cl | (2-) Cl | phenyl-CH₂CH₂– | CH₃ |
| Cl | (2-) Cl | N(CH₃)₂ | CH₃ |
| Cl | (2-) Cl | N-methylmorpholine | CH₃ |
| Cl | (2-) Cl | Cl | CH₃ |
| Cl | (2-) Cl | Br | CH₃ |
| SO₂CH₃ | (2-) Cl | CF₃ | CH₃ |
| SO₂CH₃ | (2-) Cl | SCH₃ | CH₃ |
| SO₂CH₃ | (2-) Cl | SC₂H₅ | CH₃ |
| SO₂CH₃ | (2-) Cl | SC₃H₇ | CH₃ |
| SO₂CH₃ | (2-) Cl | SC₃H₇-i | CH₃ |
| SO₂CH₃ | (2-) Cl | SCH₂CH=CH₂ | CH₃ |
| SO₂CH₃ | (2-) Cl | SCH₂C≡CH | CH₃ |
| SO₂CH₃ | (2-) Cl | SCH=CHCH₃ | CH₃ |
| SO₂CH₃ | (2-) Cl | SC≡CCH₃ | CH₃ |
| SO₂CH₃ | (2-) Cl | S-CH₂-cyclopropyl | CH₃ |
| SO₂CH₃ | (2-) Cl | SCH=C=CH₂ | CH₃ |
| SO₂CH₃ | (2-) Cl | SCH₂CN | CH₃ |
| SO₂CH₃ | (2-) Cl | SCH₂CH₂CN | CH₃ |
| SO₂CH₃ | (2-) Cl | OCH₃ | CH₃ |
| SO₂CH₃ | (2-) Cl | OC₂H₅ | CH₃ |
| SO₂CH₃ | (2-) Cl | OC₃H₇ | CH₃ |
| SO₂CH₃ | (2-) Cl | OC₃H₇-i | CH₃ |
| SO₂CH₃ | (2-) Cl | OC₄H₉ | CH₃ |
| SO₂CH₃ | (2-) Cl | OCH₂CF₃ | CH₃ |
| SO₂CH₃ | (2-) Cl | O-CH₂-cyclopropyl | CH₃ |
| SO₂CH₃ | (2-) Cl | OC₆H₅ | CH₃ |
| SO₂CH₃ | (2-) Cl | H | CH₃ |
| SO₂CH₃ | (2-) Cl | CH₃ | CH₃ |
| SO₂CH₃ | (2-) Cl | C₂H₅ | CH₃ |
| SO₂CH₃ | (2-) Cl | C₃H₇ | CH₃ |
| SO₂CH₃ | (2-) Cl | C₃H₇-i | CH₃ |
| SO₂CH₃ | (2-) Cl | C₄H₉ | CH₃ |
| SO₂CH₃ | (2-) Cl | C₄H₉-i | CH₃ |
| SO₂CH₃ | (2-) Cl | C₄H₉-s | CH₃ |
| SO₂CH₃ | (2-) Cl | C₄H₉-t | CH₃ |
| SO₂CH₃ | (2-) Cl | cyclopropyl-CH₂– | CH₃ |
| SO₂CH₃ | (2-) Cl | cyclopropyl-CH₂CH₂– | CH₃ |
| SO₂CH₃ | (2-) Cl | CH=CHCH₃ | CH₃ |
| SO₂CH₃ | (2-) Cl | phenyl-CH₂– | CH₃ |
| SO₂CH₃ | (2-) Cl | 4-Cl-phenyl-CH₂– | CH₃ |
| SO₂CH₃ | (2-) Cl | phenyl-CH₂CH₂– | CH₃ |
| SO₂CH₃ | (2-) Cl | N(CH₃)₂ | CH₃ |
| SO₂CH₃ | (2-) Cl | N-methylmorpholine | CH₃ |
| SO₂CH₃ | (2-) Cl | Cl | CH₃ |
| SO₂CH₃ | (2-) Cl | Br | CH₃ |
| Cl | (2-) SO₂CH₃ | CF₃ | CH₃ |
| Cl | (2-) SO₂CH₃ | SCH₃ | CH₃ |
| Cl | (2-) SO₂CH₃ | SC₂H₅ | CH₃ |
| Cl | (2-) SO₂CH₃ | SC₃H₇ | CH₃ |
| Cl | (2-) SO₂CH₃ | SC₃H₇-i | CH₃ |
| Cl | (2-) SO₂CH₃ | SCH₂CH=CH₂ | CH₃ |
| Cl | (2-) SO₂CH₃ | SCH₂C≡CH | CH₃ |

-continued

| R³ | (position-)(R⁴)ₙ | R⁵ | R⁶ |
|---|---|---|---|
| Cl | (2-) SO₂CH₃ | CH₃-CH=CH-S- | CH₃ |
| Cl | (2-) SO₂CH₃ | CH₃-C≡C-S- | CH₃ |
| Cl | (2-) SO₂CH₃ | cyclopropyl-CH₂-S- | CH₃ |
| Cl | (2-) SO₂CH₃ | SCH=C=CH₂ | CH₃ |
| Cl | (2-) SO₂CH₃ | SCH₂CN | CH₃ |
| Cl | (2-) SO₂CH₃ | SCH₂CH₂CN | CH₃ |
| Cl | (2-) SO₂CH₃ | OCH₃ | CH₃ |
| Cl | (2-) SO₂CH₃ | OC₂H₅ | CH₃ |
| Cl | (2-) SO₂CH₃ | OC₃H₇ | CH₃ |
| Cl | (2-) SO₂CH₃ | OC₃H₇-i | CH₃ |
| Cl | (2-) SO₂CH₃ | OC₄H₉ | CH₃ |
| Cl | (2-) SO₂CH₃ | OCH₂CF₃ | CH₃ |
| Cl | (2-) SO₂CH₃ | cyclopropyl-CH₂-O- | CH₃ |
| Cl | (2-) SO₂CH₃ | OC₆H₅ | CH₃ |
| Cl | (2-) SO₂CH₃ | H | CH₃ |
| Cl | (2-) SO₂CH₃ | CH₃ | CH₃ |
| Cl | (2-) SO₂CH₃ | C₂H₅ | CH₃ |
| Cl | (2-) SO₂CH₃ | C₃H₇ | CH₃ |
| Cl | (2-) SO₂CH₃ | C₃H₇-i | CH₃ |
| Cl | (2-) SO₂CH₃ | C₄H₉ | CH₃ |
| Cl | (2-) SO₂CH₃ | C₄H₉-i | CH₃ |
| Cl | (2-) SO₂CH₃ | C₄H₉-s | CH₃ |
| Cl | (2-) SO₂CH₃ | C₄H₉-t | CH₃ |
| Cl | (2-) SO₂CH₃ | cyclopropyl | CH₃ |
| Cl | (2-) SO₂CH₃ | cyclopropyl-CH₂- | CH₃ |
| Cl | (2-) SO₂CH₃ | CH=CHCH₃ | CH₃ |
| Cl | (2-) SO₂CH₃ | phenyl | CH₃ |
| Cl | (2-) SO₂CH₃ | 4-Cl-phenyl | CH₃ |
| Cl | (2-) SO₂CH₃ | benzyl | CH₃ |
| Cl | (2-) SO₂CH₃ | N(CH₃)₂ | CH₃ |
| Cl | (2-) SO₂CH₃ | N-morpholinyl | CH₃ |
| Cl | (2-) SO₂CH₃ | Cl | CH₃ |
| Cl | (2-) SO₂CH₃ | Br | CH₃ |
| Cl | (2-) Cl | CF₃ | cyclopropyl |
| Cl | (2-) Cl | SCH₃ | cyclopropyl |
| Cl | (2-) Cl | SC₂H₅ | cyclopropyl |
| Cl | (2-) Cl | SC₃H₇ | cyclopropyl |
| Cl | (2-) Cl | SC₃H₇-i | cyclopropyl |
| Cl | (2-) Cl | CH₂=CH-CH₂-S- | cyclopropyl |
| Cl | (2-) Cl | HC≡C-CH₂-S- | cyclopropyl |
| Cl | (2-) Cl | CH₃-CH=CH-S- | cyclopropyl |
| Cl | (2-) Cl | CH₃-C≡C-S- | cyclopropyl |
| Cl | (2-) Cl | cyclopropyl-CH₂-S- | cyclopropyl |
| Cl | (2-) Cl | SCH=C=CH₂ | cyclopropyl |
| Cl | (2-) Cl | SCH₂CN | cyclopropyl |
| Cl | (2-) Cl | SCH₂CH₂CN | cyclopropyl |

-continued

| $R^3$ | (position-)$(R^4)_n$ | $R^5$ | $R^6$ |
|---|---|---|---|
| Cl | (2-) Cl | OCH$_3$ | cyclopropyl |
| Cl | (2-) Cl | OC$_2$H$_5$ | cyclopropyl |
| Cl | (2-) Cl | OC$_3$H$_7$ | cyclopropyl |
| Cl | (2-) Cl | OC$_3$H$_7$-i | cyclopropyl |
| Cl | (2-) Cl | OC$_4$H$_9$ | cyclopropyl |
| Cl | (2-) Cl | OCH$_2$CF$_3$ | cyclopropyl |
| Cl | (2-) Cl | cyclopropylmethoxy | cyclopropyl |
| Cl | (2-) Cl | OC$_6$H$_5$ | cyclopropyl |
| Cl | (2-) Cl | H | cyclopropyl |
| Cl | (2-) Cl | CH$_3$ | cyclopropyl |
| Cl | (2-) Cl | C$_2$H$_5$ | cyclopropyl |
| Cl | (2-) Cl | C$_3$H$_7$ | cyclopropyl |
| Cl | (2-) Cl | C$_3$H$_7$-i | cyclopropyl |
| Cl | (2-) Cl | C$_4$H$_9$ | cyclopropyl |
| Cl | (2-) Cl | C$_4$H$_9$-i | cyclopropyl |
| Cl | (2-) Cl | C$_4$H$_9$-s | cyclopropyl |
| Cl | (2-) Cl | C$_4$H$_9$-t | cyclopropyl |

-continued

| $R^3$ | (position-)$(R^4)_n$ | $R^5$ | $R^6$ |
|---|---|---|---|
| Cl | (2-) Cl | cyclopropyl | cyclopropyl |
| Cl | (2-) Cl | cyclopropylmethyl | cyclopropyl |
| Cl | (2-) Cl | CH=CHCH$_3$ | cyclopropyl |
| Cl | (2-) Cl | phenyl | cyclopropyl |
| Cl | (2-) Cl | 4-chlorophenyl | cyclopropyl |
| Cl | (2-) Cl | benzyl | cyclopropyl |
| Cl | (2-) Cl | N(CH$_3$)$_2$ | cyclopropyl |
| Cl | (2-) Cl | morpholinyl | cyclopropyl |
| Cl | (2-) Cl | Cl | cyclopropyl |
| Cl | (2-) Cl | Br | cyclopropyl |
| SO$_2$CH$_3$ | (2-) Cl | CF$_3$ | cyclopropyl |
| SO$_2$CH$_3$ | (2-) Cl | SCH$_3$ | cyclopropyl |
| SO$_2$CH$_3$ | (2-) Cl | SC$_2$H$_5$ | cyclopropyl |
| SO$_2$CH$_3$ | (2-) Cl | SC$_3$H$_7$ | cyclopropyl |
| SO$_2$CH$_3$ | (2-) Cl | SC$_3$H$_7$-i | cyclopropyl |
| SO$_2$CH$_3$ | (2-) Cl | allylthiomethyl | cyclopropyl |

-continued

| R³ | (position-)(R⁴)ₙ | R⁵ | R⁶ |
|---|---|---|---|
| SO₂CH₃ | (2-) Cl |  |  |
| SO₂CH₃ | (2-) Cl |  | 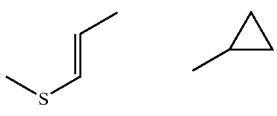 |
| SO₂CH₃ | (2-) Cl |  |  |
| SO₂CH₃ | (2-) Cl |  |  |
| SO₂CH₃ | (2-) Cl | SCH=C=CH₂ |  |
| SO₂CH₃ | (2-) Cl | SCH₂CN |  |
| SO₂CH₃ | (2-) Cl | SCH₂CH₂CN |  |
| SO₂CH₃ | (2-) Cl | OCH₃ |  |
| SO₂CH₃ | (2-) Cl | OC₂H₅ |  |
| SO₂CH₃ | (2-) Cl | OC₃H₇ |  |
| SO₂CH₃ | (2-) Cl | OC₃H₇-i |  |
| SO₂CH₃ | (2-) Cl | OC₄H₉ |  |
| SO₂CH₃ | (2-) Cl | OCH₂CF₃ |  |
| SO₂CH₃ | (2-) Cl |  |  |
| SO₂CH₃ | (2-) Cl | OC₆H₅ |  |

-continued

| R³ | (position-)(R⁴)ₙ | R⁵ | R⁶ |
|---|---|---|---|
| SO₂CH₃ | (2-) Cl | H |  |
| SO₂CH₃ | (2-) Cl | CH₃ |  |
| SO₂CH₃ | (2-) Cl | C₂H₅ |  |
| SO₂CH₃ | (2-) Cl | C₃H₇ |  |
| SO₂CH₃ | (2-) Cl | C₃H₇-i |  |
| SO₂CH₃ | (2-) Cl | C₄H₉ |  |
| SO₂CH₃ | (2-) Cl | C₄H₉-i |  |
| SO₂CH₃ | (2-) Cl | C₄H₉-s |  |
| SO₂CH₃ | (2-) Cl | C₄H₉-t |  |
| SO₂CH₃ | (2-) Cl |  | 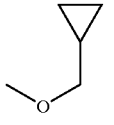 |
| SO₂CH₃ | (2-) Cl |  | |
| SO₂CH₃ | (2-) Cl | CH=CHCH₃ | |
| SO₂CH₃ | (2-) Cl |  | |
| SO₂CH₃ | (2-) Cl |  | |
| SO₂CH₃ | (2-) Cl |  | |
| SO₂CH₃ | (2-) Cl | N(CH₃)₂ |  |

-continued

| R³ | (position-)(R⁴)ₙ | R⁵ | R⁶ |
|---|---|---|---|
| SO₂CH₃ | (2-) Cl | N-methylmorpholino | cyclopropyl |
| SO₂CH₃ | (2-) Cl | Cl | cyclopropyl |
| SO₂CH₃ | (2-) Cl | Br | cyclopropyl |
| Cl | (2-) SO₂CH₃ | CF₃ | cyclopropyl |
| Cl | (2-) SO₂CH₃ | SCH₃ | cyclopropyl |
| Cl | (2-) SO₂CH₃ | SC₂H₅ | cyclopropyl |
| Cl | (2-) SO₂CH₃ | SC₃H₇ | cyclopropyl |
| Cl | (2-) SO₂CH₃ | SC₃H₇-i | cyclopropyl |
| Cl | (2-) SO₂CH₃ | SCH₂CH=CH₂ | cyclopropyl |
| Cl | (2-) SO₂CH₃ | SCH₂C≡CH | cyclopropyl |
| Cl | (2-) SO₂CH₃ | SCH=CHCH₃ | cyclopropyl |
| Cl | (2-) SO₂CH₃ | SC≡CCH₃ | cyclopropyl |
| Cl | (2-) SO₂CH₃ | SCH₂-cyclopropyl | cyclopropyl |
| Cl | (2-) SO₂CH₃ | SCH=C=CH₂ | cyclopropyl |
| Cl | (2-) SO₂CH₃ | SCH₂CN | cyclopropyl |

-continued

| R³ | (position-)(R⁴)ₙ | R⁵ | R⁶ |
|---|---|---|---|
| Cl | (2-) SO₂CH₃ | SCH₂CH₂CN | cyclopropyl |
| Cl | (2-) SO₂CH₃ | OCH₃ | cyclopropyl |
| Cl | (2-) SO₂CH₃ | OC₂H₅ | cyclopropyl |
| Cl | (2-) SO₂CH₃ | OC₃H₇ | cyclopropyl |
| Cl | (2-) SO₂CH₃ | OC₃H₇-i | cyclopropyl |
| Cl | (2-) SO₂CH₃ | OC₄H₉ | cyclopropyl |
| Cl | (2-) SO₂CH₃ | OCH₂CF₃ | cyclopropyl |
| Cl | (2-) SO₂CH₃ | OCH₂-cyclopropyl via OCH₂ | cyclopropyl |
| Cl | (2-) SO₂CH₃ | OC₆H₅ | cyclopropyl |
| Cl | (2-) SO₂CH₃ | H | cyclopropyl |
| Cl | (2-) SO₂CH₃ | CH₃ | cyclopropyl |
| Cl | (2-) SO₂CH₃ | C₂H₅ | cyclopropyl |
| Cl | (2-) SO₂CH₃ | C₃H₇ | cyclopropyl |
| Cl | (2-) SO₂CH₃ | C₃H₇-i | cyclopropyl |
| Cl | (2-) SO₂CH₃ | C₄H₉ | cyclopropyl |
| Cl | (2-) SO₂CH₃ | C₄H₉-i | cyclopropyl |
| Cl | (2-) SO₂CH₃ | C₄H₉-s | cyclopropyl |

| R³ | (position-)(R⁴)ₙ | R⁵ | R⁶ |
|---|---|---|---|
| Cl | (2-) SO₂CH₃ | C₄H₉-t |  |
| Cl | (2-) SO₂CH₃ |  |  |
| Cl | (2-) SO₂CH₃ |  |  |
| Cl | (2-) SO₂CH₃ | CH=CHCH₃ |  |
| Cl | (2-) SO₂CH₃ |  |  |
| Cl | (2-) SO₂CH₃ |  |  |
| Cl | (2-) SO₂CH₃ |  |  |
| Cl | (2-) SO₂CH₃ | N(CH₃)₂ |  |
| Cl | (2-) SO₂CH₃ |  |  |
| Cl | (2-) SO₂CH₃ | Cl |  |
| Cl | (2-) SO₂CH₃ | Br |  |
| Cl | (2-) Cl | CF₃ | N(CH₃)₂ |
| Cl | (2-) Cl | SCH₃ | N(CH₃)₂ |
| Cl | (2-) Cl | SC₂H₅ | N(CH₃)₂ |
| Cl | (2-) Cl | SC₃H₇ | N(CH₃)₂ |
| Cl | (2-) Cl | SC₃H₇-i | N(CH₃)₂ |
| Cl | (2-) Cl |  | N(CH₃)₂ |
| Cl | (2-) Cl |  | N(CH₃)₂ |
| Cl | (2-) Cl |  | N(CH₃)₂ |
| Cl | (2-) Cl |  | N(CH₃)₂ |
| Cl | (2-) Cl |  | N(CH₃)₂ |
| Cl | (2-) Cl | SCH=C=CH₂ | N(CH₃)₂ |
| Cl | (2-) Cl | SCH₂CN | N(CH₃)₂ |
| Cl | (2-) Cl | SCH₂CH₂CN | N(CH₃)₂ |
| Cl | (2-) Cl | OCH₃ | N(CH₃)₂ |
| Cl | (2-) Cl | OC₂H₅ | N(CH₃)₂ |
| Cl | (2-) Cl | OC₃H₇ | N(CH₃)₂ |
| Cl | (2-) Cl | OC₃H₇-i | N(CH₃)₂ |
| Cl | (2-) Cl | OC₄H₉ | N(CH₃)₂ |
| Cl | (2-) Cl | OCH₂CF₃ | N(CH₃)₂ |
| Cl | (2-) Cl |  | N(CH₃)₂ |
| Cl | (2-) Cl | OC₆H₅ | N(CH₃)₂ |
| Cl | (2-) Cl | H | N(CH₃)₂ |
| Cl | (2-) Cl | CH₃ | N(CH₃)₂ |
| Cl | (2-) Cl | C₂H₅ | N(CH₃)₂ |
| Cl | (2-) Cl | C₃H₇ | N(CH₃)₂ |
| Cl | (2-) Cl | C₃H₇-i | N(CH₃)₂ |
| Cl | (2-) Cl | C₄H₉ | N(CH₃)₂ |
| Cl | (2-) Cl | C₄H₉-i | N(CH₃)₂ |
| Cl | (2-) Cl | C₄H₉-s | N(CH₃)₂ |
| Cl | (2-) Cl | C₄H₉-t | N(CH₃)₂ |
| Cl | (2-) Cl |  | N(CH₃)₂ |
| Cl | (2-) Cl |  | N(CH₃)₂ |
| Cl | (2-) Cl | CH=CHCH₃ | N(CH₃)₂ |
| Cl | (2-) Cl |  | N(CH₃)₂ |
| Cl | (2-) Cl |  | N(CH₃)₂ |
| Cl | (2-) Cl |  | N(CH₃)₂ |
| Cl | (2-) Cl | N(CH₃)₂ | N(CH₃)₂ |
| Cl | (2-) Cl |  | N(CH₃)₂ |

-continued

| $R^3$ | (position-)$(R^4)_n$ | $R^5$ | $R^6$ |
|---|---|---|---|
| Cl | (2-) Cl | Cl | $N(CH_3)_2$ |
| Cl | (2-) Cl | Br | $N(CH_3)_2$ |
| $SO_2CH_3$ | (2-) Cl | $CF_3$ | $N(CH_3)_2$ |
| $SO_2CH_3$ | (2-) Cl | $SCH_3$ | $N(CH_3)_2$ |
| $SO_2CH_3$ | (2-) Cl | $SC_2H_5$ | $N(CH_3)_2$ |
| $SO_2CH_3$ | (2-) Cl | $SC_3H_7$ | $N(CH_3)_2$ |
| $SO_2CH_3$ | (2-) Cl | $SC_3H_7$-i | $N(CH_3)_2$ |
| $SO_2CH_3$ | (2-) Cl | allyl-S-CH_2 | $N(CH_3)_2$ |
| $SO_2CH_3$ | (2-) Cl | propargyl-S-CH_2 | $N(CH_3)_2$ |
| $SO_2CH_3$ | (2-) Cl | CH_3CH=CH-S- | $N(CH_3)_2$ |
| $SO_2CH_3$ | (2-) Cl | CH_3C≡C-S- | $N(CH_3)_2$ |
| $SO_2CH_3$ | (2-) Cl | cyclopropyl-CH_2-S- | $N(CH_3)_2$ |
| $SO_2CH_3$ | (2-) Cl | $SCH=C=CH_2$ | $N(CH_3)_2$ |
| $SO_2CH_3$ | (2-) Cl | $SCH_2CN$ | $N(CH_3)_2$ |
| $SO_2CH_3$ | (2-) Cl | $SCH_2CH_2CN$ | $N(CH_3)_2$ |
| $SO_2CH_3$ | (2-) Cl | $OCH_3$ | $N(CH_3)_2$ |
| $SO_2CH_3$ | (2-) Cl | $OC_2H_5$ | $N(CH_3)_2$ |
| $SO_2CH_3$ | (2-) Cl | $OC_3H_7$ | $N(CH_3)_2$ |
| $SO_2CH_3$ | (2-) Cl | $OC_3H_7$-i | $N(CH_3)_2$ |
| $SO_2CH_3$ | (2-) Cl | $OC_4H_9$ | $N(CH_3)_2$ |
| $SO_2CH_3$ | (2-) Cl | $OCH_2CF_3$ | $N(CH_3)_2$ |
| $SO_2CH_3$ | (2-) Cl | cyclopropyl-CH_2-O- | $N(CH_3)_2$ |
| $SO_2CH_3$ | (2-) Cl | $OC_6H_5$ | $N(CH_3)_2$ |
| $SO_2CH_3$ | (2-) Cl | H | $N(CH_3)_2$ |
| $SO_2CH_3$ | (2-) Cl | $CH_3$ | $N(CH_3)_2$ |
| $SO_2CH_3$ | (2-) Cl | $C_2H_5$ | $N(CH_3)_2$ |
| $SO_2CH_3$ | (2-) Cl | $C_3H_7$ | $N(CH_3)_2$ |
| $SO_2CH_3$ | (2-) Cl | $C_3H_7$-i | $N(CH_3)_2$ |
| $SO_2CH_3$ | (2-) Cl | $C_4H_9$ | $N(CH_3)_2$ |
| $SO_2CH_3$ | (2-) Cl | $C_4H_9$-i | $N(CH_3)_2$ |
| $SO_2CH_3$ | (2-) Cl | $C_4H_9$-s | $N(CH_3)_2$ |
| $SO_2CH_3$ | (2-) Cl | $C_4H_9$-t | $N(CH_3)_2$ |
| $SO_2CH_3$ | (2-) Cl | cyclopropyl | $N(CH_3)_2$ |
| $SO_2CH_3$ | (2-) Cl | cyclopropyl-CH_2- | $N(CH_3)_2$ |
| $SO_2CH_3$ | (2-) Cl | $CH=CHCH_3$ | $N(CH_3)_2$ |
| $SO_2CH_3$ | (2-) Cl | 4-methylphenyl | $N(CH_3)_2$ |
| $SO_2CH_3$ | (2-) Cl | 4-chloro-2-methylphenyl | $N(CH_3)_2$ |
| $SO_2CH_3$ | (2-) Cl | benzyl-CH_2 | $N(CH_3)_2$ |
| $SO_2CH_3$ | (2-) Cl | $N(CH_3)_2$ | $N(CH_3)_2$ |
| $SO_2CH_3$ | (2-) Cl | 4-methylmorpholino | $N(CH_3)_2$ |
| $SO_2CH_3$ | (2-) Cl | Cl | $N(CH_3)_2$ |
| $SO_2CH_3$ | (2-) Cl | Br | $N(CH_3)_2$ |
| Cl | (2-) $SO_2CH_3$ | $CF_3$ | $N(CH_3)_2$ |
| Cl | (2-) $SO_2CH_3$ | $SCH_3$ | $N(CH_3)_2$ |
| Cl | (2-) $SO_2CH_3$ | $SC_2H_5$ | $N(CH_3)_2$ |
| Cl | (2-) $SO_2CH_3$ | $SC_3H_7$ | $N(CH_3)_2$ |
| Cl | (2-) $SO_2CH_3$ | $SC_3H_7$-i | $N(CH_3)_2$ |
| Cl | (2-) $SO_2CH_3$ | allyl-S-CH_2 | $N(CH_3)_2$ |
| Cl | (2-) $SO_2CH_3$ | propargyl-S-CH_2 | $N(CH_3)_2$ |
| Cl | (2-) $SO_2CH_3$ | CH_3CH=CH-S- | $N(CH_3)_2$ |
| Cl | (2-) $SO_2CH_3$ | CH_3C≡C-S- | $N(CH_3)_2$ |
| Cl | (2-) $SO_2CH_3$ | cyclopropyl-CH_2-S- | $N(CH_3)_2$ |
| Cl | (2-) $SO_2CH_3$ | $SCH=C=CH_2$ | $N(CH_3)_2$ |
| Cl | (2-) $SO_2CH_3$ | $SCH_2CN$ | $N(CH_3)_2$ |
| Cl | (2-) $SO_2CH_3$ | $SCH_2CH_2CN$ | $N(CH_3)_2$ |
| Cl | (2-) $SO_2CH_3$ | $OCH_3$ | $N(CH_3)_2$ |
| Cl | (2-) $SO_2CH_3$ | $OC_2H_5$ | $N(CH_3)_2$ |
| Cl | (2-) $SO_2CH_3$ | $OC_3H_7$ | $N(CH_3)_2$ |
| Cl | (2-) $SO_2CH_3$ | $OC_3H_7$-i | $N(CH_3)_2$ |
| Cl | (2-) $SO_2CH_3$ | $OC_4H_9$ | $N(CH_3)_2$ |
| Cl | (2-) $SO_2CH_3$ | $OCH_2CF_3$ | $N(CH_3)_2$ |

-continued

| R³ | (position-)(R⁴)ₙ | R⁵ | R⁶ |
|---|---|---|---|
| Cl | (2-) SO₂CH₃ |  | N(CH₃)₂ |
| Cl | (2-) SO₂CH₃ | OC₆H₅ | N(CH₃)₂ |
| Cl | (2-) SO₂CH₃ | H | N(CH₃)₂ |
| Cl | (2-) SO₂CH₃ | CH₃ | N(CH₃)₂ |
| Cl | (2-) SO₂CH₃ | C₂H₅ | N(CH₃)₂ |
| Cl | (2-) SO₂CH₃ | C₃H₇ | N(CH₃)₂ |
| Cl | (2-) SO₂CH₃ | C₃H₇-i | N(CH₃)₂ |
| Cl | (2-) SO₂CH₃ | C₄H₉ | N(CH₃)₂ |
| Cl | (2-) SO₂CH₃ | C₄H₉-i | N(CH₃)₂ |
| Cl | (2-) SO₂CH₃ | C₄H₉-s | N(CH₃)₂ |
| Cl | (2-) SO₂CH₃ | C₄H₉-t | N(CH₃)₂ |
| Cl | (2-) SO₂CH₃ |  | N(CH₃)₂ |
| Cl | (2-) SO₂CH₃ |  | N(CH₃)₂ |
| Cl | (2-) SO₂CH₃ | CH=CHCH₃ | N(CH₃)₂ |
| Cl | (2-) SO₂CH₃ |  | N(CH₃)₂ |
| Cl | (2-) SO₂CH₃ |  | N(CH₃)₂ |
| Cl | (2-) SO₂CH₃ |  | N(CH₃)₂ |
| Cl | (2-) SO₂CH₃ | N(CH₃)₂ | N(CH₃)₂ |
| Cl | (2-) SO₂CH₃ |  | N(CH₃)₂ |
| Cl | (2-) SO₂CH₃ | Cl | N(CH₃)₂ |
| Cl | (2-) SO₂CH₃ | Br | N(CH₃)₂ |
| Cl | (2-) Cl | CH₃ | OCH₃ |
| Cl | (2-) Cl | C₂H₅ | OCH₃ |
| Cl | (2-) Cl | C₃H₇ | OCH₃ |
| Cl | (2-) Cl | SCH₃ | OCH₃ |
| Cl | (2-) Cl | SC₂H₅ | OCH₃ |
| Cl | (2-) Cl | OCH₃ | OCH₃ |
| Cl | (2-) Cl | OC₂H₅ | OCH₃ |
| Cl | (2-) Cl | CH₃ | OC₂H₅ |
| Cl | (2-) Cl | C₂H₅ | OC₂H₅ |
| Cl | (2-) Cl | C₃H₇ | OC₂H₅ |
| Cl | (2-) Cl | SCH₃ | OC₂H₅ |
| Cl | (2-) Cl | SC₂H₅ | OC₂H₅ |
| Cl | (2-) Cl | OCH₃ | OC₂H₅ |
| Cl | (2-) Cl | OC₂H₅ | OC₂H₅ |
| Cl | (2-) SO₂CH₃ | CH₃ | OCH₃ |
| Cl | (2-) SO₂CH₃ | C₂H₅ | OCH₃ |
| Cl | (2-) SO₂CH₃ | C₃H₇ | OCH₃ |
| Cl | (2-) SO₂CH₃ | SCH₃ | OCH₃ |
| Cl | (2-) SO₂CH₃ | SC₂H₅ | OCH₃ |
| Cl | (2-) SO₂CH₃ | OCH₃ | OCH₃ |
| Cl | (2-) SO₂CH₃ | OC₂H₅ | OCH₃ |
| Cl | (2-) SO₂CH₃ | CH₃ | OC₂H₅ |
| Cl | (2-) SO₂CH₃ | C₂H₅ | OC₂H₅ |
| Cl | (2-) SO₂CH₃ | C₃H₇ | OC₂H₅ |
| Cl | (2-) SO₂CH₃ | SCH₃ | OC₂H₅ |
| Cl | (2-) SO₂CH₃ | SC₂H₅ | OC₂H₅ |
| Cl | (2-) SO₂CH₃ | OCH₃ | OC₂H₅ |
| Cl | (2-) SO₂CH₃ | OC₂H₅ | OC₂H₅ |
| SO₂CH₃ | (2-) Cl | Cl | OCH₃ |
| SO₂CH₃ | (2-) Cl | Br | OCH₃ |
| SO₂CH₃ | (2-) Cl | CH₃ | OCH₃ |
| SO₂CH₃ | (2-) Cl | C₂H₅ | OCH₃ |
| SO₂CH₃ | (2-) Cl | C₃H₇ | OCH₃ |
| SO₂CH₃ | (2-) Cl | SCH₃ | OCH₃ |
| SO₂CH₃ | (2-) Cl | SC₂H₅ | OCH₃ |
| SO₂CH₃ | (2-) Cl | OCH₃ | OC₂H₅ |
| SO₂CH₃ | (2-) Cl | OC₂H₅ | OC₂H₅ |
| SO₂CH₃ | (2-) Cl | CH₃ | OC₂H₅ |
| SO₂CH₃ | (2-) Cl | C₂H₅ | OC₂H₅ |
| SO₂CH₃ | (2-) Cl | C₃H₇ | OC₂H₅ |
| SO₂CH₃ | (2-) Cl | SCH₃ | OC₂H₅ |
| SO₂CH₃ | (2-) Cl | SC₂H₅ | OC₂H₅ |
| SO₂CH₃ | (2-) Cl | OCH₃ | OC₂H₅ |
| CF₃ | (2-) Cl | Br | CH₃ |
| CF₃ | (2-) Cl | SCH₃ | CH₃ |
| CF₃ | (2-) Cl | OCH₃ | CH₃ |
| CF₃ | (2-) Cl | N(CH₃)₂ | CH₃ |
| CF₃ | (2-) Cl | CF₃ | CH₃ |
| CF₃ | (2-) NO₂ | Br | CH₃ |
| CF₃ | (2-) NO₂ | SCH₃ | CH₃ |
| CF₃ | (2-) NO₂ | OCH₃ | CH₃ |
| CF₃ | (2-) NO₂ | N(CH₃)₂ | CH₃ |
| CF₃ | (2-) NO₂ | CF₃ | CH₃ |
| CF₃ | (2-) CH₃ | Br | CH₃ |
| CF₃ | (2-) CH₃ | SCH₃ | CH₃ |
| CF₃ | (2-) CH₃ | OCH₃ | CH₃ |
| CF₃ | (2-) CH₃ | N(CH₃)₂ | CH₃ |
| CF₃ | (2-) CH₃ | CF₃ | CH₃ |
| CF₃ | (2-) OCH₃ | Br | CH₃ |
| CF₃ | (2-) OCH₃ | SCH₃ | CH₃ |
| CF₃ | (2-) OCH₃ | OCH₃ | CH₃ |
| CF₃ | (2-) OCH₃ | N(CH₃)₂ | CH₃ |
| CF₃ | (2-) OCH₃ | CF₃ | CH₃ |
| SO₂CH₃ | (2-) NO₂ | Br | CH₃ |
| SO₂CH₃ | (2-) NO₂ | SCH₃ | CH₃ |
| SO₂CH₃ | (2-) NO₂ | OCH₃ | CH₃ |
| SO₂CH₃ | (2-) NO₂ | N(CH₃)₂ | CH₃ |
| SO₂CH₃ | (2-) NO₂ | CF₃ | CH₃ |
| SO₂CH₃ | (2-) CF₃ | Br | CH₃ |
| SO₂CH₃ | (2-) CF₃ | SCH₃ | CH₃ |
| SO₂CH₃ | (2-) CF₃ | OCH₃ | CH₃ |
| SO₂CH₃ | (2-) CF₃ | N(CH₃)₂ | CH₃ |
| SO₂CH₃ | (2-) CF₃ | CF₃ | CH₃ |
| SO₂CH₃ | (2-) SO₂CH₃ | Br | CH₃ |
| SO₂CH₃ | (2-) SO₂CH₃ | SCH₃ | CH₃ |
| SO₂CH₃ | (2-) SO₂CH₃ | OCH₃ | CH₃ |
| SO₂CH₃ | (2-) SO₂CH₃ | N(CH₃)₂ | CH₃ |
| SO₂CH₃ | (2-) SO₂CH₃ | CF₃ | CH₃ |
| CN | (2-) Cl | Br | CH₃ |
| CN | (2-) Cl | SCH₃ | CH₃ |
| CN | (2-) Cl | OCH₃ | CH₃ |
| CN | (2-) Cl | N(CH₃)₂ | CH₃ |
| CN | (2-) Cl | CF₃ | CH₃ |
| CN | (2-) NO₂ | Br | CH₃ |
| CN | (2-) NO₂ | SCH₃ | CH₃ |
| CN | (2-) NO₂ | OCH₃ | CH₃ |
| CN | (2-) NO₂ | N(CH₃)₂ | CH₃ |
| CN | (2-) NO₂ | CF₃ | CH₃ |
| CN | (2-) CF₃ | Br | CH₃ |
| CN | (2-) CF₃ | SCH₃ | CH₃ |
| CN | (2-) CF₃ | OCH₃ | CH₃ |
| CN | (2-) CF₃ | N(CH₃)₂ | CH₃ |
| CN | (2-) CF₃ | CF₃ | CH₃ |
| CN | (2-) SO₂CH₃ | Br | CH₃ |
| CN | (2-) SO₂CH₃ | SCH₃ | CH₃ |
| CN | (2-) SO₂CH₃ | OCH₃ | CH₃ |
| CN | (2-) SO₂CH₃ | N(CH₃)₂ | CH₃ |

-continued

| R³ | (position-)(R⁴)ₙ | R⁵ | R⁶ |
|---|---|---|---|
| CN | (2-) SO₂CH₃ | CF₃ | CH₃ |
| Br | (2-) NO₂ | Br | CH₃ |
| Br | (2-) NO₂ | SCH₃ | CH₃ |
| Br | (2-) NO₂ | OCH₃ | CH₃ |
| Br | (2-) NO₂ | N(CH₃)₂ | CH₃ |
| Br | (2-) NO₂ | CF₃ | CH₃ |
| Br | (2-) CF₃ | Br | CH₃ |
| Br | (2-) CF₃ | SCH₃ | CH₃ |
| Br | (2-) CF₃ | OCH₃ | CH₃ |
| Br | (2-) CF₃ | N(CH₃)₂ | CH₃ |
| Br | (2-) CF₃ | CF₃ | CH₃ |
| Br | (2-) SO₂CH₃ | Br | CH₃ |
| Br | (2-) SO₂CH₃ | SCH₃ | CH₃ |
| Br | (2-) SO₂CH₃ | OCH₃ | CH₃ |
| Br | (2-) SO₂CH₃ | N(CH₃)₂ | CH₃ |
| Br | (2-) SO₂CH₃ | CF₃ | CH₃ |
| Br | (2-) CH₃ | Br | CH₃ |
| Br | (2-) CH₃ | SCH₃ | CH₃ |
| Br | (2-) CH₃ | OCH₃ | CH₃ |
| Br | (2-) CH₃ | N(CH₃)₂ | CH₃ |
| Br | (2-) CH₃ | CF₃ | CH₃ |
| Cl | (2-) OCH₃ | CF₃ | CH₃ |
| Cl | (2-) OCH₃ | SCH₃ | CH₃ |
| Cl | (2-) OCH₃ | SC₂H₅ | CH₃ |
| Cl | (2-) OCH₃ | SC₃H₇ | CH₃ |
| Cl | (2-) OCH₃ | SC₃H₇-i | CH₃ |
| Cl | (2-) OCH₃ | S-CH₂-CH=CH₂ | CH₃ |
| Cl | (2-) OCH₃ | S-CH₂-C≡CH | CH₃ |
| Cl | (2-) OCH₃ | S-CH=CH-CH₃ | CH₃ |
| Cl | (2-) OCH₃ | S-C≡C-CH₃ | CH₃ |
| Cl | (2-) OCH₃ | S-CH₂-(cyclopropyl) | CH₃ |
| Cl | (2-) OCH₃ | SCH=C=CH₂ | CH₃ |
| Cl | (2-) OCH₃ | SCH₂CN | CH₃ |
| Cl | (2-) OCH₃ | SCH₂CH₂CN | CH₃ |
| Cl | (2-) OCH₃ | OCH₃ | CH₃ |
| Cl | (2-) OCH₃ | OC₂H₅ | CH₃ |
| Cl | (2-) OCH₃ | OC₃H₇ | CH₃ |
| Cl | (2-) OCH₃ | OC₃H₇-i | CH₃ |
| Cl | (2-) OCH₃ | OC₄H₉ | CH₃ |
| Cl | (2-) OCH₃ | OCH₂CF₃ | CH₃ |
| Cl | (2-) OCH₃ | O-CH₂-(oxiranyl) | CH₃ |
| Cl | (2-) OCH₃ | OC₆H₅ | CH₃ |
| Cl | (2-) OCH₃ | H | CH₃ |
| Cl | (2-) OCH₃ | CH₃ | CH₃ |
| Cl | (2-) OCH₃ | C₂H₅ | CH₃ |
| Cl | (2-) OCH₃ | C₃H₇ | CH₃ |
| Cl | (2-) OCH₃ | C₃H₇-i | CH₃ |
| Cl | (2-) OCH₃ | C₄H₉ | CH₃ |
| Cl | (2-) OCH₃ | C₄H₉-i | CH₃ |
| Cl | (2-) OCH₃ | C₄H₉-s | CH₃ |
| Cl | (2-) OCH₃ | C₄H₉-t | CH₃ |
| Cl | (2-) OCH₃ | cyclopropyl-CH₂- | CH₃ |
| Cl | (2-) OCH₃ | cyclopropyl-CH₂-CH₂- | CH₃ |
| Cl | (2-) OCH₃ | CH=CHCH₃ | CH₃ |
| Cl | (2-) OCH₃ | phenyl-CH₂- | CH₃ |
| Cl | (2-) OCH₃ | 4-Cl-phenyl-CH₂- | CH₃ |
| Cl | (2-) OCH₃ | phenyl-CH₂-CH₂- | CH₃ |
| Cl | (2-) OCH₃ | N(CH₃)₂ | CH₃ |
| Cl | (2-) OCH₃ | morpholinyl-CH₂- | CH₃ |
| Cl | (2-) OCH₃ | Cl | CH₃ |
| Cl | (2-) OCH₃ | Br | CH₃ |
| SO₂CH₃ | (2-) OCH₃ | CF₃ | CH₃ |
| SO₂CH₃ | (2-) OCH₃ | SCH₃ | CH₃ |
| SO₂CH₃ | (2-) OCH₃ | SC₂H₅ | CH₃ |
| SO₂CH₃ | (2-) OCH₃ | SC₃H₇ | CH₃ |
| SO₂CH₃ | (2-) OCH₃ | SC₃H₇-i | CH₃ |
| SO₂CH₃ | (2-) OCH₃ | S-CH₂-CH=CH₂ | CH₃ |
| SO₂CH₃ | (2-) OCH₃ | S-CH₂-C≡CH | CH₃ |
| SO₂CH₃ | (2-) OCH₃ | S-CH=CH-CH₃ | CH₃ |

-continued

| R³ | (position-)(R⁴)ₙ | R⁵ | R⁶ |
|---|---|---|---|
| SO₂CH₃ | (2-) OCH₃ | 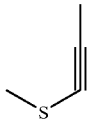 | CH₃ |
| SO₂CH₃ | (2-) OCH₃ | 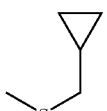 | CH₃ |
| SO₂CH₃ | (2-) OCH₃ | SCH=C=CH₂ | CH₃ |
| SO₂CH₃ | (2-) OCH₃ | SCH₂CN | CH₃ |
| SO₂CH₃ | (2-) OCH₃ | SCH₂CH₂CN | CH₃ |
| SO₂CH₃ | (2-) OCH₃ | OCH₃ | CH₃ |
| SO₂CH₃ | (2-) OCH₃ | OC₂H₅ | CH₃ |
| SO₂CH₃ | (2-) OCH₃ | OC₃H₇ | CH₃ |
| SO₂CH₃ | (2-) OCH₃ | OC₃H₇-i | CH₃ |
| SO₂CH₃ | (2-) OCH₃ | OC₄H₉ | CH₃ |
| SO₂CH₃ | (2-) OCH₃ | OCH₂CF₃ | CH₃ |
| SO₂CH₃ | (2-) OCH₃ |  | CH₃ |
| SO₂CH₃ | (2-) OCH₃ | OC₆H₅ | CH₃ |
| SO₂CH₃ | (2-) OCH₃ | H | CH₃ |
| SO₂CH₃ | (2-) OCH₃ | CH₃ | CH₃ |
| SO₂CH₃ | (2-) OCH₃ | C₂H₅ | CH₃ |
| SO₂CH₃ | (2-) OCH₃ | C₃H₇ | CH₃ |
| SO₂CH₃ | (2-) OCH₃ | C₃H₇-i | CH₃ |
| SO₂CH₃ | (2-) OCH₃ | C₄H₉ | CH₃ |
| SO₂CH₃ | (2-) OCH₃ | C₄H₉-i | CH₃ |
| SO₂CH₃ | (2-) OCH₃ | C₄H₉-s | CH₃ |
| SO₂CH₃ | (2-) OCH₃ | C₄H₉-t | CH₃ |
| SO₂CH₃ | (2-) OCH₃ | 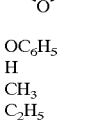 | CH₃ |
| SO₂CH₃ | (2-) OCH₃ |  | CH₃ |
| SO₂CH₃ | (2-) OCH₃ | CH=CHCH₃ | CH₃ |
| SO₂CH₃ | (2-) OCH₃ | 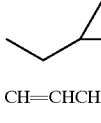 | CH₃ |
| SO₂CH₃ | (2-) OCH₃ | 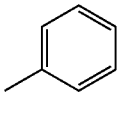 | CH₃ |
| SO₂CH₃ | (2-) OCH₃ | 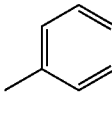 | CH₃ |
| SO₂CH₃ | (2-) OCH₃ | N(CH₃)₂ | CH₃ |
| SO₂CH₃ | (2-) OCH₃ | 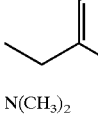 | CH₃ |

-continued

| R³ | (position-)(R⁴)ₙ | R⁵ | R⁶ |
|---|---|---|---|
| SO₂CH₃ | (2-) OCH₃ | Cl | CH₃ |
| SO₂CH₃ | (2-) OCH₃ | Br | CH₃ |
| Cl | (2-) OCH₃ | CF₃ | 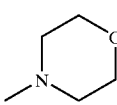 |
| Cl | (2-) OCH₃ | SCH₃ |  |
| Cl | (2-) OCH₃ | SC₂H₅ |  |
| Cl | (2-) OCH₃ | SC₃H₇ |  |
| Cl | (2-) OCH₃ | SC₃H₇-i | 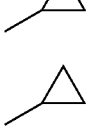 |
| Cl | (2-) OCH₃ |  |  |
| Cl | (2-) OCH₃ |  | 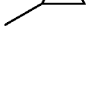 |
| Cl | (2-) OCH₃ |  |  |
| Cl | (2-) OCH₃ |  |  |
| Cl | (2-) OCH₃ |  | 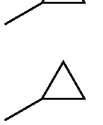 |
| Cl | (2-) OCH₃ | SCH=C=CH₂ |  |
| Cl | (2-) OCH₃ | SCH₂CN |  |
| Cl | (2-) OCH₃ | SCH₂CH₂CN | |
| Cl | (2-) OCH₃ | OCH₃ | |

-continued

| R³ | (position-)(R⁴)ₙ | R⁵ | R⁶ |
|---|---|---|---|
| Cl | (2-) OCH₃ | OC₂H₅ | 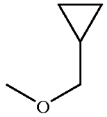 |
| Cl | (2-) OCH₃ | OC₃H₇ | 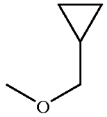 |
| Cl | (2-) OCH₃ | OC₃H₇-i | 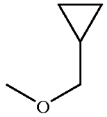 |
| Cl | (2-) OCH₃ | OC₄H₉ | 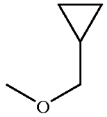 |
| Cl | (2-) OCH₃ | OCH₂CF₃ | 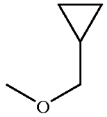 |
| Cl | (2-) OCH₃ |  | 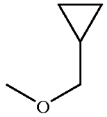 |
| Cl | (2-) OCH₃ | OC₆H₅ | 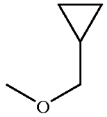 |
| Cl | (2-) OCH₃ | H | 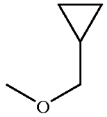 |
| Cl | (2-) OCH₃ | CH₃ | 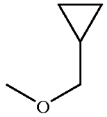 |
| Cl | (2-) OCH₃ | C₂H₅ | 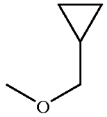 |
| Cl | (2-) OCH₃ | C₃H₇ | 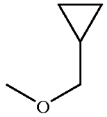 |
| Cl | (2-) OCH₃ | C₃H₇-i | 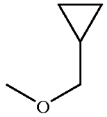 |
| Cl | (2-) OCH₃ | C₄H₉ | 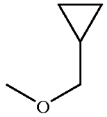 |
| Cl | (2-) OCH₃ | C₄H₉-i | 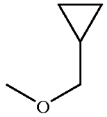 |
| Cl | (2-) OCH₃ | C₄H₉-s | 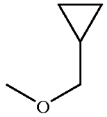 |
| Cl | (2-) OCH₃ | C₄H₉-t | 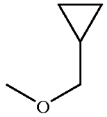 |
| Cl | (2-) OCH₃ | 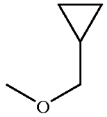 | 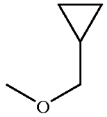 |

-continued

| R³ | (position-)(R⁴)ₙ | R⁵ | R⁶ |
|---|---|---|---|
| Cl | (2-) OCH₃ | 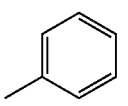 | 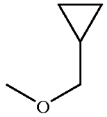 |
| Cl | (2-) OCH₃ | CH=CHCH₃ | 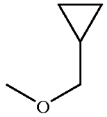 |
| Cl | (2-) OCH₃ | 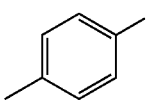 | 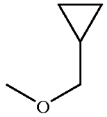 |
| Cl | (2-) OCH₃ | 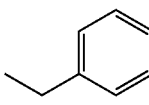 | 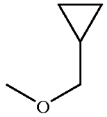 |
| Cl | (2-) OCH₃ | 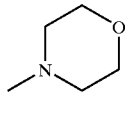 | 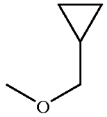 |
| Cl | (2-) OCH₃ | N(CH₃)₂ | 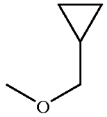 |
| Cl | (2-) OCH₃ | 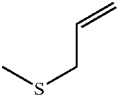 | 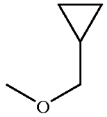 |
| Cl | (2-) OCH₃ | Cl | 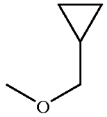 |
| Cl | (2-) OCH₃ | Br | 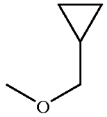 |
| SO₂CH₃ | (2-) OCH₃ | CF₃ | 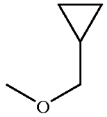 |
| SO₂CH₃ | (2-) OCH₃ | SCH₃ | 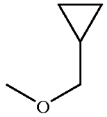 |
| SO₂CH₃ | (2-) OCH₃ | SC₂H₅ | 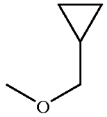 |
| SO₂CH₃ | (2-) OCH₃ | SC₃H₇ | 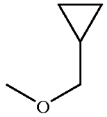 |
| SO₂CH₃ | (2-) OCH₃ | SC₃H₇-i | 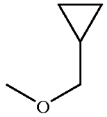 |
| SO₂CH₃ | (2-) OCH₃ |  | 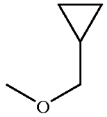 |

-continued

| $R^3$ | (position-)$(R^4)_n$ | $R^5$ | $R^6$ |
|---|---|---|---|
| SO₂CH₃ | (2-) OCH₃ | CH₂-C≡CH (via S) | cyclopropyl |
| SO₂CH₃ | (2-) OCH₃ | SCH=CHCH₃ | cyclopropyl |
| SO₂CH₃ | (2-) OCH₃ | S-C≡C-CH₃ | cyclopropyl |
| SO₂CH₃ | (2-) OCH₃ | S-CH₂-cyclopropyl | cyclopropyl |
| SO₂CH₃ | (2-) OCH₃ | SCH=C=CH₂ | cyclopropyl |
| SO₂CH₃ | (2-) OCH₃ | SCH₂CN | cyclopropyl |
| SO₂CH₃ | (2-) OCH₃ | SCH₂CH₂CN | cyclopropyl |
| SO₂CH₃ | (2-) OCH₃ | OCH₃ | cyclopropyl |
| SO₂CH₃ | (2-) OCH₃ | OC₂H₅ | cyclopropyl |
| SO₂CH₃ | (2-) OCH₃ | OC₃H₇ | cyclopropyl |
| SO₂CH₃ | (2-) OCH₃ | OC₃H₇-i | cyclopropyl |
| SO₂CH₃ | (2-) OCH₃ | OC₄H₉ | cyclopropyl |
| SO₂CH₃ | (2-) OCH₃ | OCH₂CF₃ | cyclopropyl |
| SO₂CH₃ | (2-) OCH₃ | OCH₂-cyclopropyl | cyclopropyl |
| SO₂CH₃ | (2-) OCH₃ | OC₆H₅ | cyclopropyl |
| SO₂CH₃ | (2-) OCH₃ | H | cyclopropyl |
| SO₂CH₃ | (2-) OCH₃ | CH₃ | cyclopropyl |
| SO₂CH₃ | (2-) OCH₃ | C₂H₅ | cyclopropyl |
| SO₂CH₃ | (2-) OCH₃ | C₃H₇ | cyclopropyl |
| SO₂CH₃ | (2-) OCH₃ | C₃H₇-i | cyclopropyl |
| SO₂CH₃ | (2-) OCH₃ | C₄H₉ | cyclopropyl |
| SO₂CH₃ | (2-) OCH₃ | C₄H₉-i | cyclopropyl |
| SO₂CH₃ | (2-) OCH₃ | C₄H₉-s | cyclopropyl |
| SO₂CH₃ | (2-) OCH₃ | C₄H₉-t | cyclopropyl |
| SO₂CH₃ | (2-) OCH₃ | cyclopropyl | cyclopropyl |
| SO₂CH₃ | (2-) OCH₃ | CH₂-cyclopropyl | cyclopropyl |
| SO₂CH₃ | (2-) OCH₃ | CH=CHCH₃ | cyclopropyl |
| SO₂CH₃ | (2-) OCH₃ | phenyl | cyclopropyl |
| SO₂CH₃ | (2-) OCH₃ | 4-Cl-phenyl | cyclopropyl |
| SO₂CH₃ | (2-) OCH₃ | benzyl | cyclopropyl |
| SO₂CH₃ | (2-) OCH₃ | N(CH₃)₂ | cyclopropyl |

-continued

| R³ | (position-)(R⁴)ₙ | R⁵ | R⁶ |
|---|---|---|---|
| SO₂CH₃ | (2-) OCH₃ | *N-methylmorpholine* | *cyclopropylmethyl* |
| SO₂CH₃ | (2-) OCH₃ | Cl | *cyclopropylmethyl* |
| SO₂CH₃ | (2-) OCH₃ | Br | *cyclopropylmethyl* |
| Cl | (2-) OCH₃ | CF₃ | N(CH₃)₂ |
| Cl | (2-) OCH₃ | SCH₃ | N(CH₃)₂ |
| Cl | (2-) OCH₃ | SC₂H₅ | N(CH₃)₂ |
| Cl | (2-) OCH₃ | SC₃H₇ | N(CH₃)₂ |
| Cl | (2-) OCH₃ | SC₃H₇-i | N(CH₃)₂ |
| Cl | (2-) OCH₃ | *SCH₂CH=CH₂* | N(CH₃)₂ |
| Cl | (2-) OCH₃ | *SCH₂C≡CH* | N(CH₃)₂ |
| Cl | (2-) OCH₃ | *SCH=CHCH₃* | N(CH₃)₂ |
| Cl | (2-) OCH₃ | *SC≡CCH₃* | N(CH₃)₂ |
| Cl | (2-) OCH₃ | *SCH₂-cyclopropyl* | N(CH₃)₂ |
| Cl | (2-) OCH₃ | SCH=C=CH₂ | N(CH₃)₂ |
| Cl | (2-) OCH₃ | SCH₂CN | N(CH₃)₂ |
| Cl | (2-) OCH₃ | SCH₂CH₂CN | N(CH₃)₂ |
| Cl | (2-) OCH₃ | OCH₃ | N(CH₃)₂ |
| Cl | (2-) OCH₃ | OC₂H₅ | N(CH₃)₂ |
| Cl | (2-) OCH₃ | OC₃H₇ | N(CH₃)₂ |
| Cl | (2-) OCH₃ | OC₃H₇-i | N(CH₃)₂ |
| Cl | (2-) OCH₃ | OC₄H₉ | N(CH₃)₂ |
| Cl | (2-) OCH₃ | OCH₂CF₃ | N(CH₃)₂ |
| Cl | (2-) OCH₃ | *OCH₂-cyclopropyl* | N(CH₃)₂ |
| Cl | (2-) OCH₃ | OC₆H₅ | N(CH₃)₂ |
| Cl | (2-) OCH₃ | H | N(CH₃)₂ |
| Cl | (2-) OCH₃ | CH₃ | N(CH₃)₂ |
| Cl | (2-) OCH₃ | C₂H₅ | N(CH₃)₂ |
| Cl | (2-) OCH₃ | C₃H₇ | N(CH₃)₂ |
| Cl | (2-) OCH₃ | C₃H₇-i | N(CH₃)₂ |
| Cl | (2-) OCH₃ | C₄H₉ | N(CH₃)₂ |
| Cl | (2-) OCH₃ | C₄H₉-i | N(CH₃)₂ |
| Cl | (2-) OCH₃ | C₄H₉-s | N(CH₃)₂ |
| Cl | (2-) OCH₃ | C₄H₉-t | N(CH₃)₂ |
| Cl | (2-) OCH₃ | *cyclopropyl* | N(CH₃)₂ |
| Cl | (2-) OCH₃ | *cyclopropylmethyl* | N(CH₃)₂ |
| Cl | (2-) OCH₃ | CH=CHCH₃ | N(CH₃)₂ |
| Cl | (2-) OCH₃ | *4-methylphenyl* | N(CH₃)₂ |
| Cl | (2-) OCH₃ | *4-chloro-methylphenyl* | N(CH₃)₂ |
| Cl | (2-) OCH₃ | *benzyl/phenethyl* | N(CH₃)₂ |
| Cl | (2-) OCH₃ | N(CH₃)₂ | N(CH₃)₂ |
| Cl | (2-) OCH₃ | *N-methylmorpholine* | N(CH₃)₂ |
| Cl | (2-) OCH₃ | Cl | N(CH₃)₂ |
| Cl | (2-) OCH₃ | Br | N(CH₃)₂ |
| SO₂CH₃ | (2-) OCH₃ | CF₃ | N(CH₃)₂ |
| SO₂CH₃ | (2-) OCH₃ | SCH₃ | N(CH₃)₂ |
| SO₂CH₃ | (2-) OCH₃ | SC₂H₅ | N(CH₃)₂ |
| SO₂CH₃ | (2-) OCH₃ | SC₃H₇ | N(CH₃)₂ |
| SO₂CH₃ | (2-) OCH₃ | SC₃H₇-i | N(CH₃)₂ |
| SO₂CH₃ | (2-) OCH₃ | *SCH₂CH=CH₂* | N(CH₃)₂ |
| SO₂CH₃ | (2-) OCH₃ | *SCH₂C≡CH* | N(CH₃)₂ |
| SO₂CH₃ | (2-) OCH₃ | *SCH=CHCH₃* | N(CH₃)₂ |
| SO₂CH₃ | (2-) OCH₃ | *SC≡CCH₃* | N(CH₃)₂ |

-continued

| R³ | (position-)(R⁴)ₙ | R⁵ | R⁶ |
|---|---|---|---|
| SO₂CH₃ | (2-) OCH₃ | (cyclopropylmethylthio group) | N(CH₃)₂ |
| SO₂CH₃ | (2-) OCH₃ | SCH=C=CH₂ | N(CH₃)₂ |
| SO₂CH₃ | (2-) OCH₃ | SCH₂CN | N(CH₃)₂ |
| SO₂CH₃ | (2-) OCH₃ | SCH₂CH₂CN | N(CH₃)₂ |
| SO₂CH₃ | (2-) OCH₃ | OCH₃ | N(CH₃)₂ |
| SO₂CH₃ | (2-) OCH₃ | OC₂H₅ | N(CH₃)₂ |
| SO₂CH₃ | (2-) OCH₃ | OC₃H₇ | N(CH₃)₂ |
| SO₂CH₃ | (2-) OCH₃ | OC₃H₇-i | N(CH₃)₂ |
| SO₂CH₃ | (2-) OCH₃ | OC₄H₉ | N(CH₃)₂ |
| SO₂CH₃ | (2-) OCH₃ | OCH₂CF₃ | N(CH₃)₂ |
| SO₂CH₃ | (2-) OCH₃ | (cyclopropylmethoxy group) | N(CH₃)₂ |
| SO₂CH₃ | (2-) OCH₃ | OC₆H₅ | N(CH₃)₂ |
| SO₂CH₃ | (2-) OCH₃ | H | N(CH₃)₂ |
| SO₂CH₃ | (2-) OCH₃ | CH₃ | N(CH₃)₂ |
| SO₂CH₃ | (2-) OCH₃ | C₂H₅ | N(CH₃)₂ |
| SO₂CH₃ | (2-) OCH₃ | C₃H₇ | N(CH₃)₂ |
| SO₂CH₃ | (2-) OCH₃ | C₃H₇-i | N(CH₃)₂ |
| SO₂CH₃ | (2-) OCH₃ | C₄H₉ | N(CH₃)₂ |
| SO₂CH₃ | (2-) OCH₃ | C₄H₉-i | N(CH₃)₂ |
| SO₂CH₃ | (2-) OCH₃ | C₄H₉-s | N(CH₃)₂ |
| SO₂CH₃ | (2-) OCH₃ | C₄H₉-t | N(CH₃)₂ |
| SO₂CH₃ | (2-) OCH₃ | (cyclopropyl) | N(CH₃)₂ |
| SO₂CH₃ | (2-) OCH₃ | (cyclopropylmethyl) | N(CH₃)₂ |
| SO₂CH₃ | (2-) OCH₃ | CH=CHCH₃ | N(CH₃)₂ |
| SO₂CH₃ | (2-) OCH₃ | (4-methylphenyl) | N(CH₃)₂ |
| SO₂CH₃ | (2-) OCH₃ | (4-chloro-methylphenyl) | N(CH₃)₂ |
| SO₂CH₃ | (2-) OCH₃ | (benzyl-methyl) | N(CH₃)₂ |
| SO₂CH₃ | (2-) OCH₃ | N(CH₃)₂ | N(CH₃)₂ |
| SO₂CH₃ | (2-) OCH₃ | (morpholinomethyl) | N(CH₃)₂ |
| SO₂CH₃ | (2-) OCH₃ | Cl | N(CH₃)₂ |
| SO₂CH₃ | (2-) OCH₃ | Br | N(CH₃)₂ |
| Cl | (2-) OCH₃ | CH₃ | OCH₃ |
| Cl | (2-) OCH₃ | C₂H₅ | OCH₃ |
| Cl | (2-) OCH₃ | C₃H₇ | OCH₃ |
| Cl | (2-) OCH₃ | SCH₃ | OCH₃ |
| Cl | (2-) OCH₃ | SC₂H₅ | OCH₃ |
| Cl | (2-) OCH₃ | OCH₃ | OCH₃ |
| Cl | (2-) OCH₃ | OC₂H₅ | OCH₃ |
| Cl | (2-) OCH₃ | CH₃ | OC₂H₅ |
| Cl | (2-) OCH₃ | C₂H₅ | OC₂H₅ |
| Cl | (2-) OCH₃ | C₃H₇ | OC₂H₅ |
| Cl | (2-) OCH₃ | SCH₃ | OC₂H₅ |
| Cl | (2-) OCH₃ | SC₂H₅ | OC₂H₅ |
| Cl | (2-) OCH₃ | OCH₃ | OC₂H₅ |
| Cl | (2-) OCH₃ | OC₂H₅ | OC₂H₅ |
| SO₂CH₃ | (2-) OCH₃ | Cl | OCH₃ |
| SO₂CH₃ | (2-) OCH₃ | Br | OCH₃ |
| SO₂CH₃ | (2-) OCH₃ | CH₃ | OCH₃ |
| SO₂CH₃ | (2-) OCH₃ | C₂H₅ | OCH₃ |
| SO₂CH₃ | (2-) OCH₃ | C₃H₇ | OCH₃ |
| SO₂CH₃ | (2-) OCH₃ | SCH₃ | OCH₃ |
| SO₂CH₃ | (2-) OCH₃ | SC₂H₅ | OCH₃ |
| SO₂CH₃ | (2-) OCH₃ | OCH₃ | OC₂H₅ |
| SO₂CH₃ | (2-) OCH₃ | OC₂H₅ | OC₂H₅ |
| SO₂CH₃ | (2-) OCH₃ | CH₃ | OC₂H₅ |
| SO₂CH₃ | (2-) OCH₃ | C₂H₅ | OC₂H₅ |
| SO₂CH₃ | (2-) OCH₃ | C₃H₇ | OC₂H₅ |
| SO₂CH₃ | (2-) OCH₃ | SCH₃ | OC₂H₅ |
| SO₂CH₃ | (2-) OCH₃ | SC₂H₅ | OC₂H₅ |
| SO₂CH₃ | (2-) OCH₃ | OCH₃ | OC₂H₅ |

Group 3

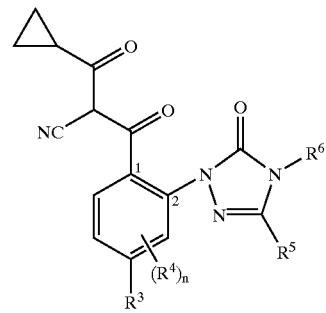

(IA-2)

$R^3$, $(R^4)_n$, $R^5$ and $R^6$ have, for example, the meanings given above in Group 1.

Group 4

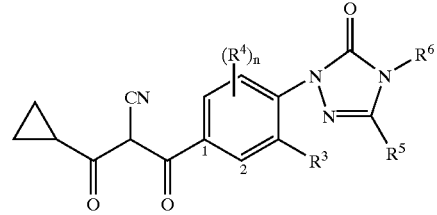

(IC-1)

$R^3$, $(R^4)_n$, $R^5$ and $R^6$ have, for example, the meanings given above in Group 2.

The novel substituted benzoyl ketones of the general formula (I) have strong and selective herbicidal activity.

The novel substituted benzoyl ketones of the general formula (I) are obtained when:

(a) ketones of the general formula (II)

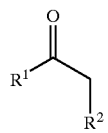
(II)

in which
R¹ and R² are each as defined above,
are reacted with substituted benzoic acids of the general formula (III)

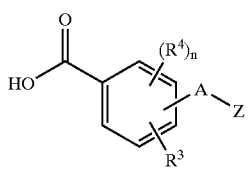
(III)

in which
n, A, R³, R⁴ and Z are each as defined above,
if appropriate in the presence of one or more reaction auxiliaries and if appropriate in the presence of one or more diluents,
or when (b) benzoylisoxazoles of the general formula (IV)

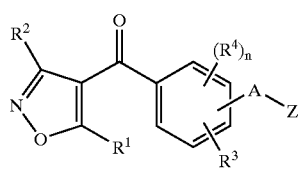
(IV)

in which
n, A, R¹, R², R³, R⁴ and Z are each as defined above,
are isomerized in the presence of one or more reaction auxiliaries and if appropriate in the presence of one or more diluents, and electrophilic or nucleophilic substitutions and/or oxidations or reductions within the scope of the definition of the substituents are, if appropriate, subsequently, i.e. after the processes (a) or (b) according to the invention have been carried out, carried out in a customary manner on the resulting compounds of the formula (I), or the compounds of the formula (I) are converted in a customary manner into salts.

The compounds of the formula (I) can be converted by customary methods into other compounds of the formula (I) according to the definition above, for example by nucleophilic substitution (for example R⁵: Cl→OC₂H₅, SCH₃) or by oxidation (for example R⁵: CH₂SCH₃→CH₂S(O)CH₃).

In principle, the compounds of the general formula (I) can also be synthesized as outlined below:

Reaction of ketones of the general formula (II)—above— with reactive derivatives of the substituted benzoic acids of the general formula (I)—above—, in particular with appropriate carbonyl chlorides, carboxylic anhydrides, carboxylic acid cyanides, methyl carboxylates or ethyl carboxylates—if appropriate in the presence of reaction auxiliaries, such as, for example, triethylamine (and, if appropriate, additionally zinc chloride), and if appropriate in the presence of a diluent, such as, for example, methylene chloride:

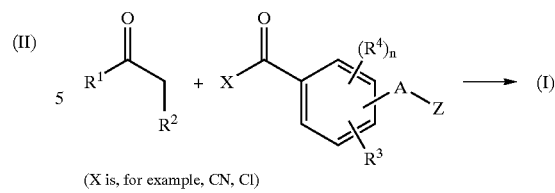
(X is, for example, CN, Cl)

Using, for example, ethyl methylsulfonylmethyl ketone and 2-(3-carboxy-5-fluorobenzyl)-5-ethyl-4-methoxy-2,4-dihydro-3H-1,2,4-triazol-3-one as starting materials, the course of the reaction in the process (a) according to the invention can be illustrated by the following formula scheme:

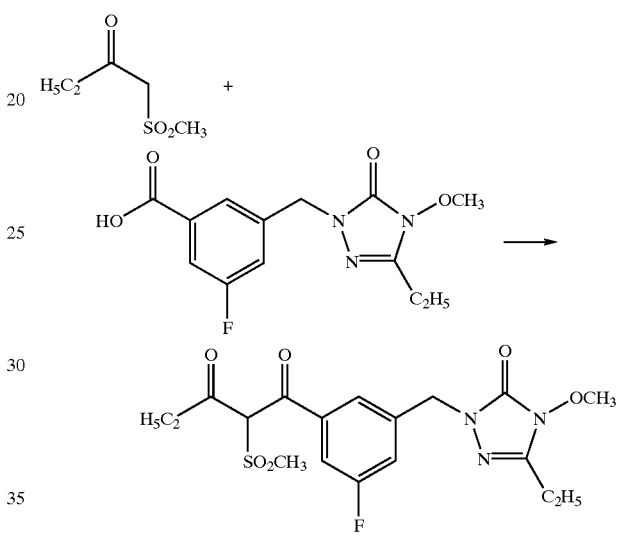

Using, for example, (5-cyclopropyl-isoxazol-4-yl)-[2-(4-methyl-3-methylthio-5-oxo-4,5-dihydro-[1,2,4]-triazol-1-yl-methyl)-4-trifluoromethyl-phenyl]-methanone as starting material, the course of the reaction in the process (b) according to the invention can be illustrated by the following formula scheme:

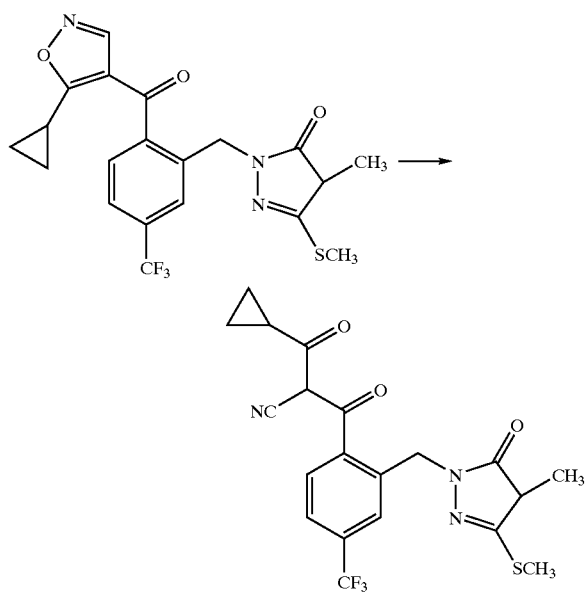

The formula (II) provides a general definition of the ketones to be used as starting materials in the process (a) according to the invention for preparing compounds of the general formula (I). In the general formula (II), $R^1$ and $R^2$ each preferably have those meanings which have already been mentioned above, in connection with the description of the compounds of the general formula (I) according to the invention, as being preferred, particularly preferred, very particularly preferred or most preferred for $R^1$ and $R^2$.

The starting materials of the general formula (II) are known and/or can be prepared by processes known per se (cf. the Preparation Examples).

The formula (III) provides a general definition of the substituted benzoic acids further to be used as starting materials in the process (a) according to the invention for preparing compounds of the formula (I). In the formula (III), n, A, $R^3$, $R^4$ and Z each preferably have those meanings which have already been mentioned above, in connection with the description of the compounds of the formula (I) according to the invention, as being preferred, particularly preferred, very particularly preferred or most preferred for n, A, $R^3$, $R^4$ and Z.

The starting materials of the general formula (m), except for 2-(5-carboxy-2,4-dichloro-phenyl)-4-difluoromethyl-5-methyl-2,4-dihydro-3H-1,2,4-triazol-3-one—alias 2,4-dichloro-5-(4-difluoromethyl-4,5-dihydro-3-methyl-5-oxo-1H-1,2,4-triazol-1-yl)-benzoic acid (CAS-Reg.-No. 90208-77-8)—and 2-(5-carboxy-2,4-dichlorophenyl)4,5-dimethyl-2,4-dihydro-3H-1,2,4-triazol-3-one —alias 2,4-dichloro-5-(4,5-dihydro-3,4-dimethyl-5-oxo-1H-1,2,4-triazol-1-yl)-benzoic acid (CAS-Reg.-No. 90208-76-7)—have hitherto not been disclosed in the literature. Except for 2-(5-carboxy-2,4-dichloro-phenyl)-4-difluoromethyl-5-methyl-2,4-dihydro-3H-1,2,4-triazol-3-one and 2-(5-carboxy-2,4-dichloro-phenyl)-4,5-dimethyl-2,4-dihydro-3H-1,2,4-triazol-3-one (cf. JP-A-58225070—cited in Chem. Abstracts 100:209881, JP-A-02015069—cited in Chem. Abstracts 113:23929) they are, however, part of the subject-matter of an earlier but not prior-published application (cf. DE-A-19833360).

The substituted benzoic acids of the general formula (E) are obtained when benzoic acid derivatives of the general formula (V)

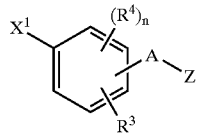

(V)

in which n, A, $R^3$ and $R^4$ and Z are each as defined above and $X^1$ represents cyano, carbamoyl or alkoxycarbonyl, are reacted with water, if appropriate in the presence of a hydrolysis auxiliary, such as, for example, sulfuric acid, at temperatures between 50° C. and 120° C. (cf. the Preparation Examples).

The benzoic acid derivatives of the general formula (V) required as precursors are known and/or can be prepared by processes known per se (cf. DE-A-3839480, DE-A-4239296, EP-A-597360, EP-A-609734, DE-A-4303676, EP-A-617026, DE-A-4405614, U.S. Pat. No. 5,378,681).

The novel substituted benzoic acids of the general formula (III) are also obtained when halogeno(alkyl)benzoic acids of the general formula (VI)

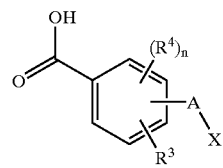

(VI)

in which n, A, $R^3$ and $R^4$ are each as defined above and

X represents halogen (in particular chlorine or bromine)

are reacted with compounds of the general formula (VII),

(VII)

in which

Z is as defined above, if appropriate in the presence of a reaction auxiliary, such as, for example, triethylamine or potassium carbonate, and if appropriate in the presence of a diluent, such as, for example, acetone, acetonitrile, N,N-dimethyl-formamide or N,N-dimethyl-acetamide, at temperatures between 50° C. and 200° C. (cf. the Preparation Examples).

In place of the halogeno(alkyl)benzoic acids of the general formula (VI) it is also possible to react the corresponding nitriles, amides and esters—in particular the methyl esters or the ethyl esters—analogously to the method described above with compounds of the general formula (VII). By subsequent hydrolysis according to customary methods, for example by reaction with aqueous/ethanol potassium hydroxide solution, it is then possible to obtain the corresponding substituted benzoic acids.

The halogeno(alkyl)benzoic acids of the formula (VI)—or the corresponding nitriles or esters—required as precursors are known and/or can be prepared by processes known per se (cf. EP-A-90369, EP-A-93488, EP-A-399732, EP-A-480641, EP-A-609798, EP-A-763524, DE-A-2126720, WO-A-93/03722, WO-A-97/38977, U.S. Pat. No. 3,978,127, U.S. Pat. No. 4,837,333).

The compounds of the general formula (VII) further required as precursors are known and/or can be prepared by processes known per se.

The process (a) according to the invention for preparing the novel substituted benzoyl ketones of the general formula (I) is, if appropriate, carried out using one or more reaction auxiliaries.

Examples of these which may be mentioned are sodium cyanide, potassium cyanide, acetone cyanohydrin, imidazole, triazole, diethyl cyanophosphonate, 2-cyano-2-(trimethylsilyloxy)-propane and trimethylsilyl cyanide.

Particularly suitable reaction auxiliaries which may be mentioned are diethyl cyanophosphonate and trimethylsilyl cyanide.

The processes (a) and (b) according to the invention for preparing the novel substituted benzoyl ketones of the general formula (I) are, if appropriate, carried out using a (further) reaction auxiliary. Suitable (further) reaction auxiliaries for the processes according to the invention are, in general, basic organic nitrogen compounds, such as, for example, trimethylamine, triethylamine, tripropylamine, tributylamine, ethyl-diisopropylamine, N,N-dimethyl-cyclohexylamine, dicyclohexylamine, ethyl-dicyclohexylamine, N,N-dimethyl-aniline, N,N-dimethyl-benzylamine, pyridine, 2-methyl-, 3-methyl-, 4-methyl-, 2,4-dimethyl-, 2,6-dimethyl-, 3,4-dimethyl- and 3,5-dimethyl-pyridine, 5-ethyl-2-methyl-pyridine, 4-dimethylamino-pyridine, N-methyl-piperidine, 1,4-diazabicyclo[2.2.2]-octane (DABCO), 1,5-diazabicyclo[4.3.0]-non-5-ene (DBN) or 1,8-diazabicyclo[5.4.0]-undec-7-ene (DBU).

Suitable diluents for carrying out the processes (a) and (b) according to the invention are especially inert organic solvents. These include, in particular, aliphatic, alicyclic or aromatic, optionally halogenated hydrocarbons, such as, for example, benzine, benzene, toluene, xylene, chlorobenzene, dichlorobenzene, petroleum ether, hexane, cyclohexane, dichloromethane, chloroform, carbon tetrachloride or 1,2-dichloroethane; ethers, such as diethyl ether, diisopropyl ether, dioxane, tetrahydrofuran, ethylene glycol dimethyl ether or ethylene glycol diethyl ether; ketones, such as acetone, butanone or methyl isobutyl ketone; nitriles, such as acetonitrile, propionitrile or butyronitrile; amides, such as N,N-dimethylformamide, N,N-dimethylacetamide, N-methyl-formanilide, N-methyl-pyrrolidone or hexamethylphosphoric triamide; esters, such as methyl acetate or ethyl acetate; sulphoxides, such as dimethyl sulphoxide.

When carrying out the processes (a) and (b) according to the invention, the reaction temperatures can be varied within a relatively wide range. In general, the reactions are carried out at temperatures between 0° C. and 150° C., preferably between 10° C. and 120° C.

The processes (a) and (b) according to the invention are generally carried out under atmospheric pressure. However, it is also possible to carry out the processes according to the invention under elevated or reduced pressure—in general between 0.1 bar and 10 bar.

For carrying out the processes (a) and (b) according to the invention, the starting materials are generally employed in approximately equimolar amounts. However, it is also possible to employ a relatively large excess of one of the components. The reaction is generally carried out in a suitable diluent in the presence of a dehydrating agent, and the reaction mixture is generally stirred at the required temperature for several hours. Work-up is carried out by customary methods (cf. the Preparation Examples).

The active compounds according to the invention can be used as defoliants, desiccants, haulm killers and, especially, as weed killers. By weeds in the broadest sense there are to be understood all plants which grow in locations where they are undesired. Whether the substances according to the invention act as total or selective herbicides depends essentially on the amount used.

The active compounds according to the invention can be used, for example, in connection with the following plants:

Dicotyledonous weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus, Taraxacum.

Dicotyledonous crops of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis, Cucurbita.

Monocotyledonous weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus, Apera, Aegilops, Phalaris.

Monocotyledonous crops of the genera: Oryza, Zea, Triticum, Hordeum, Avena, Secale, Sorghum, Panicum, Saccharum, Ananas, Asparagus, Allium.

However, the use of the active compounds according to the invention is in no way restricted to these genera, but also extends in the same manner to other plants.

Depending on the concentration, the active compounds according to the invention are suitable for total weed control, for example on industrial terrain and rail tracks and on paths and areas with or without tree growth. Equally, the active compounds according to the invention can be employed for controlling weeds in perennial crops, for example forests, ornamental tree plantings, orchards, vineyards, citrus groves, nut orchards, banana plantations, coffee plantations, tea plantations, rubber plantations, oil palm plantations, cocoa plantations, soft fruit plantings and hop fields, on lawns and turf and pastures and for selective weed control in annual crops.

The compounds of the formula (I) according to the invention have strong herbicidal activity and a broad activity spectrum when used on the soil and on above-ground parts of plants. To a certain extent, they are also suitable for selective control of monocotyledonous and dicotyledonous weeds in monocotyledonous and dicotyledonous crops, both by the pre-emergence and by the post-emergence method.

The active compounds can be converted into the customary formulations, such as solutions, emulsions, wettable powders, suspensions, powders, dusts, pastes, soluble powders, granules, suspo-emulsion concentrates, natural and synthetic substances impregnated with active compound, and microencapsulations in polymeric substances.

These formulations are produced in a known manner, for example by mixing the active compounds with extenders, that is to say liquid solvents and/or solid carriers, optionally with the use of surfactants, that is to say emulsifiers and/or dispersants and/or foam formers.

If the extender used is water, it is also possible to use, for example, organic solvents as auxiliary solvents. Liquid solvents which are mainly suitable are: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol, and also their ethers and esters, ketones, such as acetone, methyl ethyl ketone, methyl isobutyl ketone or cyclohexanone, strongly polar solvents, such as dimethylformamide and dimethyl sulphoxide, and water.

Suitable solid carriers are: for example ammonium salts and ground natural minerals, such as kaolins, clays, talc, chalk, quartz, attapulgite, montmorillonite or diatomaceous earth, and ground synthetic minerals, such as finely divided silica, alumina and silicates; suitable solid carriers for granules are: for example crushed and fractionated natural rocks, such as calcite, marble, pumice, sepiolite, dolomite and synthetic granules of inorganic and organic meals, and granules of organic material, such as sawdust, coconut shells, maize cobs and tobacco stalks; suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and protein hydrolysates; suitable dispersants are: for example lignosulphite waste liquors and methylcellulose.

Tackifiers, such as carboxymethylcellulose, natural and synthetic polymers in the form of powders, granules or latices, such as gum arabic, polyvinyl alcohol and polyvinyl acetate, and also natural phospholipids, such as cephalins and lecithins, and synthetic phospholipids can be used in the formulations. Other possible additives are mineral and vegetable oils.

It is possible to use dyestuffs, such as inorganic pigments, for example iron oxide, titanium oxide, Prussian blue, and organic dyestuffs, such as alizarin dyestuffs, azo dyestuffs and metal phthalocyanine dyestuffs, and trace nutrients, such as salts of iron, manganese, boron, copper, cobalt, molybdenum and zinc.

The formulations generally comprise between 0.1 and 95 per cent by weight of active compound, preferably between 0.5 and 90%.

For controlling weeds, the active compounds according to the invention, as such or in the form of their formulations, can also be used as mixtures with known herbicides, finished formulations or tank mixes being possible.

Possible components for the mixtures are known herbicides, for example acetochlor, acifluorfen(-sodium), aclonifen, alachlor, alloxydim(-sodium), ametryne, amicarbazone, amidochlor, amidosulfuron, anilofos, asulam, atrazine, azafenidin, azimsulfuron, benazolin(-ethyl), benfuresate, bensulfuron(-methyl), bentazon, benzobicyclon, benzofenap, benzoylprop(-ethyl), bialaphos, bifenox, bispyribac(-sodium), bromobutide, bromofenoxim, bromoxynil, butachlor, butroxydim, butylate, cafenstrole, caloxydim, carbetamide, carfentrazone(-ethyl), chlomethoxyfen, chloramben, chloridazon, chlorimuron(-ethyl), chlornitrofen, chlorsulfuron, chlortoluron, cinidon(-ethyl), cinmethylin, cinosulfuron, clethodim, clodinafop(-propargyl), clomazone, clomeprop, clopyralid, clopyrasulfuron(-methyl), cloransulam(-methyl), cumyluron, cyanazine, cybutryne, cycloate, cyclosulfamuron, cycloxydim, cyhalofop(-butyl), 2,4-D, 2,4-DB, 2,4-DP, desmedipham, diallate, dicamba, diclofop(-methyl), diclosulam, diethatyl(-ethyl), difenzoquat, diflufenican, diflufenzopyr, dimefuron, dimepiperate, dimethachlor, dimethametryn, dimethenamid, dimexyflam, dinitramine, diphenamid, diquat, dithiopyr, diuron, dymron, epoprodan, EPTC, esprocarb, ethalfluralin, ethametsulfuron(-methyl), ethofumesate, ethoxyfen, ethoxysulfuron, etobenzanid, fenoxaprop(-P-ethyl), flamprop(-isopropyl), flamprop(-isopropyl-L), flamprop(-methyl), flazasulfuron, fluazifop(-P-butyl), fluazolate, flucarbazone, flufenacet, flumetsulam, flumiclorac(-pentyl), flumioxazin, flumipropyn, flumetsulam, fluometuron, fluorochloridone, fluoroglycofen(-ethyl), flupoxam, flupropacil, flurpyrsulfuron(-methyl, -sodium), flurenol(-butyl), fluridone, fluroxypyr(-meptyl), flurprimidol, flurtamone, fluthiacet(-methyl), fluthiamide, fomesafen, glufosinate(-ammonium), glyphosate(-isopropylammonium), halosafen, haloxyfop(-ethoxyethyl), haloxyfop(-p-methyl), hexazinone, imazamethabenz(-methyl), imazamethapyr, imazamox, imazapic, imazapyr, imazaquin, imazethapyr, imazosulfuron, iodosulfuron, ioxynil, isopropalin, isoproturon, isouron, isoxaben, isoxachlortole, isoxaflutole, isoxapyrifop, lactofen, lenacil, linuron, MCPA, MCPP, mefenacet, mesotrione, metamitron, metazachlor, methabenzthiazuron, metobenzuron, metobromuron, (alpha-)metolachlor, metosulam, metoxuron, metribuzin, metsulfuron(-methyl), molinate, monolinuron, naproanilide, napropamide, neburon, nicosulfuron, norflurazon, orbencarb, oryzalin, oxadiargyl, oxadiazon, oxasulfuron, oxaziclomefone, oxyfluorfen, paraquat, pelargonic acid, pendimethalin, pentoxazone, phenmedipham, picolinafen, piperophos, pretilachlor, primisulfuron(-methyl), prometryn, propachlor, propanil, propaquizafop, propisochlor, propyzamide, prosulfocarb, prosulfuron, pyraflufen(-ethyl), pyrazolate, pyrazosulfuron(-ethyl), pyrazoxyfen, pyribenzoxim, pyributicarb, pyridate, pyriminobac(-methyl), pyrithiobac(-sodium), quinchlorac, quinmerac, quinoclamine, quizalofop(-P-ethyl), quizalofop(-P-tefuryl), rimsulfuron, sethoxydim, simazine, simetryn, sulcotrione, sulfentrazone, sulfometuron(-methyl), sulfosate, sulfosulfuron, tebutam, tebuthiuron, tepraloxydim, terbuthylazine, terbutryn, thenylchlor, thiafluamide, thiazopyr, thidiazimin, thifensulfuron(-methyl), thiobencarb, tiocarbazil, tralkoxydim, triallate, triasulfuron, tribenuron(-methyl), triclopyr, tridiphane, trifluralin, triflusulfuron, tritosulfuron.

A mixture with other known active compounds, such as fungicides, insecticides, acaricides, nematicides, bird repellents, plant nutrients and agents which improve soil structure, is also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing, scattering.

The active compounds according to the invention can be applied both before and after emergence of the plants. They can also be incorporated into the soil before sowing.

The amount of active compound used can vary within a relatively wide range. It depends essentially on the nature of the desired effect. In general, the amounts used are between 1 g and 10 kg of active compound per hectare of soil surface, preferably between 5 g and 5 kg per ha.

The preparation and the use of the active compounds according to the invention can be seen from the examples below.

PREPARATION EXAMPLE

Example 1

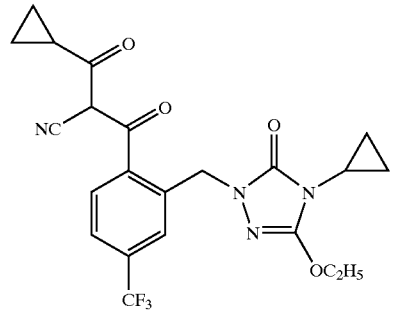

2.38 g (6.4 mmol) of 4-cyclopropyl-5-ethoxy-2-(2-carboxy-5-trifluoromethyl-benzyl)-2,4-dihydro-3H-1,2,4-triazol-3-one are initially charged in 20 ml of N,N-dimethylformamide and, at room temperature (approximately 20° C.), admixed successively with stirring with 0.7 g (6.4 mmol) of cyanomethyl cyclopropyl ketone, 2.7 ml (19 mmol) of triethylamine and 1.04 g (6.4 mmol) of diethyl cyanophosphonate. The reaction mixture is stirred at room temperature for two days, poured into about twice the amount of water, acidified with 2 N hydrochloric acid and shaken with methylene chloride. The organic phase is separated off, washed with 2 N hydrochloric acid, dried with sodium sulphate and filtered. The filtrate is concentrated and the residue is purified by column chromatography (silica gel, hexane/ethyl acetate, vol.: 4/1).

This gives 1.18 g (40% of theory) of 3-cyclopropyl-2-{2-[4-(cyclopropyl-3-ethoxy-5-oxo-4,5-dihydro-1H-1,2,4-triazol-1-yl)-methyl]4-trifluoromethyl-benzoyl}-3-oxo-propanenitrile as an amorphous product.

logP (determined at pH=2): 3.35.

Analogously to Example 1, and in accordance with the general description of the preparation process according to the invention, it is also possible to prepare, for example, the compounds of the general formula (I)—or of the formulae (IA-3), (IB-3), (IC-3)—listed in Tables 1 and 1a below.

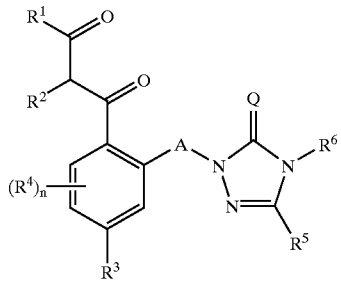
(IA-3)

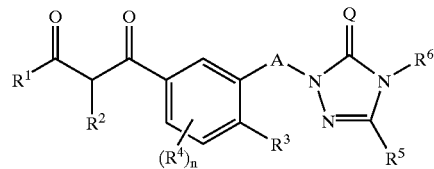
(IB-3)

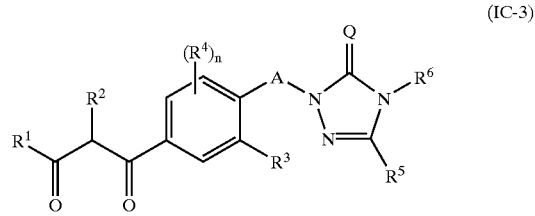
(IC-3)

TABLE 1

Examples of the compounds of the formulae (IA-3), (IB-3) and (IC-3)

| Ex. No. | A | Q | $R^1$ | $R^2$ | $R^3$ | (position) $(R^4)_n$ | $R^5$ | $R^6$ | (formula) Physical data |
|---|---|---|---|---|---|---|---|---|---|
| 2 | $CH_2$ | O | △ | CN | $CF_3$ | — | $SCH_3$ | △ | (IA) logP = 2.92[a)] |
| 3 | $CH_2$ | O | △ | CN | $CF_3$ | — | $OC_2H_5$ | $CH_3$ | (IA) logP = 3.03[a)] |
| 4 | $CH_2$ | O | △ | CN | $CF_3$ | — | $C_2H_5$ | $OC_2H_5$ | (IA) logP = 3.19[a)] |
| 5 | $CH_2$ | O | △ | CN | Br | — | $SCH_3$ | $CH_3$ | (IA) logP = 2.83[a)] |
| 6 | $CH_2$ | O | △ | CN | Br | — | $OC_2H_5$ | $CH_3$ | (IA) logP = 2.94[a)] |
| 7 | $CH_2$ | O | △ | CN | F | — | $N(CH_3)_2$ | $CH_3$ | (IA) logP = 2.28[a)] |
| 8 | $CH_2$ | O | △ | CN | F | — | $OCH_3$ | △ | (IA) logP = 2.56[a)] |
| 9 | $CH_2$ | O | △ | CN | $SO_2CH_3$ | — | $SCH_3$ | $CH_3$ | (IA) logP = 1.74[a)] |
| 10 | $CH_2$ | O | △ | CN | $CF_3$ | — | $CH_3$ | $CH_3$ | (IA) logP = 2.35[a)] |

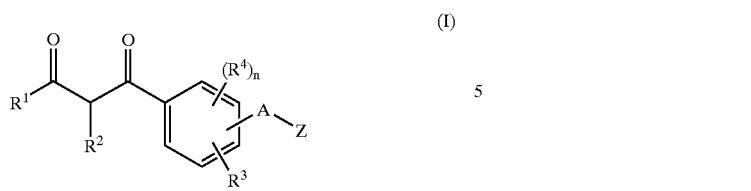
(I)

TABLE 1a

Examples of the compounds of the formula (I)

| Ex. No. | R¹ | R² | (position) R³ | (position) (R⁴)ₙ | (position) —A—Z | Physical data |
|---|---|---|---|---|---|---|
| ID-1 | cyclopropyl | H | (2) Cl | (4) Cl | 1-ethyl-3-methyl-imidazolidin-2-one (3) | logP = 2.34[a] |
| ID-2 | cyclopropyl | H | (2) OCH₃ | (4) Cl | 1-ethyl-3-methyl-imidazolidin-2-one (3) | |
| ID-3 | cyclopropyl | H | (2) Cl | (4) Cl | 1,3-diethyl-imidazolidin-2-one (3) | |
| ID-4 | cyclopropyl | H | (2) OCH₃ | (4) Cl | 1,3-diethyl-imidazolidin-2-one (3) | |
| ID-5 | cyclopropyl | H | (2) Cl | (4) Cl | 1-ethyl-3-methyl-tetrahydropyrimidin-2-one (3) | |
| ID-6 | cyclopropyl | H | (2) Cl | (4) Cl | 1-ethyl-3-(n-propyl)-imidazolidin-2-one (3) | |
| ID-7 | cyclopropyl | H | (2) Cl | (4) Cl | 1-ethyl-3-(i-propyl)-imidazolidin-2-one (3) | |

TABLE 1a-continued
Examples of the compounds of the formula (I)
| Ex. No. | R¹ | R² | (position) R³ | (position) (R⁴)ₙ | (position) —A—Z | Physical data |
|---|---|---|---|---|---|---|
| ID-8 |  | H | (2) Cl | (4) Cl | 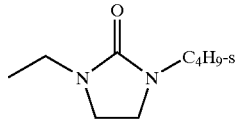 (3) | |
| ID-9 |  | H | (2) Cl | (4) Cl | 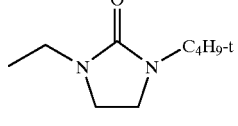 (3) | |
| ID-10 |  | H | (2) OCH₃ | (4) Cl | 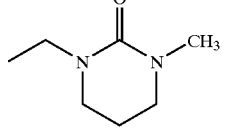 (3) | |
| ID-11 |  | H | (2) Cl | (4) SO₂CH₃ | 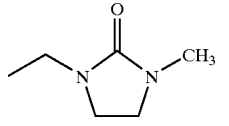 (3) | |
| ID-12 |  | H | (2) Cl | (4) SO₂CH₃ | 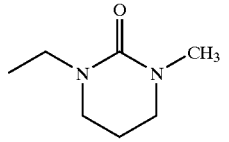 (3) | |
| ID-13 |  | H | (2) SO₂CH₃ | (4) Cl | 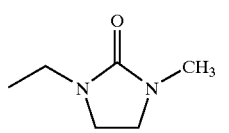 (3) | |
| ID-14 |  | H | (2) SO₂CH₃ | (4) Cl | 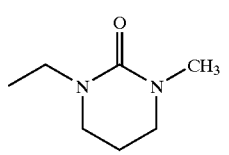 (3) | |
| ID-15 |  | H | (2) Cl | (4) CF₃ | 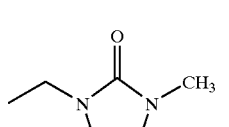 (3) | |

TABLE 1a-continued

Examples of the compounds of the formula (I)

| Ex. No. | R¹ | R² | (position) R³ | (position) (R⁴)ₙ | (position) —A—Z | Physical data |
|---|---|---|---|---|---|---|
| ID-16 | cyclopropyl | H | (2) Cl | (4) CF₃ | 1-ethyl-3-methyl-tetrahydropyrimidin-2(1H)-one (3) | |
| ID-17 | cyclopropyl | H | (2) NO₂ | (4) CF₃ | 1-ethyl-3-methyl-imidazolidin-2-one (3) | |
| ID-18 | cyclopropyl | H | (2) NO₂ | (4) CF₃ | 1-ethyl-3-methyl-tetrahydropyrimidin-2(1H)-one (3) | |
| ID-19 | cyclopropyl | H | (2) OCH₃ | (4) CF₃ | 1-ethyl-3-methyl-imidazolidin-2-one (3) | |
| ID-20 | cyclopropyl | H | (2) OCH₃ | (4) CF₃ | 1-ethyl-3-methyl-tetrahydropyrimidin-2(1H)-one (3) | |
| ID-21 | cyclopropyl | H | (2) Cl | (4) CN | 1-ethyl-3-methyl-imidazolidin-2-one (3) | |
| ID-22 | cyclopropyl | H | (2) Cl | (4) CN | 1-ethyl-3-methyl-tetrahydropyrimidin-2(1H)-one (3) | |
| ID-23 | cyclopropyl | H | (2) OCH₃ | (4) CN | 1-ethyl-3-methyl-imidazolidin-2-one (3) | |

TABLE 1a-continued

Examples of the compounds of the formula (I)

| Ex. No. | R¹ | R² | (position) R³ | (position) (R⁴)ₙ | (position) —A—Z | Physical data |
|---|---|---|---|---|---|---|
| ID-24 | cyclopropyl | H | (2) OCH₃ | (4) CN | 1-ethyl-3-methyl-tetrahydropyrimidin-2-one (3) | |
| ID-25 | cyclopropyl | H | (2) Cl | (4) F | 1-ethyl-3-methyl-imidazolidin-2-one (3) | |
| ID-26 | cyclopropyl | H | (2) Cl | (4) F | 1-ethyl-3-methyl-tetrahydropyrimidin-2-one (3) | |
| ID-27 | cyclopropyl | H | H | — | 1-ethyl-3-methyl-imidazolidin-2-one (2) | |
| ID-28 | cyclopropyl | H | H | — | 1-ethyl-3-methyl-tetrahydropyrimidin-2-one (2) | |
| ID-29 | cyclopropyl | H | (4) F | — | 1-ethyl-3-methyl-imidazolidin-2-one (2) | |
| ID-30 | cyclopropyl | H | (4) F | — | 1-ethyl-3-methyl-tetrahydropyrimidin-2-one (2) | |
| ID-31 | cyclopropyl | H | (4) Cl | — | 1-ethyl-3-methyl-imidazolidin-2-one (2) | |

TABLE 1a-continued

Examples of the compounds of the formula (I)

| Ex. No. | R¹ | R² | (position) R³ | (position) (R⁴)ₙ | (position) —A—Z | Physical data |
|---|---|---|---|---|---|---|
| ID-32 | cyclopropyl | H | (4) Cl | — | N(ethyl)-C(=O)-N(CH₃) tetrahydropyrimidinone (2) | |
| ID-33 | cyclopropyl | H | (4) F | — | N(ethyl)-C(=O)-N(C₂H₅) imidazolidinone (2) | |
| ID-34 | cyclopropyl | H | (4) Cl | — | N(ethyl)-C(=O)-N(C₂H₅) imidazolidinone (2) | |
| ID-35 | cyclopropyl | H | (4) Br | — | N(ethyl)-C(=O)-N(CH₃) imidazolidinone (2) | |
| ID-36 | cyclopropyl | H | (4) I | — | N(ethyl)-C(=O)-N(CH₃) imidazolidinone (2) | |
| ID-37 | cyclopropyl | H | (4) NO₂ | — | N(ethyl)-C(=O)-N(CH₃) imidazolidinone (2) | |
| ID-38 | cyclopropyl | H | (4) CN | — | N(ethyl)-C(=O)-N(CH₃) imidazolidinone (2) | |
| ID-39 | cyclopropyl | H | (4) CF₃ | — | N(ethyl)-C(=O)-N(CH₃) imidazolidinone (2) | |

TABLE 1a-continued

Examples of the compounds of the formula (I)

| Ex. No. | R¹ | R² | (position) R³ | (position) (R⁴)ₙ | (position) —A—Z | Physical data |
|---|---|---|---|---|---|---|
| ID-40 | cyclopropyl | H | (4) SO$_2$CH$_3$ | — | ethyl-imidazolidinone-CH$_3$ (2) | |
| ID-41 | cyclopropyl | H | (4) OCH$_3$ | — | ethyl-imidazolidinone-CH$_3$ (2) | |
| ID-42 | cyclopropyl | H | (4) OCF$_3$ | — | ethyl-imidazolidinone-CH$_3$ (2) | |
| ID-43 | cyclopropyl | H | (4) OCHF$_2$ | — | ethyl-imidazolidinone-CH$_3$ (2) | |
| ID-44 | cyclopropyl | H | (4) SCH$_3$ | — | ethyl-imidazolidinone-CH$_3$ (2) | |
| ID-45 | cyclopropyl | H | (4) SOCH$_3$ | — | ethyl-imidazolidinone-CH$_3$ (2) | |
| ID-46 | cyclopropyl | CO$_2$CH$_3$ | (2) Cl | (4) Cl | ethyl-imidazolidinone-CH$_3$ (3) | |
| ID-47 | cyclopropyl | CO$_2$CH$_3$ | (2) OCH$_3$ | (4) Cl | ethyl-imidazolidinone-CH$_3$ (3) | |

TABLE 1a-continued

Examples of the compounds of the formula (I)

| Ex. No. | R¹ | R² | (position) R³ | (position) $(R^4)_n$ | (position) —A—Z | Physical data |
|---|---|---|---|---|---|---|
| ID-48 | cyclopropyl | −C(=O)OCH₃ with CH₃ | (2) Cl | (4) Cl | N-ethyl, N'-methyl tetrahydropyrimidin-2-one (3) | |
| ID-49 | cyclopropyl | −C(=O)OCH₃ with CH₃ | (2) OCH₃ | (4) Cl | N-ethyl, N'-methyl tetrahydropyrimidin-2-one (3) | |
| ID-50 | cyclopropyl | SCH₃ | (2) Cl | (4) Cl | N-ethyl, N'-methyl imidazolidin-2-one (3) | |
| ID-51 | cyclopropyl | SCH₃ | (2) OCH₃ | (4) Cl | N-ethyl, N'-methyl imidazolidin-2-one (3) | |
| ID-52 | cyclopropyl | SCH₃ | (2) Cl | (4) Cl | N-ethyl, N'-methyl tetrahydropyrimidin-2-one (3) | |
| ID-53 | cyclopropyl | SCH₃ | (2) OCH₃ | (4) Cl | N-ethyl, N'-methyl tetrahydropyrimidin-2-one (3) | |
| ID-54 | cyclopropyl | H | (2) Cl | (4) Cl | N-ethyl, N'-ethyl tetrahydropyrimidin-2-one (3) | |
| ID-55 | cyclopropyl | H | (2) OCH₃ | (4) Cl | N-ethyl, N'-ethyl tetrahydropyrimidin-2-one (3) | |

TABLE 1a-continued

Examples of the compounds of the formula (I)

| Ex. No. | R¹ | R² | (position) R³ | (position) (R⁴)ₙ | (position) —A—Z | Physical data |
|---|---|---|---|---|---|---|
| ID-56 | cyclopropyl | H | (2) Cl | (4) Cl | 1-ethyl-3-(isopropyl)tetrahydropyrimidin-2(1H)-one (3) | |
| ID-57 | cyclopropyl | H | (2) OCH₃ | (4) Cl | 1-ethyl-3-(isopropyl)tetrahydropyrimidin-2(1H)-one (3) | |
| ID-58 | cyclopropyl | H | (4) CF₃ | — | 1-ethyl-3-methyltetrahydropyrimidin-2(1H)-one (2) | |
| ID-59 | cyclopropyl | H | (4) CF₃ | — | 1,3-diethylimidazolidin-2-one (2) | |
| ID-60 | cyclopropyl | H | (4) CF₃ | — | 1,3-diethyltetrahydropyrimidin-2(1H)-one (2) | |
| ID-61 | cyclopropyl | H | (2) Cl | (4) Cl | 3-ethyloxazolidin-2-one (2) | |
| ID-62 | cyclopropyl | H | (2) OCH₃ | (4) Cl | 3-ethyloxazolidin-2-one (2) | |
| ID-63 | cyclopropyl | H | (2) Cl | (4) Cl | 1-cyclopropyl-3-ethyltetrahydropyrimidin-2(1H)-one (3) | |

TABLE 1a-continued

Examples of the compounds of the formula (I)

| Ex. No. | R¹ | R² | (position) R³ | (position) (R⁴)ₙ | (position) —A—Z | Physical data |
|---|---|---|---|---|---|---|
| ID-64 | cyclopropyl | H | (2) OCH₃ | (4) Cl | N-ethyl, N'-cyclopropyl tetrahydropyrimidin-2-one (3) | |
| ID-65 | cyclopropyl | H | (2) Cl | (4) Cl | N-ethyl, N'-cyclopropyl imidazolidin-2-one (3) | |
| ID-66 | cyclopropyl | H | (2) OCH₃ | (4) Cl | N-ethyl, N'-cyclopropyl imidazolidin-2-one (3) | |
| ID-67 | cyclopropyl | H | (2) NO₂ | (4) SO₂CH₃ | N-ethyl, N'-C₂H₅ imidazolidin-2-one (3) | |
| ID-68 | cyclopropyl | H | (2) NO₂ | (4) SO₂CH₃ | N-ethyl, N'-CH₃ tetrahydropyrimidin-2-one (3) | |
| ID-69 | cyclopropyl | H | (2) Cl | (4) SO₂CH₃ | N-ethyl, N'-cyclopropyl imidazolidin-2-one (3) | |
| ID-70 | cyclopropyl | H | (2) NO₂ | (4) SO₂CH₃ | N-ethyl, N'-cyclopropyl imidazolidin-2-one (3) | |
| ID-71 | cyclopropyl | H | (2) NO₂ | (4) CF₃ | N-ethyl, N'-CH₃ tetrahydropyrimidin-2-one (2) | |

TABLE 1a-continued

Examples of the compounds of the formula (I)

| Ex. No. | $R^1$ | $R^2$ | (position) $R^3$ | (position) $(R^4)_n$ | (position) —A—Z | Physical data |
|---------|-------|-------|------------------|----------------------|-----------------|---------------|
| ID-72 | cyclopropyl | H | (2) $NO_2$ | (4) $CF_3$ | N-ethyl-N'-cyclopropyl imidazolidinone (3) | |
| ID-73 | cyclopropyl | H | (2) Cl | (4) $SO_2CH_3$ | N-ethyl-N'-t-$C_4H_9$ imidazolidinone (3) | |
| ID-74 | cyclopropyl | H | (2) $NO_2$ | (4) $SO_2CH_3$ | N-ethyl-N'-t-$C_4H_9$ imidazolidinone (3) | |
| ID-75 | cyclopropyl | H | (2) $NO_2$ | (4) $CF_3$ | N-ethyl-N'-t-$C_4H_9$ imidazolidinone (3) | |
| ID-76 | cyclopropyl | H | (2) Cl | (4) $SO_2CH_3$ | N-ethyl-N'-t-$C_4H_9$ tetrahydropyrimidinone (3) | |
| ID-77 | cyclopropyl | H | (2) $NO_2$ | (4) $SO_2CH_3$ | N-ethyl-N'-t-$C_4H_9$ tetrahydropyrimidinone (3) | |
| ID-78 | cyclopropyl | H | (2) $NO_2$ | (4) $CF_3$ | N-ethyl-N'-t-$C_4H_9$ tetrahydropyrimidinone (3) | |

The logP values given in Table 1 and 1a were determined in accordance with EEC Directive 79/831 Annex V.A8 by HPLC (High Performance Liquid Chromatography) using a reverse-phase column (C 18). Temperature: 43° C.

(a) Mobile phases for the determination in the acidic range: 0.1% aqueous phosphoric acid, acetonitrile; linear gradient from 10% acetonitrile to 90% acetonitrile—the corresponding data in Table 1 are labelled[a]).

(b) Mobile phases for the determination in the neutral range: 0.01 molar aqueous phosphate buffer solution, acetonitrile; linear gradient from 10% acetonitrile to 90% acetonitrile—the corresponding data in Table 1 are labelled[b]).

Calibration was carried out using unbranched alkan-2-ones (with from 3 to 16 carbon atoms) whose logP values are known (determination of the logP values by the retention times using linear interpolation between two successive alkanones).

The lambda-max values were determined in the maxima of the chromatographic signals, using the UV spectra from 200 nm to 400 nm.

Starting Materials of the Formula (II)

Example (II-1)

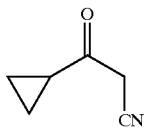

At –60° C., 100 ml of a 1.6 molar solution of butyllithium in hexane are added to 30 ml of tetrahydrofuran. At –60° C., 6.6 g (0.16 mol) of acetonitrile and 14.6 g (0.15 mol) of methyl cyclopropanecarboxylate are then added successively. The resulting white suspension is, after the cooling bath has been removed and the mixture has reached room temperature, poured into about the same amount of 2 N hydrochloric acid and then extracted three times with methylene chloride. The organic extract solutions are combined, dried with sodium sulphate and filtered. The solvent is carefully distilled off from the filtrate under water pump vacuum and the residue is distilled under relatively low pressure.

This gives 7.5 g (46% of theory) of cyanomethyl cyclopropyl ketone of boiling point 56° C. (at 0.8 mbar).

Starting Materials of the Formula (III)

Example (III-1)

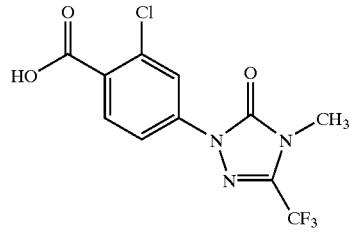

4.5 g (15 mmol) of 2-(3-chloro-4-cyano-phenyl)-4-methyl-5-trifluoromethyl-2,4-dihydro-3H-1,2,4-triazol-3-one are taken up in 80 ml of 60% strength sulphuric acid, and the mixture is heated under reflux for 6 hours. After cooling to room temperature, the resulting crystalline product is isolated by filtration with suction. This gives 4.5 g (91% of theory) of 2-(3-carboxy-4-chloro-phenyl)-4-methyl-5-trifluoromethyl-2,4-dihydro-3H-1,2,4-triazol-3-one of melting point 223° C.

Example (III-2)

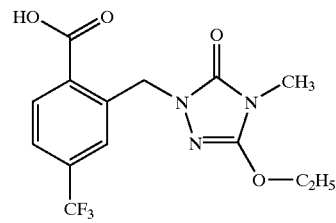

2 g (4.9 mmol) of 5-bromo-4-methyl-2-(2-ethoxycarbonyl-5-trifluoromethyl-benzyl)-2,4-dihydro-3H-1,2,4-triazol-3-one (cf. Example IV-1) are dissolved in 30 ml of 10% strength ethanolic potassium hydroxide solution, and the mixture is heated under reflux for 2 hours. The reaction mixture is concentrated under water pump vacuum, taken up in 20 ml of water and acidified using dilute hydrochloric acid. The solid that precipitates out is filtered off and dried.

This gives 1.2 g (71% of theory) of 5-ethoxy-4-methyl-2-(2-carboxy-5-trifluoromethyl-benzyl)-2,4-dihydro-3H-1,2,4-triazol-3-one as a solid product.

logP: 2.18$^{a)}$

Example (III-3)

13.4 g (35 mmol) of 4-methyl-5-trifluoromethyl-2-(2,6-dichloro-3-methoxycarbonyl-benzyl)-2,4-dihydro-3H-1,2,4-triazol-3-one are initially charged in 60 ml of 1,4-dioxane, and a solution of 1.54 g (38.5 mmol) of sodium hydroxide in 20 ml of water is slowly metered in at room temperature. The reaction mixture is stirred at 60° C. for 150 minutes and then concentrated under water pump vacuum. The residue is dissolved in 100 ml of water, and the pH of the solution is adjusted to 1 by addition of conc. hydrochloric acid. The resulting crystalline product is isolated by filtration with suction.

This gives 11.7 g (90% of theory) of 4-methyl-5-trifluoromethyl-2-(2,6-dichloro-3-carboxy-benzyl)-2,4-dihydro-3H-1,2,4-triazol-3-one of melting point 207° C.

Analogously to Examples (III-1) to (III-3), it is also possible to prepare, for example, the compounds of the general formula (m) listed in Table 2 below.

(III)

TABLE 2

Examples of the compounds of the formula (III)

| Ex. No. | (position-) $R^3$ | (position-) $(R^4)_n$ | (position-) -A-Z | Physical data |
|---|---|---|---|---|
| III-4 | (4-) Cl | — | ![structure: 1-ethyl-4-methyl-5-methyl-1,2,4-triazol-3(4H)-one] (2-) | logP = 1.39[a)] |
| III-5 | (4-) SO$_2$CH$_3$ | — | ![structure: 1-ethyl-4-cyclopropyl-5-cyclopropyl-1,2,4-triazol-3(4H)-one] (3-) | logP = 1.47[a)] |
| III-6 | (4-) F | — | ![structure: 1-ethyl-4-methyl-5-OC$_2$H$_5$-1,2,4-triazol-3(4H)-one] (2-) | logP = 1.73[a)] |
| III-7 | (4-) CF$_3$ | — | ![structure: 1-ethyl-4-cyclopropyl-5-Br-1,2,4-triazol-3(4H)-one] (2-) | logP = 1.65[a)] |
| III-8 | (4-) Br | — | ![structure: 1-ethyl-4-methyl-5-N(CH$_3$)$_2$-1,2,4-triazol-3(4H)-one] (2-) | logP = 1.74[a)] |
| III-9 | (4-) CF$_3$ | — | ![structure: 1-ethyl-4-C$_2$H$_5$-5-OC$_2$H$_5$-1,2,4-triazol-3(4H)-one] (2-) | logP = 2.43[a)] |
| III-10 | (4-) CF$_3$ | — | ![structure: 1-ethyl-4-C$_2$H$_5$-5-OCH$_3$-1,2,4-triazol-3(4H)-one] (2-) | logP = 2.12[a)] |

TABLE 2-continued
Examples of the compounds of the formula (III)
| Ex. No. | (position-) R³ | (position-) (R⁴)ₙ | (position-) -A-Z | Physical data |
|---|---|---|---|---|
| III-11 | (4-) CF₃ | — | 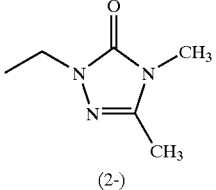<br>(2-) | logP = 1.61[a] |
| III-12 | (4-) CF₃ | — | 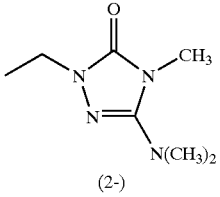<br>(2-) | logP = 1.93[a] |
| III-13 | (4-) CF₃ | — | 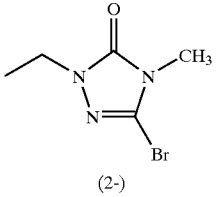<br>(2-) | logP = 2.01[a] |
| III-14 | (4-) CF₃ | — | 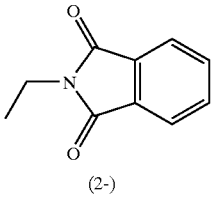<br>(2-) | logP = 1.77[a] |
| III-15 | (3-) CH₃ | — | 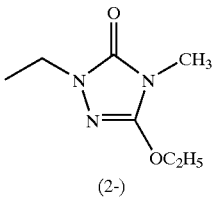<br>(2-) | logP = 1.70[a] |
| III-16 | (4-) SO₂CH₃ | — | 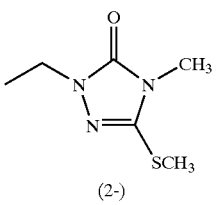<br>(2-) | logP = 1.07[a] |
| III-17 | (4-) CF₃ | — | 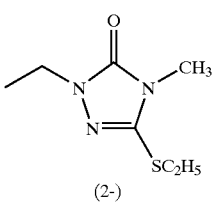<br>(2-) | logP = 2.35[a] |

TABLE 2-continued

Examples of the compounds of the formula (III)

| Ex. No. | (position-) R³ | (position-) (R⁴)ₙ | (position-) -A-Z | Physical data |
|---|---|---|---|---|
| III-18 | (4-) CF₃ | — | (2-) 2-ethyl-4-methyl-5-(i-propylthio)-2,4-dihydro-3H-1,2,4-triazol-3-one | logP = 2.63[a)] |
| III-19 | (4-) CF₃ | — | (2-) 4-cyclopropyl-2-ethyl-5-methoxy-2,4-dihydro-3H-1,2,4-triazol-3-one | logP = 2.13[a)] |
| III-20 | (4-) CF₃ | — | (2-) 2-ethyl-2,5,6,7-tetrahydro-[1,2,4]triazolo[4,3-a]pyridin-3-one | logP = 1.82[a)] |
| III-21 | (4-) CF₃ | — | (2-) 2-ethyl-4-methyl-5-(2,2,2-trifluoroethoxy)-2,4-dihydro-3H-1,2,4-triazol-3-one | logP = 2.48[a)] |
| III-22 | (4-) CF₃ | — | (2-) 2-ethyl-4-methyl-1-methyl-1,2,4-triazolidine-3,5-dione | logP = 1.73[a)] |
| III-23 | (4-) CF₃ | — | (2-) 3-ethyl-5-trifluoromethyl-1,3,4-thiadiazol-2(3H)-one | logP = 3.11[a)] |
| III-24 | (4-) F | — | (2-) 5-dimethylamino-2-ethyl-4-methyl-2,4-dihydro-3H-1,2,4-triazol-3-one | logP = 1.43[a)] |

TABLE 2-continued

Examples of the compounds of the formula (III)

| Ex. No. | (position-) R³ | (position-) (R⁴)ₙ | (position-) -A-Z | Physical data |
|---|---|---|---|---|
| III-25 | (4-) F | — | (2-) triazolinone with N-C₂H₅, N-CH₃, OC₃H₇-n | logP = 1.97[a] |
| III-26 | (4-) F | — | (2-) triazolinone with N-C₂H₅, N-CH₃, CH₂OCH₃ | logP = 1.30[a] |
| III-27 | (4-) F | — | (2-) triazolinone with N-C₂H₅, N-cyclopropyl, OCH₃ | logP = 1.63[a] |
| III-28 | (4-) F | — | (2-) triazolinone with N-C₂H₅, N-cyclopropyl, OC₂H₅ | logP = 1.93[a] |
| III-29 | (4-) CF₃ | — | (2-) pyrazolinone with N-C₂H₅, CH₃, CH₃, CH₃ | logP = 1.78[a] |
| III-30 | (2-) Cl | (4-) Cl | (3-) triazolinone with N-C₂H₅, N-CH₃, SCH₃ | m.p.: 230° C. logP = 1.63[a] |
| III-31 | (2-) Cl | (4-) Cl | (3-) triazolinone with N-C₂H₅, N-CH₃, OC₂H₅ | m.p.: 190° C. logP = 1.73[a] |

TABLE 2-continued

Examples of the compounds of the formula (III)

| Ex. No. | (position-) R³ | (position-) (R⁴)ₙ | (position-) -A-Z | Physical data |
|---|---|---|---|---|
| III-32 | (2-) Cl | (4-) Cl | [1-ethyl-4-cyclopropyl-5-cyclopropyl-1,2,4-triazol-3(2H)-one] (3-) | m.p.: 210° C. logP = 1.87[a)] |
| III-33 | (2-) Cl | (4-) Cl | [1-ethyl-4-methyl-5-methoxy-1,2,4-triazol-3(2H)-one] (3-) | m.p.: 210° C. logP = 1.43[a)] |
| III-34 | (2-) Cl | (4-) Cl | [1-ethyl-4-methyl-5-(i-propoxy)-1,2,4-triazol-3(2H)-one, OC₃H₇-i] (3-) | m.p.: 164° C. logP = 2.01[a)] |
| III-35 | (2-) Cl | (4-) Cl | [1-ethyl-4-methyl-5-(OCH₂CF₃)-1,2,4-triazol-3(2H)-one] (3-) | m.p.: 168° C. logP = 2.04[a)] |
| III-36 | (2-) Cl | (4-) Cl | [1-ethyl-4-methyl-5-Br-1,2,4-triazol-3(2H)-one] (3-) | m.p.: 218° C. logP =1.53[a)] |
| III-37 | (2-) Cl | (4-) Cl | [1-ethyl-4-methyl-5-H-1,2,4-triazol-3(2H)-one] (3-) | m.p.: 259° C. logP = 0.98[a)] |

TABLE 2-continued

Examples of the compounds of the formula (III)

| Ex. No. | (position-) $R^3$ | (position-) $(R^4)_n$ | (position-) -A-Z | Physical data |
|---|---|---|---|---|
| III-38 | (2-) Cl | (4-) Cl | 1-ethyl-4-methyl-5-cyclopropyl-1,2,4-triazol-3(4H)-one (3-) | m.p.: 210° C. logP =1.56[a)] |
| III-39 | (2-) Cl | (4-) Cl | 1-ethyl-4-methyl-5-dimethylamino-1,2,4-triazol-3(4H)-one (3-) | m.p.: 197° C. logP = 1.51[a)] |
| III-40 | (2-) Cl | (4-) Cl | 1-ethyl-4-methyl-5-methyl-1,2,4-triazol-3(4H)-one (3-) | m.p.: 262° C. logP = 1.11[a)] |
| III-41 | (2-) Cl | (4-) Cl | 2-ethyl-5,6,7,8-tetrahydro-[1,2,4]triazolo[4,3-a]pyridin-3(2H)-one (3-) | m.p.: 249° C. logP = 1.30[a)] |
| III-42 | (2-) Cl | (4-) Cl | 1-ethyl-4-cyclopropyl-5-methoxy-1,2,4-triazol-3(4H)-one (3-) | m.p.: 200° C. logP = 1.71[a)] |
| III-43 | (2-) Cl | (4-) Cl | 1-ethyl-4-cyclopropyl-5-ethoxy-1,2,4-triazol-3(4H)-one (3-) | m.p.: 189° C. logP = 2.01[a)] |
| III-44 | (2-) Cl | (4-) Cl | 1-ethyl-4-cyclopropyl-5-isopropoxy-1,2,4-triazol-3(4H)-one (3-) | m.p.: 178° C. logP = 2.28[a)] |

TABLE 2-continued
Examples of the compounds of the formula (III)
| Ex. No. | (position-) R³ | (position-) (R⁴)ₙ | (position-) -A-Z | Physical data |
|---|---|---|---|---|
| III-45 | (2-) Cl | (4-) Cl | 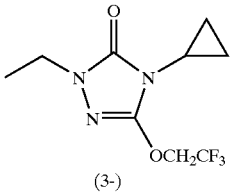 (3-) | m.p.: 161° C. logP = 2.31[a)] |
| III-46 | (2-) Cl | (4-) Cl | 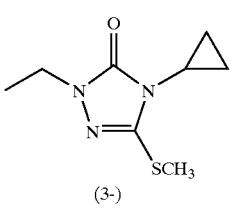 (3-) | m.p.: 200° C. logP = 1.98[a)] |
| III-47 | (2-) Cl | (4-) Cl | 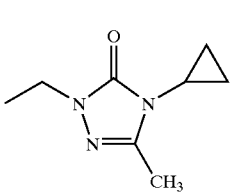 (3-) | m.p.: 201° C. logP = 1.39[a)] |
| III-48 | (2-) Cl | (4-) Cl | 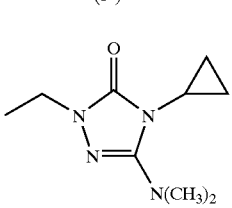 (3-) | m.p.: 207° C. logP = 1.77[a)] |
| III-49 | (2-) Cl | (4-) Cl | 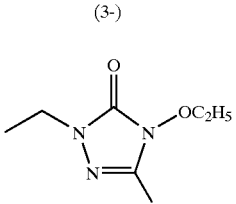 (3-) | m.p.: 140° C. logP = 1.88[a)] |
| III-50 | (4-) OCH₂CHF₂ | — | 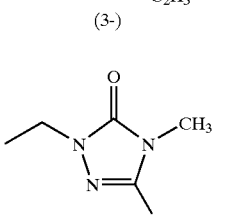 (2-) | m.p.: 154° C. logP = 2.14[a)] |
| III-51 | — | — | 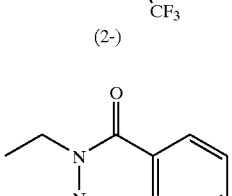 (2-) | m.p.: 214° C. logP = 1.87[a)] |

TABLE 2-continued
Examples of the compounds of the formula (III)
| Ex. No. | (position-) R³ | (position-) (R⁴)ₙ | (position-) -A-Z | Physical data |
|---|---|---|---|---|
| III-52 | — | — | 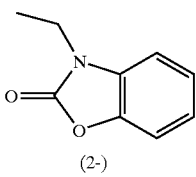 (2-) | m.p.: 194° C. logP = 2.07[a)] |
| III-53 | — | — | 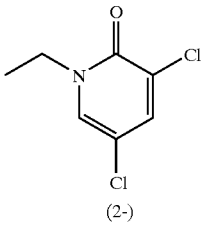 (2-) | m.p.: 181° C. logP = 1.97[a)] |
| III-54 | — | — | 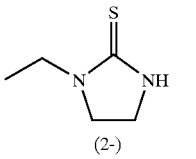 (2-) | m.p.: 251° C. logP = 1.14[a)] |
| III-55 | (2-) Cl | (4-) Cl | 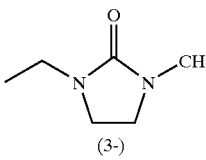 (3-) | logP = 1.38[a)] |
| III-56 | (2-) Cl | (4-) Cl | 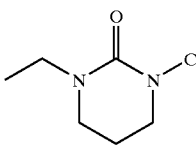 (3-) | logP = 1.48[a)] |
| III-57 | (2-) Cl | (4-) Cl | 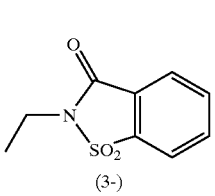 (3-) | |
| III-58 | (4-) Cl | — | 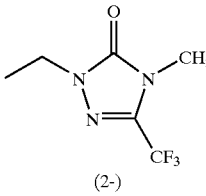 (2-) | ¹H-NMR (DMSO-D6, δ): 5.42 ppm. |

TABLE 2-continued

Examples of the compounds of the formula (III)

| Ex. No. | (position-) R³ | (position-) (R⁴)ₙ | (position-) -A-Z | Physical data |
|---|---|---|---|---|
| III-59 | (4-) CF₃ | — | (2-) triazolinone with N-ethyl, N-CH₃, 5-CH₃ | ¹H-NMR (DMSO-D6, δ): 5.48 ppm. |
| III-60 | (4-) CF₃ | — | (2-) triazolinone with N-ethyl, N-CH₃, 5-CF₃ | ¹H-NMR (DMSO-D6, δ): 5.60 ppm. logP = 2.47[a] |
| III-61 | (4-) CF₃ | — | (2-) triazolinone with N-ethyl, N-cyclopropyl, 5-cyclopropyl | logP = 2.33[a] |
| III-62 | (4-) SO₂CH₃ | — | (3-) triazolinone with N-ethyl, N-CH₃, 5-CF₃ | ¹H-NMR (DMSO-D6, δ): 5.14 ppm. |
| III-63 | (4-) SO₂CH₃ | — | (2-) triazolinone with N-ethyl, N-CH₃, 5-CH₃ | ¹H-NMR (DMSO-D6, δ): 5.27 ppm. |
| III-64 | (4-) Cl | — | (3-) triazolinone with N-ethyl, N-CH₃, 5-CH₃ | ¹H-NMR (CDCl₃, δ): 5.12 ppm. |
| III-65 | (4-) Cl | — | (3-) triazolinone with N-ethyl, N-CH₃, 5-CF₃ | ¹H-NMR (DMSO-D6, δ): 5.20 ppm. |

TABLE 2-continued
Examples of the compounds of the formula (III)
| Ex. No. | (position-) R³ | (position-) (R⁴)ₙ | (position-) -A-Z | Physical data |
|---|---|---|---|---|
| III-66 | (4-) Cl | — | 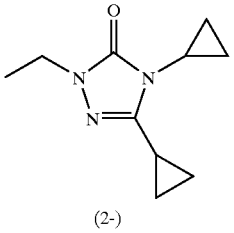 (2-) | ¹H-NMR (DMSO-D6, δ): 5.03 ppm. |
| III-67 | (4-) Br | — | 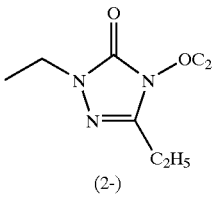 (2-) | ¹H-NMR (DMSO-D6, δ): 5.24 ppm. |
| III-68 | (4-) Br | — | 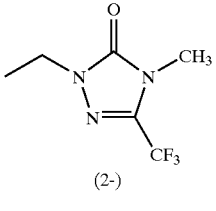 (2-) | ¹H-NMR (DMSO-D6, δ): 5.39 ppm. |
| III-69 | (4-) F | — | 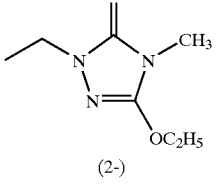 (2-) | ¹H-NMR (DMSO-D6, δ): 5.19 ppm. |
| III-70 | (4-) F | — | 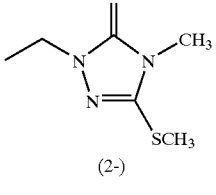 (2-) | ¹H-NMR (DMSO-D6, δ): 5.30 ppm. |
| III-71 | (4-) F | — | 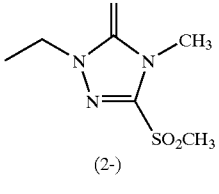 (2-) | ¹H-NMR (DMSO-D6, δ): 5.43 ppm. |
| III-72 | (4-) Br | — | 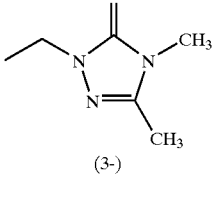 (3-) | ¹H-NMR (CDCl₃ δ): 5.10 ppm. |

TABLE 2-continued

Examples of the compounds of the formula (III)

| Ex. No. | (position-) R³ | (position-) (R⁴)ₙ | (position-) -A-Z | Physical data |
|---|---|---|---|---|
| III-73 | (4-) Br | — | [1-ethyl-4-methyl-5-ethoxy-1,2,4-triazol-3(4H)-one] (3-) | ¹H-NMR (DMSO-D6, δ): 5.03 ppm. |
| III-74 | (4-) Br | — | [1-ethyl-4-methyl-5-trifluoromethyl-1,2,4-triazol-3(4H)-one] (3-) | ¹H-NMR (DMSO-D6, δ): 5.19 ppm. |
| III-75 | (4-) Br | — | [1-ethyl-4-cyclopropyl-5-cyclopropyl-1,2,4-triazol-3(4H)-one] (2-) | ¹H-NMR (DMSO-D6, δ): 5.01 ppm. |
| III-76 | (4-) Cl | — | [1-ethyl-4-cyclopropyl-5-ethoxy-1,2,4-triazol-3(4H)-one] (2-) | ¹H-NMR (DMSO-D6, δ): 5.14 ppm. |
| III-77 | (4-) Cl | — | [1-ethyl-4-ethoxy-5-ethyl-1,2,4-triazol-3(4H)-one] (2-) | ¹H-NMR (DMSO-D6, δ): 5.25 ppm. |
| III-78 | (4-) NO₂ | — | [1-ethyl-4-cyclopropyl-5-ethoxy-1,2,4-triazol-3(4H)-one] (2-) | ¹H-NMR (DMSO-D6, δ): 5.23 ppm. |
| III-79 | (4-) NO₂ | — | [1-ethyl-4-methyl-5-methylthio-1,2,4-triazol-3(4H)-one] (2-) | ¹H-NMR (DMSO-D6, δ): 5.37 ppm. |

TABLE 2-continued

Examples of the compounds of the formula (III)

| Ex. No. | (position-) R³ | (position-) (R⁴)ₙ | (position-) -A-Z | Physical data |
|---|---|---|---|---|
| III-80 | (4-) CF₃ | — | (2-) triazolinone with N-ethyl, N-cyclopropyl, OC₂H₅ | logP = 2.46[a] |
| III-81 | (4-) CF₃ | — | (2-) triazolinone with N-ethyl, N-OC₂H₅, C₂H₅ | ¹H-NMR (DMSO-D6, δ): 5.31 ppm. |
| III-82 | (4-) CF₃ | — | (2-) triazolinone with N-ethyl, N-CH₃, SCH₃ | logP = 2.08[a] |
| III-83 | (4-) OCH₃ | — | (2-) triazolinone with N-ethyl, N-CH₃, OC₂H₅ | ¹H-NMR (CDCl₃, δ): 5.38 ppm. |
| III-84 | (4-) OCH₃ | — | (2-) triazolinone with N-ethyl, N-OC₂H₅, C₂H₅ | ¹H-NMR (CDCl₃, δ): 5.43 ppm. |
| III-85 | (4-) CF₃ | — | (2-) triazolinone with N-ethyl, N-CH₃, CH₂OCH₃ | ¹H-NMR (CDCl₃, δ): 5.47 ppm. |
| III-86 | (4-) Br | — | (2-) fused bicyclic triazolinone with N-ethyl | logP = 1.44[a] |

TABLE 2-continued
Examples of the compounds of the formula (III)
| Ex. No. | (position-) $R^3$ | (position-) $(R^4)_n$ | (position-) -A-Z | Physical data |
|---|---|---|---|---|
| III-87 | (4-) Br | — | 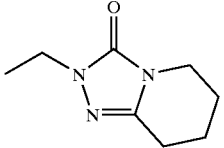 (2-) | logP = 1.63[a)] |
| III-88 | (4-) Br | — | 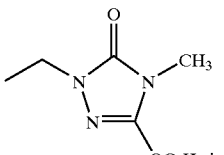 (2-) | logP = 2.27[a)] |
| III-89 | (4-) Br | — | 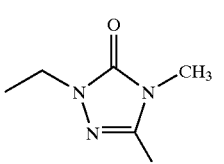 (2-) | logP = 2.31[a)] |
| III-90 | — | — | 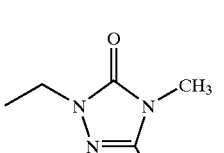 (2-) | logP = 1.82[a)] |
| III-91 | (4-) Br | — | 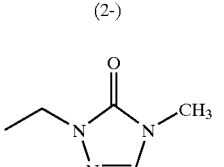 (2-) | $^1$H-NMR (CDCl$_3$, δ): 5.32 ppm. |
| III-92 | (4-) Br | — | 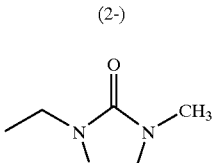 (2-) | $^1$H-NMR (CDCl$_3$, δ): 5.53 ppm. |
| III-93 | (4-) F | — | 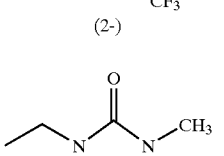 (2-) | $^1$H-NMR (CDCl$_3$, δ): 5.39 ppm. |

TABLE 2-continued

Examples of the compounds of the formula (III)

| Ex. No. | (position-) R³ | (position-) (R⁴)ₙ | (position-) -A-Z | Physical data |
|---|---|---|---|---|
| III-94 | (4-) F | — | triazolinone with N-ethyl, N-CH₃, CF₃ (2-) | ¹H-NMR (CDCl₃, δ): 5.57 ppm. |
| III-95 | (4-) F | — | triazolinone with N-ethyl, N-OC₂H₅, C₂H₅ (2-) | ¹H-NMR (CDCl₃, δ): 5.44 ppm. |
| III-96 | (4-) F | — | triazolinone with N-ethyl, N-CH₃, OCH₃ (2-) | ¹H-NMR (CDCl₃, δ): 5.41 ppm. |
| III-97 | — | — | triazolinone with N-ethyl, N-CH₃, OC₂H₅ (2-) | ¹H-NMR (CDCl₃, δ): 5.34 ppm. |
| III-98 | — | — | triazolinone with N-ethyl, N-CH₃, OCH₃ (2-) | ¹H-NMR (CDCl₃, δ): 5.38 ppm. |
| III-99 | — | — | triazolinone with N-ethyl, N-cyclopropyl, cyclopropyl (2-) | ¹H-NMR (CDCl₃, δ): 5.26 ppm. |
| III-100 | — | — | triazolinone with N-ethyl, N-CH₃, SCH₃ (2-) | ¹H-NMR (CDCl₃, δ): 5.43 ppm. |

TABLE 2-continued

Examples of the compounds of the formula (III)

| Ex. No. | (position-) $R^3$ | (position-) $(R^4)_n$ | (position-) -A-Z | Physical data |
|---|---|---|---|---|
| III-101 | — | — | (2-) triazolinone with ethyl, CH₃, SO₂CH₃ | logP = 1.23[a] |
| III-102 | (4-) SO₂CH₃ | — | (2-) triazolinone with ethyl, CH₃, OC₂H₅ | logP = 1.14[a] |
| III-103 | (4-) CF₃ | — | (2-) triazolinone with ethyl, CH₃, OC₃H₇-i | logP = 2.45[a] |
| III-104 | (4-) CF₃ | — | (2-) triazolinone with ethyl, CH₃, OC₃H₇-n | logP = 2.48[a] |
| III-105 | (4-) Br | — | (2-) triazolinone with ethyl, CH₃, Br | logP = 1.85[a] |
| III-106 | (4-) CF₃ | — | (3-) triazolinone with ethyl, cyclopropyl, OC₃H₇-i | logP = 2.74[a] |
| III-107 | (4-) CF₃ | — | (2-) triazolinone with ethyl, cyclopropyl, CH₂OCH₃ | logP = 2.01[a] |

TABLE 2-continued

Examples of the compounds of the formula (III)

| Ex. No. | (position-) R³ | (position-) (R⁴)ₙ | (position-) -A-Z | Physical data |
|---|---|---|---|---|
| III-108 | (4-) CF₃ | — | (2-) triazolinone with N-ethyl, N-CH₃, CH₂OCH₃ | logP = 1.79[a] |
| III-109 | (4-) CF₃ | — | (2-) triazolinone with N-ethyl, N-CH₃, Br | logP = 1.65[a] |
| III-110 | (4-) Br | — | (2-) triazolinone with N-ethyl, N-CH₃, SCH₃ | logP = 1.90[a] |
| III-111 | (4-) Cl | — | (2-) triazolinone with N-ethyl, N-CH₃, SCH₃ | logP = 1.83[a] |
| III-112 | (4-) I | — | (2-) triazolinone with N-ethyl, N-CH₃, OC₂H₅ | logP = 2.06[a] |
| III-113 | (4-) I | — | (2-) triazolinone with N-ethyl, N-CH₃, CF₃ | m.p.: 104° C. logP = 2.39[a] |
| III-114 | (4-) Br | — | (2) N-ethyl phthalazinone | m.p.: 191° C. |

TABLE 2-continued

Examples of the compounds of the formula (III)

| Ex. No. | (position-) R³ | (position-) (R⁴)ₙ | (position-) -A-Z | Physical data |
|---|---|---|---|---|
| III-115 | (4-) Br | — | (2-) benzotriazinone with N-ethyl | m.p.: 213° C. |
| III-116 | — | — | (2-) N-ethyl phthalimide | |
| III-117 | — | — | (2-) 1-ethyl-4-methyl-5-trifluoromethyl-1,2,4-triazol-3(4H)-one | m.p.: 112° C. |
| III-118 | (4-) CF₃ | — | (2-) 1-ethyl-4-methyl-5-trifluoromethyl-1,2,4-triazol-3(4H)-one | m.p.: 158° C. |
| III-119 | (4-) CF₃ | — | (2-) 1-ethyl-4-cyclopropyl-5-cyclopropyl-1,2,4-triazol-3(4H)-one | m.p.: 162° C. |
| III-120 | (4-) Cl | (5-) Cl | (2-) 1-ethyl-4-methyl-5-trifluoromethyl-1,2,4-triazol-3(4H)-one | m.p.: 167° C. |
| III-121 | — | — | (2-) 1-ethyl-4-methyl-5-hydroxy-1,2,4-triazol-3(4H)-one | m.p.: 188° C. |

TABLE 2-continued

Examples of the compounds of the formula (III)

| Ex. No. | (position-) R³ | (position-) (R⁴)ₙ | (position-) -A-Z | Physical data |
|---|---|---|---|---|
| III-122 | — | — | (2-) N-ethyl, 4-cyclopropyl, 5-cyclopropyl-1,2,4-triazol-3(2H)-one | |
| III-123 | — | — | (2-) N-ethyl, 4-CH₃, 5-CH₃-1,2,4-triazol-3(2H)-one | m.p.: 131° C. |
| III-124 | (4-) Cl | — | (2-) N-ethyl, 4-CH₃, 5-CF₃-1,2,4-triazol-3(2H)-one | m.p.: 109° C. |
| III-125 | (4-) I | — | (2-) N-ethyl, 4-CH₃, 5-CF₃-1,2,4-triazol-3(2H)-one | m.p.: 104° C. |
| III-126 | (4-) Br | — | (2-) N-ethyl, 4-CH₃, 5-CF₃-1,2,4-triazol-3(2H)-one | m.p.: 99° C. |
| III-127 | (4-) Br | — | (2-) N-ethyl, 4-cyclopropyl, 5-cyclopropyl-1,2,4-triazol-3(2H)-one | m.p.: 174° C. |
| III-128 | — | — | (2-) N-ethyl, 4-CH₃, 5-SCH₃-1,2,4-triazol-3(2H)-one | m.p.: 122° C. |

TABLE 2-continued

Examples of the compounds of the formula (III)

| Ex. No. | (position-) R³ | (position-) (R⁴)ₙ | (position-) -A-Z | Physical data |
|---|---|---|---|---|
| III-129 | (4-) Br | — | 1-ethyl-4-methyl-5-(methylthio)-1,2,4-triazol-3(4H)-one (2-) | m.p.: 164° C. |
| III-130 | — | — | 1-ethyl-4-methyl-5-(isopropoxy)-1,2,4-triazol-3(4H)-one (2-) | m.p.: 154° C. |
| III-131 | (4-) Br | — | 1-ethyl-4-methyl-5-(isopropoxy)-1,2,4-triazol-3(4H)-one (2-) | m.p.: 161° C. |
| III-132 | (4-) CN | — | 1-ethyl-4-methyl-5-(trifluoromethyl)-1,2,4-triazol-3(4H)-one (2-) | m.p.: 196° C. |
| III-133 | — | — | 2-ethylphthalazin-1(2H)-one (2-) | m.p.: 192° C. |
| III-134 | — | — | 1-ethyl-1,3-dihydro-2H-benzimidazol-2-one | |

The logP values given in Table 2 were determined in accordance with EEC Directive 79/831 Annex V.A8 by HPLC (High Performance Liquid Chromatography) using a reverse-phase column (C 18). Temperature: 43° C.

(a) Mobile phases for the determination in the acidic range: 0.1% aqueous phosphoric acid, acetonitrile; linear gradient from 10% acetonitrile to 90% acetonitrile—the corresponding data in Table 2 are labelled[a]).

(b) Mobile phases for the determination in the neutral range: 0.01 molar aqueous phosphate buffer solution, acetonitrile; linear gradient from 10% acetonitrile to 90% acetonitrile—the corresponding data in Table 2 are labelled[b]).

Calibration was carried out using unbranched alkan-2-ones (with from 3 to 16 carbon atoms) whose logP values are known (determination of the logP values by the retention times using linear interpolation between two successive alkanones).

The lambda-max values were determined in the maxima of the chromatographic signals, using the UV spectra from 200 nm to 400 nm.

Starting Materials of the Formula (IV)

Example (IV-1)

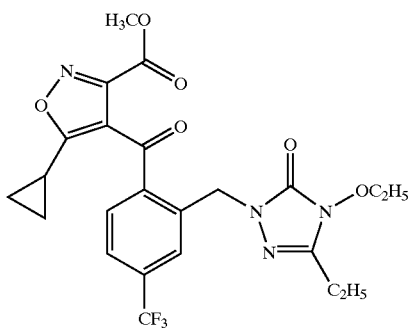

At room temperature (about 20° C.), a solution of 1.20 g (33% strength, i.e. 2.8 mmol) of methyl 4-(3-bromomethyl-5-trifluoromethyl-benzoyl)-5-cyclopropyl-isoxazole-3-carboxylate in 10 ml of N,N-dimethyl-formamide is added dropwise with stirring to a mixture of 0.44 g (2.8 mmol) of 4-ethoxy-5-ethyl-2,4-dihydro-3H-1,2,4-triazol-3-one, 84 mg (2.8 mmol) of sodium hydride (75% strength) and 20 ml of N,N-dimethyl-formamide, and the reaction mixture is stirred at room temperature for 30 minutes. The mixture is subsequently diluted with saturated aqueous sodium chloride solution to about twice its volume and extracted twice with ethyl acetate. The combined organic extract solutions are dried with sodium sulphate and filtered. The filtrate is concentrated under water pump vacuum and the residue is purified by column chromatography (silica gel, hexane/ethyl acetate, vol.: 7/3).

This gives 0.45 g (96% of theory based on 33% strength starting material) of (5-cyclopropyl-3-methoxycarbonyl-isoxazol-4-yl)-[2-(4-ethoxy-3-ethyl-5-oxo-4,5-dihydro-[1,2,4]-triazol-1-yl-methyl)-4-trifluoromethyl-phenyl]-methanone as an amorphous product.

logP (determined at pH=2.3): 3.56.

USES EXAMPLES

Example A

Pre-emergence Test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil. After about 24 hours, the soil is sprayed with the preparation of active compound such that the particuiar amount of active compound desired is applied per unit area. The concentration of the spray liquor is chosen so that the particular amount of active compound desired is applied in 1000 litres of water per hectare.

After three weeks, the degree of damage to the plants is rated in % damage in comparison to the development of the untreated control.

The figures denote:

0%=no effect (like untreated control)

100%=total destruction

In this test, for example, the compounds of Preparation Examples 1, 2, 3, 4, 5 and 6 exhibit strong activity against weeds, whilst being tolerated well by crop plants, such as, for example, maize.

Example B

Post-emergence Test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Test plants of a height of 5 to 15 cm are sprayed with the preparation of active compound such that the particular amounts of active compound desired are applied per unit area. The concentration of the spray liquor is chosen so that the particular amounts of active compound are applied in 1000 l of water/ha.

After three weeks, the degree of damage to the plants is rated in % damage in comparison to the development of the untreated control.

The figures denote:

0%=no effect (like untreated control)

100%=total destruction

In this test, for example, the compounds of Preparation Examples 1, 2, 3, 4, 5 and 6 exhibit strong activity against weeds, and some of them are tolerated well by crop plants, such as, for example, maize.

What is claimed is:

1. A compound of formula (I)

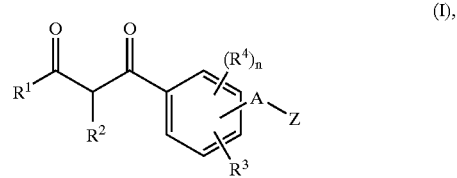

or tautomers thereof, or a salt of a compound of formula (I) or tautomers thereof, wherein n represents 0, 1, 2 or 3, A represents a single bond or represents alkanediyl (alkylene) having 1 to 4 carbon atoms, $R^1$ represents hydrogen, represents optionally cyano, carboxyl, carbamoyl, halogen, $C_1$–$C_4$-alkoxy-, $C_1$–$C_4$-alkylthio-, $C_1$–$C_4$-alkylsulphinyl- or $C_1$–$C_4$-alkylsulphonyl-substituted alkyl having 1 to 6 carbon atoms, or represents optionally cyano-, carboxyl-, carbamoyl-, halogen-, $C_1$–$C_4$-alkyl- or $C_1$–$C_4$-alkoxy-carbonyl-substituted cycloalkyl having 3 to 6 carbon atoms, $R^2$ represents hydrogen, cyano, carbamoyl, halogen, represents in each case optionally cyano-, carbamoyl-, halogen- or $C_1$–$C_4$-alkoxy-substituted alkyl, alkoxy or alkoxycarbonyl having in each case up to 6 carbon atoms, or represents in each case optionally halogen-substituted alkylthio, alkylsulphinyl or alkylsulphonyl having in each case 1 to 6 carbon atoms, $R^3$ represents hydrogen, nitro, cyano, carboxyl, carbamoyl, thiocarbamoyl, halogen, represents in each case optionally halogen-, $C_1$–$C_4$-alkoxy-, $C_1$–$C_4$-alkylthio-, $C_1$–$C_4$-alkylsulphinyl- or $C_1$–$C_4$-alkylsulphonyl-substituted alkyl, alkoxy, alkylthio, alkylsulphinyl or alkylsulphonyl having in each case up to 4 carbon atoms in the alkyl groups, or represents alkylamino, dialkylamino or dialkylaminosulphonyl having in each case up to 4 carbon atoms in the alkyl groups, R⁴ represents nitro, cyano, carboxyl, carbamoyl, thiocarbamoyl, halogen, represents in each case optionally halogen-, $C_1$–$C_4$-alkoxy-, $C_1$–$C_4$-alkylthio-, $C_1$–$C_4$-alkylsulphinyl- or $C_1$–$C_4$-alkylsulphonyl-substituted alkyl, alkoxy, alkylthio, alkylsulphinyl or alkylsuiphonyl having in each case up to 4 carbon atoms in the alkyl groups, or represents alkylamino, dialkylamino or dialkylaminosulphonyl having in each case up to 4 carbon atoms in the alkyl groups, and Z represents one of the heterocyclic groupings below

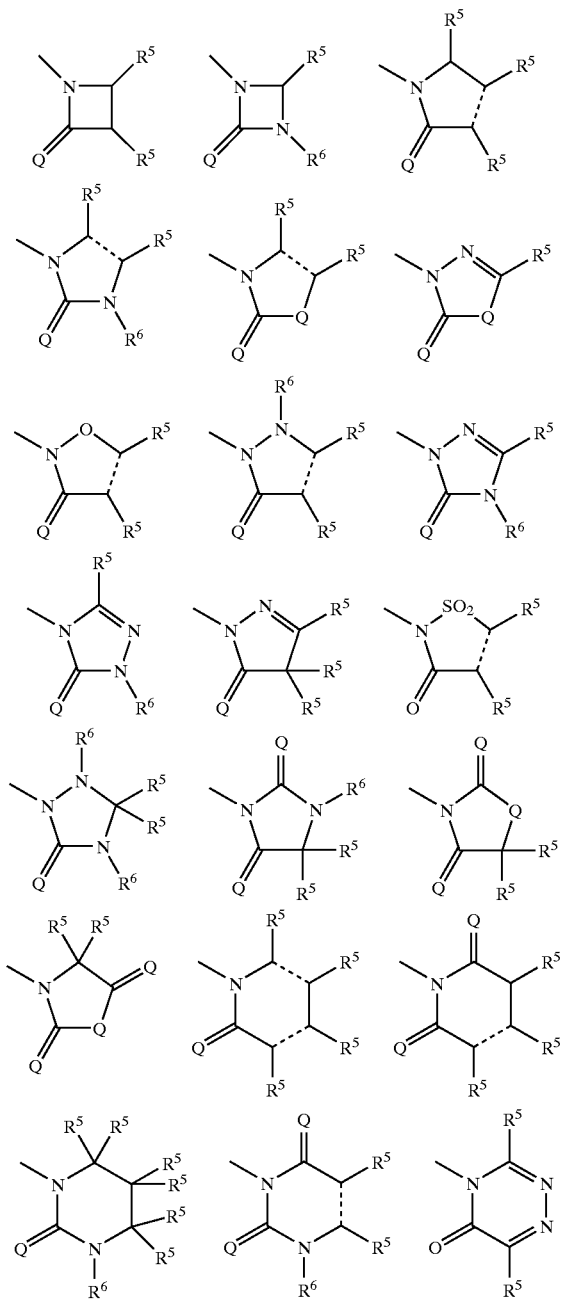
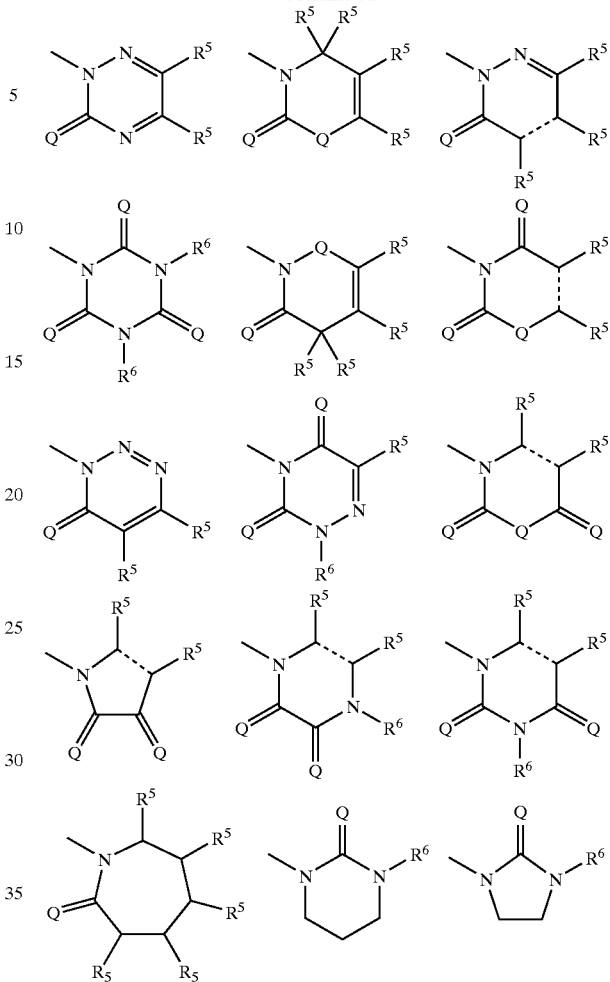

where the dotted line is in each case a single bond or a double bond,

Q represents oxygen or sulphur,

R⁵ represents hydrogen, hydroxyl, mercapto, cyano, halogen, represents in each case optionally cyano-, halogen-, $C_1$–$C_4$-alkoxy-, $C_1$–$C_4$-alkylthio-, $C_1$–$C_4$-alkylsulphinyl- or $C_1$–$C_4$-alkylsulphonyl-substituted alkyl, alkylcarbonyl, alkoxy, alkoxycarbonyl, alkylthio, alkylsulphinyl or alkylsulphonyl having in each case up to 6 carbon atoms in the alkyl groups, represents in each case optionally halogen-substituted alkylamino or dialkylamino having in each case up to 6 carbon atoms in the alkyl groups, represents in each case optionally halogen-substituted alkenyl, alkinyl, alkenyloxy, alkenylthio or alkenylamino having in each case up to 6 carbon atoms in the alkenyl- or alkinyl groups, represents in each case optionally halogen-substituted cycloalkyl, cycloalkyloxy, cycloalkylthio, cycloalkylamino, cycloalkylalkyl, cycloalkylalkoxy, cycloalkylalkylthio or cycloalkylalkylamino having in each case 3 to 6 carbon atoms in the cycloalkyl groups and optionally up to 4 carbon atoms in the alkyl moiety, or represents in each case optionally halogen-, $C_1$–$C_4$-alkyl- or $C_1$–$C_4$-alkoxy-substituted phenyl, phenyloxy, phenylthio, phenylamino, benzyl, benzyloxy, benzylthio or benzylamino, or—if two adjacent radicals R⁵ and R⁵ are located at a double bond—together with the adjacent radical R⁵ also represents a benzo grouping, and $R^6$ represents hydrogen, hydroxyl, amino, alkylideneamino having up to 4 carbon atoms, represents in each case optionally halogen- or $C_1$–$C_4$-alkoxy-substituted alkyl, alkoxy, alkylamino, dialkylamino or alkanoylamino having in each case up to 6 carbon atoms in the alkyl groups, represents in each case optionally halogen-substituted alkenyl, alkinyl or alkenyloxy having in each case up to 6 carbon atoms in the alkenyl- or alkinyl groups, represents in each case optionally halogen-substituted cycloalkyl, cycloalkylalkyl or cycloalkylamino having in each case 3 to 6 carbon atoms in the cycloalkyl groups and optionally up to 3 carbon atoms in the alkyl moiety, or represents in each case optionally halogen-, $C_1$–$C_4$-alkyl- or $C_1$–$C_4$-alkoxy-substituted phenyl or benzyl, or together with an adjacent radical $R^5$ or $R^6$ represents optionally halogen- or $C_1$–$C_4$-alkyl-substituted alkanediyl having 3 to 5 carbon atoms, where the individual radicals $R^5$ and $R^6$—if a plurality of them are attached to the same heterocyclic grouping—can have identical or different meanings within the scope of the above definition.

2. A compound according to claim 1, wherein

A represents a single bond, methylene, ethylidene (ethane-1,1-diyl) or dimethylene (ethane-1,2-diyl), $R^1$ represents hydrogen, represents in each case optionally cyano-, carboxyl-, carbamoyl-, fluorine-, chlorine-, methoxy-, ethoxy-, n- or i-propoxy-, methylthio-, ethylthio-, n- or i-propylthio-, methylsulphinyl-, ethylsulphinyl-, n- or i-propylsulphinyl-, methylsulphonyl-, ethylsulphonyl-, n- or i-propylsulphonyl-substituted methyl, ethyl, n- or i-propyl, n-, i-, s- or t-butyl, or represents in each case optionally cyano-, carboxyl-, carbamoyl-, fluorine-, chlorine-, methyl-, ethyl-, methoxycarbonyl- or ethoxycarbonyl-substituted cyclopropyl, cyclobutyl, cyclopentyl or cyclohexyl, $R^2$ represents hydrogen, cyano, carbamoyl, fluorine, chlorine, bromine, represents in each case optionally cyano-, carbamoyl-, fluorine-, chlorine-, methoxy- or ethoxy-substituted methyl, ethyl, n- or i-propyl, methoxy, ethoxy, n- or i-propoxy, methoxycarbonyl, ethoxycarbonyl, n- or i-propoxycarbonyl, or represents in each case optionally fluorine- and/or chlorine-substituted methylthio, ethylthio, n- or i-propylthio, methylsulphinyl, ethylsulphinyl, n- or i-propylsulphinyl, methylsulphonyl, ethylsulphonyl, n- or i-propylsulphonyl, $R^3$ represents hydrogen, nitro, cyano, carboxyl, carbamoyl, thiocarbamoyl, fluorine, chlorine, bromine, iodine, represents in each case optionally fluorine- and/or chlorine-, methoxy-, ethoxy-, n- or i-propoxy-, methylthio-, ethylthio-, n- or i-propylthio-, methylsulphinyl-, ethylsulphinyl-, methylsulphonyl- or ethylsulphonyl-substituted methyl, ethyl, n- or i-propyl, n-, i-, s- or t-butyl, represents in each case optionally fluorine- and/or chlorine-, methoxy-, ethoxy-, n- or i-propoxy-substituted methoxy, ethoxy, n- or i-propoxy, represents in each case optionally fluorine- and/or chlorine-substituted methylthio, ethylthio, n- or i-propylthio, methylsulphinyl, ethylsulphinyl, n- or i-propylsulphinyl, methylsulphonyl, ethylsulphonyl, n- or i-propylsulphonyl, or represents methylamino, ethylamino, n- or i-propylamino, dimethylamino, diethylamino, dimethylaminosulphonyl or diethylaminosulphonyl, $R^4$ represents nitro, cyano, carboxyl, carbamoyl, thiocarbamoyl, fluorine, chlorine, bromine, represents in each case optionally fluorine- and/or chlorine-, methoxy-, ethoxy-, n- or i-propoxy-, methylthio-, ethylthio-, n- or i-propylthio-, methylsulphinyl-, ethylsulphinyl-, methylsulphonyl- or ethylsulphonyl-substituted methyl, ethyl, n- or i-propyl, n-, i-, s- or t-butyl, represents in each case optionally fluorine- and/or chlorine-, methoxy-, ethoxy-, n- or i-propoxy-substituted methoxy, ethoxy, n- or i-propoxy, represents in each case optionally fluorine- and/or chlorine-substituted methylthio, ethylthio, n- or i-propylthio, methylsulphinyl, ethylsulphinyl, n- or i-propylsulphinyl, methylsulphonyl, ethylsulphonyl, n- or i-propylsulphonyl, or represents methylamino, ethylamino, n- or i-propylamino, dimethylamino, diethylamino, dimethylaminosulphonyl or diethylaminosulphonyl, $R^5$ represents hydrogen, hydroxyl, mercapto, cyano, fluorine, chlorine, bromine, iodine, represents in each case optionally fluorine-, chlorine-, methoxy-, ethoxy-, n- or i-propoxy-, n-, i-, s- or t-butoxy-, methylthio-, ethylthio-, n- or i-propylthio-, n-, i-, s- or t-butylthio-, methylsulphinyl-, ethylsulphinyl-, n- or i-propylsulphinyl-, methylsulphonyl-, ethylsulphonyl-, n- or i-propylsulphonyl-substituted methyl, ethyl, n- or i-propyl, n-, i-, s- or t-butyl, methoxy, ethoxy, n- or i-propoxy, n-, i-, s- or t-butoxy, methylthio, ethylthio, n- or i-propylthio, n-, i-, s- or t-butylthio, methylsulphinyl, ethylsulphinyl, n- or i-propylsulphinyl, methylsulphonyl, ethylsulphonyl, n- or i-propylsulphonyl, represents methylamino, ethylamino, n- or i-propylamino, n-, i-, s- or t-butylamino, dimethylamino, diethylamino, di-n-propylamino or di-i-propylamino, represents in each case optionally fluorine- and/or chlorine-substituted ethenyl, propenyl, butenyl, ethinyl, propinyl, butinyl, propenyloxy, butenyloxy, propenylthio, butenylthio, propenylamino or butenylamino, represents in each case optionally fluorine- and/or chlorine-substituted cyclopropyl, cyclobutyl, cyclopentyl, cyclohexyl, cyclopropyloxy, cyclobutyloxy, cyclopentyloxy, cyclohexyloxy, cyclopropylthio, cyclobutylthio, cyclopentylthio, cyclohexylthio, cyclopropylamino, cyclobutylamino, cyclopentylamino, cyclohexylamino, cyclopropylmethyl, cyclobutylmethyl, cyclopentylmethyl, cyclohexylmethyl, cyclopropylmethoxy, cyclobutylmethoxy, cyclopentylmethoxy, cyclohexylmethoxy, cyclopropylmethylthio, cyclobutylmethylthio, cyclopentylmethylthio, cyclohexylmethylthio, cyclopropylmethylamino, cyclobutylmethylamino, cyclopentylmethylamino or cyclohexylmethylamino, or represents in each case optionally fluorine-, chlorine-, methyl-, ethyl-, n- or i-propyl-, n-, i-, s- or t-butyl-, methoxy-, ethoxy-, n- or i-propoxy-substituted phenyl, phenyloxy, phenylthio, phenylamino, benzyl, benzyloxy, benzylthio or benzylamino, or—if two adjacent radicals $R^5$ and $R^5$ are located at a double bond—together with the adjacent radical $R^5$ also represents a benzo grouping, $R^6$ represents hydrogen, hydroxyl, amino, represents in each case optionally fluorine- and/or chlorine-, methoxy- or ethoxy-substituted methyl, ethyl, n- or i-propyl, n-, i- or s-butyl, methoxy, ethoxy, n- or i-propoxy, methylamino, ethylamino or dimethylamino, represents in each case optionally fluorine- and/or chlorine-substituted ethenyl, propenyl, ethinyl, propinyl or propenyloxy, represents in each case optionally fluorine- and/or chlorine-substituted cyclopropyl, cyclobutyl, cyclopentyl, cyclohexyl, cyclopropylmethyl, cyclobutylmethyl, cyclopentylmethyl or cyclohexylmethyl, or represents in each case optionally fluorine-, chlorine-, methyl-, ethyl-, n- or i-propyl-, n-, i-, s- or t-butyl-, methoxy-, ethoxy-, n- or i-propoxy-substituted phenyl or benzyl, or together with an adjacent radical $R^5$ or $R^6$ represents in each case optionally methyl- and/or ethyl-substituted propane-1,3-diyl (trimethylene), butane-1,4-diyl (tetramethylene) or pentane-1,5-diyl (pentamethylene), and Z represents one of the heterocyclic groupings below

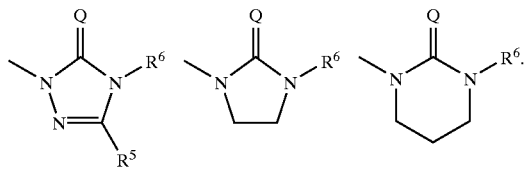

3. A compound according to 1, wherein n represents 0 or 1,

A represents a single bond or represents methylene, $R^1$ represents in each case optionally cyano-, fluorine-, chlorine-, methoxy-, ethoxy-, n- or i-propoxy-, methylthio-, ethylthio-, n- or o-propylthio-, methylsulphinyl-, ethylsulphinyl-, n- or i-propylsulphinyl-, methylsulphonyl-, ethylsulphonyl-, n- or i-propylsulphonyl-substituted methyl, ethyl, n- or i-propyl, or represents in each case optionally cyano-, fluorine-, chlorine-, methyl- or ethyl-substituted cyclopropyl, cyclobutyl, cyclopentyl or cyclohexyl, $R^2$ represents hydrogen, cyano, carbamoyl, fluorine, chlorine, bromine, represents in each case optionally cyano-, carbamoyl-, fluorine-, chlorine-, methoxy- or ethoxy-substituted methyl, ethyl, n- or i-propyl, or represents in each case optionally fluorine- and/or chlorine-substituted methylthio, ethylthio, n- or i-propylthio, methylsulphinyl, ethylsulphinyl, n- or i-propylsulphinyl, methylsulphonyl, ethylsulphonyl, n- or i-propylsulphonyl, $R^3$ represents hydrogen, nitro, cyano, carboxyl, carbamoyl, thiocarbamoyl, fluorine, chlorine, bromine, represents in each case optionally fluorine- and/or chlorine-, methoxy-, ethoxy-, n- or i-propoxy-, methylthio-, ethylthio-, n- or i-propylthio-, methylsulphinyl-, ethylsulphinyl-, methylsulphonyl- or ethylsulphonyl-substituted methyl, ethyl, n- or i-propyl, n-, i-, s- or t-butyl, represents in each case optionally fluorine- and/or chlorine-, methoxy-, ethoxy-, n- or i-propoxy-substituted methoxy, ethoxy, n- or i-propoxy, represents in each case optionally fluorine- and/or chlorine-substituted methylthio, ethylthio, n- or i-propylthio, methylsulphinyl, ethylsulphinyl, n- or i-propylsulphinyl, methylsulphonyl, ethylsulphonyl, n- or i-propylsulphonyl, or represents methylamino, ethylamino, n- or i-propylamino, dimethylamino, diethylamino, dimethylaminosulphonyl or diethylaminosulphonyl, $R^4$ represents methylsulphonyl, chlorine, methoxy, nitro, trifluoromethyl or methyl, $R^5$ represents hydrogen, hydroxyl, chlorine, bromine, methyl, ethyl, n- or i-propyl, n-, i-, s- or t-butyl, difluoromethyl, dichloromethyl, trifluoromethyl, trichloromethyl, chlorodifluoromethyl, fluorodichloromethyl, fluoroethyl, chloroethyl, difluoroethyl, dichloroethyl, fluoro-n-propyl, fluoro-i-propyl, chloro-n-propyl, chloro-i-propyl, methoxymethyl, ethoxymethyl, methoxyethyl, ethoxyethyl, methoxy, ethoxy, n- or i-propoxy, n-, i-, s- or t-butoxy, fluoroethoxy, chloroethoxy, difluoroethoxy, dichloroethoxy, trifluoroethoxy, trichloroethoxy, chlorofluoroethoxy, chlorodifluoroethoxy, fluorodichloroethoxy, methylthio, ethylthio, n- or i-propylthio, fluoroethylthio, chloroethylthio, difluoroethylthio, dichloroethylthio, chlorofluoroethylthio, chlorodifluoroethylthio, fluorodichloroethylthio, methylsulphinyl, ethylsulphinyl, n- or i-propylsulphinyl, methylsulphonyl, ethylsulphonyl, n- or i-propylsulphonyl, methylamino, dimethylamino, propenylthio, butenylthio, propinylthio, butinylthio, cyclopropyl, cyclopropylmethyl, cyclopropylmethoxy, phenyl or phenoxy, and $R^6$ represents amino, methyl, ethyl, n- or i-propyl, n-, i-, s- or t-butyl, methoxy, ethoxy, methylamino, dimethylamino, cyclopropyl or cyclopropylmethyl, or together with $R^5$ represents propane-1,3-diyl (trimethylene), butane-1,4-diyl (tetramethylene) or pentane-1,5-diyl (pentamethylene).

4. A compound according to claim 1, wherein $R^3$ represents hydrogen, nitro, cyano, fluorine, chlorine, bromine, methyl, trifluoromethyl or methoxy, $R^5$ represents hydrogen, bromine, chlorine, methyl, ethyl, trifluoromethyl, cyclopropyl, difluoroethyl, methylthio, ethylthio, methoxy, ethoxy, n- or i-propoxy, trifluoroethoxy, methylamino or dimethylamino and $R^6$ represents hydrogen, amino, methyl, ethyl, methoxy, ethoxy, cyclopropyl or dimethylamino.

5. A compound according to claim 1, wherein

Q represents oxygen (O).

6. A compound according to claim 1, wherein

Z represents the heterocyclic grouping

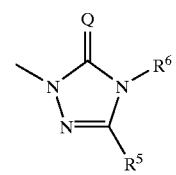

7. A compound according to claim 1, wherein $R^1$ represents cyclopropyl.

8. A compound according to claim 1, wherein $R^2$ represents hydrogen or cyano.

9. A compound according to claim 1, wherein $R^5$ represents bromine, methyl, ethyl, methoxy, methylthio, ethoxy, methylsulphonyl or dimethylamino, and $R^6$ represents amino, methyl, ethyl, cyclopropyl, dimethylamino, methoxy or ethoxy.

10. A compound according to claim 1 of the formula (IA)

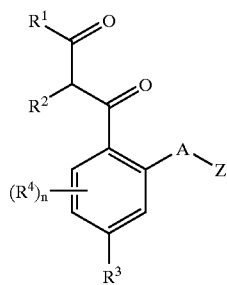

(IA)

wherein n, A, $R^1$, $R^2$, $R^3$, $R^4$ and Z are each as defined in claim 1.

11. A compound according to claim 1 of the formula (IB),

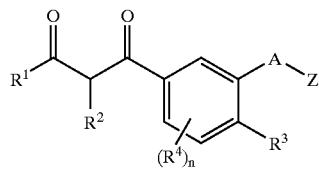

(IB)

wherein n, A, $R^1$, $R^2$, $R^3$, $R^4$ and Z are each as defined in claim 1.

12. A compound according to claim 1 of the formula (IC),

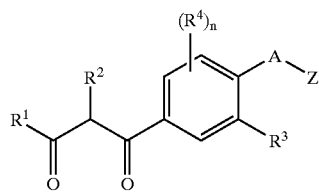

(IC)

wherein n, A, $R^1$, $R^2$, $R^3$, $R^4$ and Z are each as defined in claim 1.

13. A process for preparing compounds according to claim 2, comprising (a) reacting a ketone of the formula (II)

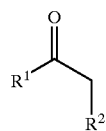

(II)

wherein $R^1$ and $R^2$ are each as defined in claim 2, with a substituted benzoic acid of the formula (III)

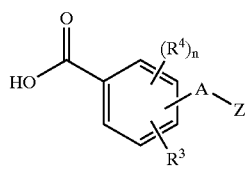

(III)

wherein n, A, $R^3$, $R^4$ and Z are each as defined in claim 1, or (b) isomerizing a benzoylisoxazole of the formula (IV)

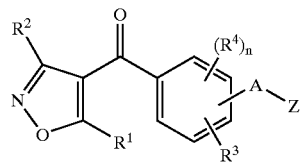

(IV)

wherein n, A, $R^1$, $R^2$, $R^3$, $R^4$ and Z are each as defined in claim 2, in the presence of one or more reaction auxiliaries.

14. A herbicidal composition comprising a compound according to claim 1 and an extender.

15. A method of controlling undesirable plants comprising applying a compound according to claim 1 to undesirable plants and/or their habitats.

16. A substituted benzoyl ketone according to claim 2, wherein

Q represents oxygen (O).

17. A sodium, potassium, magnesium, calcium, ammonium, $C_1$–$C_4$-alkyl-ammonium-, di($C_1$–$C_4$-alkyl)ammonium, tri($C_1$–$C_4$-alkyl)ammonium, tetra($C_1$–$C_4$-alkyl)ammonium, tri($C_1$–$C_4$-alkyl)sulphonium, $C_5$- or $C_6$-cycloalkyl-ammonium, or di($C_1$–$C_2$-alkyl)benzylammonium salt of a compound of formula (I) according to claim 1 or tautomers thereof.

* * * * *